United States Patent [19]

Rigg et al.

[11] Patent Number: 6,017,761
[45] Date of Patent: *Jan. 25, 2000

[54] METHOD FOR OBTAINING RETROVIRAL PACKAGING CELL LINES PRODUCING HIGH TRANSDUCING EFFICIENCY RETROVIRAL SUPERNATANT

[75] Inventors: Richard J. Rigg, Mountain View; Jingyi Chen, Fremont, both of Calif.; Jonathan S. Dando, Milan, Italy; Ivan Plavec; Sean P. Forestell, both of Menlo Park, Calif.; Ernst Bohnlein, Los Altos, Calif.

[73] Assignee: SyStemix, Inc., Palo Alto, Calif.

[*] Notice: This patent issued on a continued prosecution application filed under 37 CFR 1.53(d), and is subject to the twenty year patent term provisions of 35 U.S.C. 154(a)(2).
This patent is subject to a terminal disclaimer.

[21] Appl. No.: 08/817,452
[22] PCT Filed: Dec. 13, 1996
[86] PCT No.: PCT/US96/20777
§ 371 Date: Apr. 15, 1997
§ 102(e) Date: Apr. 15, 1997
[87] PCT Pub. No.: WO97/21825
PCT Pub. Date: Jun. 19, 1997

Related U.S. Application Data

[63] Continuation-in-part of application No. 08/572,959, Dec. 15, 1995, Pat. No. 5,910,434.
[51] Int. Cl.$^7$ .............. C12N 5/10; C12N 15/09; C12N 15/48; C12N 15/86
[52] U.S. Cl. .............. 435/455; 435/320.1; 435/325; 435/350; 435/357; 435/363; 435/364; 435/366; 435/369; 435/371; 536/23.72
[58] Field of Search .............. 435/172.3, 325, 435/363, 366, 350, 369, 357, 364, 371, 320.1, 455; 536/23.72

[56] References Cited

U.S. PATENT DOCUMENTS

| | | | |
|---|---|---|---|
| 4,683,195 | 7/1987 | Mullis et al. | 435/6 |
| 4,683,202 | 7/1987 | Mullis | 435/91.2 |
| 4,754,065 | 6/1988 | Levenson et al. | 562/564 |
| 4,800,159 | 1/1989 | Mullis et al. | 435/91.2 |
| 5,061,620 | 10/1991 | Tsukamoto et al. | 435/7.21 |
| 5,278,056 | 1/1994 | Bank et al. | 435/456 |
| 5,498,537 | 3/1996 | Bresler et al. | 435/235.1 |
| 5,591,624 | 1/1997 | Barber et al. | 435/366 |
| 5,686,279 | 11/1997 | Finer et al. | 435/172.3 |
| 5,716,826 | 2/1998 | Gruber et al. | 435/320.1 |

FOREIGN PATENT DOCUMENTS

| | | |
|---|---|---|
| WO 89/07150 | 8/1989 | WIPO . |
| WO 90/02806 | 3/1990 | WIPO . |
| 92/05266 | 4/1992 | WIPO . |
| WO 92/08796 | 5/1992 | WIPO . |
| WO 92/14829 | 9/1992 | WIPO . |
| WO 94/19478 | 9/1994 | WIPO . |
| WO 94/28143 | 12/1994 | WIPO . |
| WO 96/04934 | 2/1996 | WIPO . |

OTHER PUBLICATIONS

Delouis, et al., "Xenotropic and amphotropic pseudotyped recombinant retrovirus to transfer genes into cells from varicous species" *Biochem. Biophys. Res. Commun.* (1990) 169(1):8–14.
DeMonte, et al., "Gene transfer by retrovirus–derived shuttle vectors in the generation of murine bispecific monoclonal antibodies" *Proc. Natl. Acad. Sci.* (1990) 87(8):2941–2945.
Dougherty, et al. "New Retrovirus Helper Cells with Almost No Nucleotide Sequence Homology to Retrovirus Vectors" *J. Virol.* (1989) 63(7):3209–3212.
Gelinas, et al. "Retroviral vectors for the beta–globin gene that demonstrates improved titer and expression" *Ann. N.Y. Acad. Sci.* (1990) 612:427–441.
Lehn, P.M., "Gene therapy using bone marrow transplantation: a 1990 update" *Bone Marrow Transplant* (1990) 5(5):287–293.
Muenchau, et al., "Analysis of retroviral packaging lines for generation of replication–competent virus" *Virology* (1990) 176(1):262–265.
Sorge, et al., "Amphotropic retrovirus vector system for human cell gene transfer" *Mol. Cell. Biol.* (1984) 4(9):1730–1737.
SP. Forestell et al.; "Novel retroviral packaging cell lines: complementary tropisms and improved vector production for efficient gene transfer"; *Gene Therapy* (1997) 4, 600–610.
H. Chong et al.; "Replication–competent retrovirus produced by a 'split–function' third generation amphotropic packaging cell line"; *Gene Therapy* (1996) 3, 624–629.
Cosset et al., J. Virol. 69(12):7430–7436 (1995).
Markowitz et al., Journal of Virology 62(4):1120–1124 (1988).

(List continued on next page.)

*Primary Examiner*—Johnny F. Railey, II
*Attorney, Agent, or Firm*—Melissa A. Shaw

[57] ABSTRACT

This invention provides a method for obtaining a recombinant retroviral packaging cell capable of producing retroviral vectors as well as the recombinant packaging cell obtained by the method. Also provided is a method of producing recombinant retroviral particles obtained by introducing into the packaging cells obtained according to the methods disclosed herein, a recombinant retroviral vector and propagating the resulting producer cells under conditions favorable for the production and secretion of retroviral vector supernatant. The retroviral supernatant produced by these methods also is claimed herein. This invention further provides a method for screening retroviral vector supernatant for high transduction efficiency and methods for producing retroviral vector supernatant for transducing cells with high efficiency in gene therapy applications.

46 Claims, 24 Drawing Sheets

OTHER PUBLICATIONS

Markowitz et al., Virology 167(2):400–406 (1988).
Hoatlin et al., J. Mol. Med. 73:113–120 (1995).
Kotani et al., Human Gene Therapy 5:19–28 (1994).
Bagnis et al., "Leukemogenicity of v–myb–transformed monoblasts cells can be modulated by normal bone marrow environment" Oncogene (1993) 8:737–743.
Bevec et al., "Inhibition of human immunodeficiency virus type 1 replication in human T cells by retroviral–mediated gene transfer of a dominant–negative Rev trans–activator" Proc. Natl. Acad. Sci. USA (1992) 89:9870–9874.
Bonnerot et al., "A β–galactosidase hybrid protein targeted to nuclei as a marker for developmental studies" Proc. Natl. Acad. Sci. USA (1987) 84:6795–6799.
Burns et al., "Vesicular stomatitis virus G glycoprotein pseudotyped retroviral vectors: Concentration to very high titer and efficient gene transfer into mammalian and non-mammalian cells" Proc. Natl. Acad. Sci. USA (1993) 90:8033–8037.
Cornetta et al., "Infection of human cells with murine amphotropic replication–competent retroviruses" Human Gene Therapy (1993) 4:579–588.
Cosset et al., "Retroviral retargeting by envelopes expressing an N–terminal binding domain" J. Virol. (1995) 69(10):6314–6322.
Cosset et al., "Use of helper cells with two host ranges to generate high–titer retroviral vectors" Virology (1995) 193:385–395.
Danos et al., "Safe and efficient generation of recombinant retroviruses with amphotropic and ecotropic host ranges" Proc. Natl. Acad. Sci. USA (1988) 85:6460–6464.
Dranoff et al., "Vaccination with irradiated tumor cells engineered to secrete murine granulocyte–macrophage colony–stimulating factor stimulates potent, specific, and long–lasting anti–tumor immunity" Proc. Natl. Acad. Sci. USA (1993) 90:3539–3543.
Escaich et al., "RevM10–mediated inhibition of HIV–1 replication in chronically infected T cells" Human Gene Therapy (1995) 6:625–634.
Evans et al., "A neutralizable epitope common to the envelope glycoproteins of ecotropic, polytropic, xenotropic, and emphotropic murine leukemia viruses" J. Virol. (1990) 64(12):6176–6183.
Finer et al., "kat: A high efficiency retroviral transduction system for primary human T lymphocytes" Blood (1994) 83(1):43–50.
Forestell et al., "Improved detection of replication–competentretrovirus" J. Virol. Meth. (1996) 60:171–178.
Forestell et al., "Retroviral end–point titer is not predictive of gene transfer efficiency: implications for vector production" Gene Therapy (1995) 2:723–730.
Gilboa, "Retroviral gene transfer: Applications to human therapy" Adv. Exp. Med. Biol. (1988) 241:29–33.
"Gene Expression Technology" Methods in Enzymology (1991) Goeddel, et al. eds., Academic Press, Inc. New York. The title page and table of contents are enclosed herewith.
Haapala et al., "Isolation from cats of an endogenous type C virus with a novel envelope glycoprotein" J. Virol. (1985) 53(3):827–833.
Hodgson, "Expression Systems: A user's guide" Bio/Techniques (1993) 1:887–893.
Irving et al., "A reverese transcriptase–polymerase chain reaction assay for the detection and quantitation of murine retroviruses" Bio/Technol. (1993) 11:1042–1046.

Joshi et al., "Reduction in growth temperature minimizes instability of large plasmids containing HIV–1 proviral genomes" BioTechniques (1993) 14:880–886.
Kantoff et al., "Expression of human adenosine deaminase in nonhuman primates after retrovirus–mediated gene transfer" J. Exp. Med. (1987) 166:219–234.
Kasahara et al., "Tissue–specific targeting of retroviral vectors through ligand–receptor interactions" Science (1994) 266:1373–1376.
Kozak, "At least six nucleotides preceding the AUG initiator codon enhance translation in mammalian cells" J. Mol. Biol. (1987) 196:947–950.
Lander et al., "A Mus dunni cell line that lacks sequences closely related to endogenous murine leukemia viruses and can be infected by ecotropic, amphotropic, xenotropic, and mink cell focus–forming viruses" J. Virol. (1984) 52(2):695–698.
Luskey et al., "Gene transfer into murine hematopoietic stem cells and bone marrow stromal cells" Ann. N.Y. Acad. Sci. (1990) 612:398–406.
Marsh et al., "Retention of progenitor cell function in $CD34^+$cells purified using a novel O–sialoglycoprotease" Leukemia (1992) 6(9):926–934.
Miller et al., "Improved retroviral vectors for gene transfer and expression" BioTechniques (1989) 7(9):980–990.
Miller et al., "Redesign of retrovirus packaging cell lines to avoid recombination leading to helper virus production" Mol. Cell Biol. (1986) 6(8):2895–2902.
Miller et al., "Two base changes restore infectivity to a noninfectious molecular clone of moloney murine leukemia virus (pMLV–1)" J. Virol. (1984) 49:214–222.
Miller, "Progress toward human gene therapy" Blood (1990) 75(2):271–278.
Miller, "Retrovirus packaging cells" Human Gene Therapy (1990) 1:5–14.
Morgenstern et al., "Advanced mammalian gene transfer: high titre retroviral vectors with multiple drug selection markers and a complementary helper–free packaging cell line" Nucl. Acids. Res. (1990) 18(12):3587–3596.
"ORDA Reports. Recombinant DNA Advisory Committee (RAC). Data Management Report Jun. 1994" Human Gene Therapy (1994) 5:1293–1302.
Ott et al., "Sequence analysis of amphotropic and 10A1 murine leukemia viruses: Close relationship to mink cell focus–inducing viruses" J. Virol. (1990) 64(2):757–766.
Paul et al., "Increased viral titer through concentration of viral harvests from retroviral packaging lines" Human Gene Therapy (1993) 4:609–615.
PCR: The Polymerase Chain Reaction (1994) Mullis et al. eds., Birkhauser Press, Boston. The title page and table of contents are included herewith.
Pear et al., "Production of high–titer helper–free retroviruses by transient transfection" Proc. Natl. Acad. Sci. USA (1993) 90:8392–8396.
Plavec et al., "Sustained retroviral gene marking and expression in lymphoid and myeloid cells derived from transduced hematopoietic progenitor cells" Gene Therapy (1996) 3:717–724.
Printz et al., "Recombinant retroviral vector interferes with the detection of amphotropic replication competent retrovirus in standard culture assays" Gene Therapy (1995) 2:143–150.
Riele et al., "Consecutive inactivation of both alleles of the pim–1 proto–oncogene by homologous recombination in embryonic stem cells" Nature (1990) 348:649–651.

Rigg et al., "Detection of intracellular HIV–1 Rev Protein by flow cytometry" *J. Immunol. Meth.* (1995) 188:187–195.

Rigg et al., "A novel human amphotropic packaging cell line: high titer, complement resistance, and improved safety" *Virology* (1996) 218(1):290–295.

Sambrook et al., *Molecular Cloning. A Laboratory Manual,* 2nd ed., (1989) Cold Spring Harbor Laboratory Press, New York. A title page and table of contents are enclosed herewith.

Shinnick, et al., "Nucleotide sequence of Moloney murine leukaemia virus" *Nature* (1981) 293:543–548.

Smith, "Retroviral vector–mediated gene transfer into hematopoietic cells: Prospects and issues" *J. Hematother.*(1992)1:155–166.

Somia et al., "Generation of targeted retroviral vectors by using single–chain variable fragment: An approach to in vivo gene delivery" *Proc. Natl. Acad. Sci. USA* (1995) 92:7570–7574.

Soneoka et al., "A transient three–plasmid expression system for the production of high titer retroviral vectors", *Nucleic Acids Research* (1995) 23(4):628–633.

Sutherland et al., "Differential sensitivity of CD34 epitopes to cleavage by *Pasteurella haemolytica* glycoprotease: Implications for purification of CD34–positive progenitor cells" *Exp. Hematol.* (1992) 20:590–599.

Takeuchi et al., "Type C retrovirus inactivation by human complement is determined by both the viral genome and the producer cell" *J. Virol.* (1994) 68(12):8001–8007.

Technical Report Series No. 786 WHO, Geneva.

Vanin et al., "Characterization of replication–competent retroviruses from nonhuman primates with virus–induced T–cell lymphomas and observations regarding the mechanism of oncogenesis" *J. Virol.* (1994) 68(7):4241–4250.

Vara et al., "Expression in mammalian cells of a gene from *Streptomyces alboniger* conferring puromycin resistance" *Nucl. Acids. Res.* (1986) 14(11):4617–3624.

Xu et al., "Poor transduction efficiency of human hematopoietic progenitor cells by a high–titer amphotropic retrovirus producer cell clone" *J. Virol.* (1994) 68:7634–7636.

Yee et al., "A general method for the generation of high–titer, pantropic retroviral vectors: Highly efficient infection of primary hepatocytes" *Proc. Natl. Acad. Sci. USA* (1994) 91:9564–9568.

| VECTOR NAME | Structure |
|---|---|
| LMTNL |  |
| LMiLy |  |
| LLySN |  |
| SVNLZ |  |
| PG855 |  |
| BC140RevM10 |  |

METHOD FOR OBTAINING RETROVIRAL PACKAGING CELL LINES PRODUCING HIGH TRANSDUCING EFFICIENCY RETROVIRAL SUPERNATANT

This application is a national stage application of PCT/US96/20777 filed on Dec. 13, 1996, and a continuation-in-part of U.S. patent application Ser. No. 08/572,959, filed Dec. 15, 1995, issued on Jun. 8, 1999 as U.S. Pat. No. 5,910,434.

TECHNICAL FIELD OF THE INVENTION

This invention generally relates to the derivation and use of packaging cell lines for the production of retroviral transducing supernatant.

BACKGROUND OF THE INVENTION

Human gene transfer involves the transfer of one or more therapeutic genes and the sequences controlling their expression to appropriate target cells. A number of vector systems have been developed for the transfer of the therapeutic genes for various clinical indications. In vivo gene transfer involves the direct administration of vector to the target cells within a patient. Ex vivo gene transfer entails removing target cells from an individual, modifying them ex vivo and returning the modified cells to the patient.

The majority of gene therapy protocols approved for clinical trials by the NIH Recombinant DNA Advisory Committee (RAC) have used arnphotropic retroviral vectors (ORDA Reports Recombinant DNA Advisory Committee (RAC) Data Management Report, June 1994, (1994) *Human Gene Therapy* 5:1295–1302). Retroviral vectors are the vehicle of choice primarily due to the generally high rate of gene transfer obtained in experiments with cell lines and the ability to obtain stable integration of the genetic material, ensuring that the progeny of the modified cell will contain the transferred genetic material. For a review of retroviral vectors and their use in the transfer and expression of foreign genes, see Gilboa (1988) *Adv. Exp. Med. Biol.* 241:29; Luskey et al. (1990) *Ann. N.Y. Acad. Sci.* 612:398; and Smith (1992) *J. Hematother.* 1:155–166.

Many retroviral vectors currently in use are derived from the *Moloney murine* leukemia virus (MMLV). In most cases, the viral gag, pol and env sequences are removed from the virus, allowing for insertion of foreign DNA sequences. Genes encoded by the foreign DNA are often expressed under the control of the strong viral promoter in the LTR. Such a construct can be packaged into vector particles efficiently if the gag, pol and env functions are provided in trans by a packaging cell line. Thus, when the vector construct is introduced into the packaging cell, the Gag-Pol and Env proteins produced by the cell assemble with the vector RNA to produce replication-defective or transducing virions that are secreted into the culture medium. The vector particles thus produced can infect and integrate into the DNA of the target cell, but generally will not produce infectious virus since it is lacking essential viral sequences.

Most of the packaging cell lines currently in use have been transfected with separate plasmids encoding Gag-Pol and Env, so that multiple recombination events are necessary before a replication-competent retrovirus (RCR) can be produced. Commonly used retroviral vector packaging cell lines are based on the murine NIH/3T3 cell line and include PA317 (Miller & Buttimore (1986) *Mol. Cell Biol.* 6:2895; Miller & Rosman (1989) BioTechniques 7:980), CRIP (Danos & Mulligan (1988) *Proc. Natl Acad Sci USA* 85:6460), and gp+am12 (Markowitz et al. (1988) *Virology* 167:400). Although splitting the gag-pol and env genes within the packaging cell genome decreases the incidence of RCR, RCR is occasionally observed in clinical-scale productions of retroviral vector preparations and is a major safety concern. This is likely due, at least in part, to the fact that NIH/3T3 cells contain endogenous MLV sequences (Irving et al. (1993) *Bio/Technol.* 11:1042–1046) which could participate in recombination to form RCR (Cosset et al. (1993) *Virology* 193:385–395 and Vanin et al. (1994) *J Virology* 68:4241–4250), particularly in mass culture during large-scale clinical vector production.

The range of host cells that may be infected by a retrovirus or transduced by a retroviral vector is determined by the viral Env protein. The recombinant virus can be used to infect virtually any cell type recognized by the Env protein provided by the packaging cell, resulting in the integration of the viral genome in the transduced cell and the stable production of the foreign gene product. The efficiency of infection is also related to the level of expression of the receptor on the target cell. In general, murine ecotropic Env of MMLV allows infection of rodent cells, whereas amphotropic Env allows infection of rodent, avian and some primate cells, including human cells. Xenotropic vector systems utilizing murine xenotropic Env would also allow transduction of human cells.

The host range of retroviral vectors has been altered by substituting the Env protein of the base virus with that of a second virus. The resulting, "pseudotyped" vector particle has the host range of the virus donating the envelope protein and expressed by the packaging cell line. For example, the G-glycoprotein from vesicular stomatitis virus (VSV-G) has been substituted for the MMLV Env protein, thereby broadening the host range. See, e.g., Burns et al. (1993) *Proc. Natl. Acad. Sci USA* 90:8033–8037 and International PCT patent application Publication No. WO 92/14829.

Inconsistent results and inefficient gene transfer to some target cell types are two additional problems associated with current retroviral vector systems. For example, hematopoietic stem cells are an attractive target cell type for gene therapy because of their self-renewal capacity and their ability to differentiate into all hematopoietic lineages, thereby repopulating a patient with the modified cells. Yet retroviral gene transfer into hematopoietic stem cells has been inconsistent and disappointingly inefficient. Kantoff et al. (1987) *J. Exp. Med.* 166:219–234; Miller, A. D. (1990) *Blood* 76:271–278; and Xu et al. (1994) *J. Virol.* 68:7634. Efforts to increase gene transfer efficiency include producing higher end-point-titer retroviral vector supernatants. End-point titer is a measure of the number of functional vector particles in a preparation which, when increased, should theoretically increase transduction efficiency by increasing the ratio of functional vector to target cells, i.e. increasing multiplicity of infection (m.o.i.). Despite increased end-point titers, however, retroviral gene transfer efficiency (transduction efficiency) has not increased correspondingly (Xu et al. (1994), supra; Paul (1993) *Hum. Gene Therapy* 4:609–615; Fraes-Lutz et al. (1994) 22:857–865).

Efforts to increase end-point titer have included improving production of retroviral vector supernatants (see Kotani et al. (1994) *Human Gene Therapy*, 5:19–28) and physical concentration of vector particles by ultrafiltration (Paul, et al. (1993), supra. and Kotani, et al. (1994) supra). It was shown that incubation of producer cells at 32° C. rather than at 37° C. yielded supernatants with higher end-point titers, but transduction efficiencies were not compared (See Kotani, et al. (1994) supra). The authors of Kotani et al.

(1994) supra, postulated that the higher titers were due to a lower rate of inactivation combined with a faster rate of virion production at 32° C. In another study, transduction efficiency was measured before and after concentration of three supernatants with similar end-point titers Paul et al. (1993) supra. In each case, concentration increased endpoint titer and modestly improved the transduction efficiency. However, the transduction efficiency achieved with one of the unconcentrated supernatants was significantly higher than that achieved with the other concentrates (Paul et al. (1993) supra).

For in vivo gene therapy applications, it is important that the retroviral vector not be inactivated by human serum before transducing the target cells. Reports show that human serum inactivates a number of recombinant retroviruses, apparently via a complement pathway. Both viral envelope and producer cell components have been reported to be responsible for viral sensitivity to human complement (Takeuchi et al. (1994) *J. Virol.* 68(12):8001).

Thus, a need exists for methods of reproducibly increasing transduction efficiency and for providing stable, safe packaging cell lines for producing high transduction efficiency retroviral preparations. This invention satisfies these needs and provides related advantages as well.

SUMMARY OF THE INVENTION

This invention provides, inter alia, a method for obtaining a recombinant retroviral packaging cell capable of producing retroviral vectors. In one embodiment, the method comprises the steps of selecting a retrovirus and obtaining a cell free of endogenous retroviral nucleic acid. These steps are interchangeably performed. However, after selection of the retrovirus, a minimal gag-pol open reading frame (ORF) insert is isolated from the retrovirus. Alternatively, a nucleic acid molecule coding for functionally equivalent retroviral minimal ORF can be isolated and used in the methods disclosed herein. In the same manner, a minimal env ORF is isolated from wild type retrovirus or an equivalent nucleic acid molecule is obtained. The minimal ORF nucleic acid molecules are then amplified, either by insertion into a suitable replication vector or plasmid and replication of a host cell containing the vector and/or plasmid or by other non-biological methods (PCR). After amplification, and consistent with the method of amplification, the minimal ORF nucleic acid molecules are inserted into a cell preselected to be devoid of endogenous retroviral nucleic acid. The transformed cells are then propagated under conditions favorable for expression of the minimal retroviral gag-pol and env ORF.

Suitable candidate packaging cell lines include, but are not limited to mammalian cells such as COS, Vero, HT-1080, D17 MRC-5, FS-4, TE671, human embryonic kidney (293), and HeLa.

The invention also provides the use of an ELISA method to screen for production of retroviral structural proteins to identify a retroviral packaging cell capable of producing recombinant, transducing retroviral vector particles. In further embodiment of this method, the cells that produce high levels of the retroviral Gag-Pol protein and the retroviral Env protein are identified or selected for by assaying for gag-pol and/or env ORF translation products in the supernatant.

This invention also provides the recombinant packaging cell obtained by the methods in all various embodiments described herein, including the amphotropic cell line designated ProPak-A and the xenotropic packaging cell line designated ProPak-X. Other embodiments of the packaging cell lines produced by the methods disclosed herein are packaging cell lines characterized by having the ability to produce transducing supernatant that is: resistant to human complement; has a transducing efficiency of greater than or equal to 50% when assayed on NIH/3T3 cells, or greater than that achieved with supernatant from PA317-based cells, or has a transducing efficiency of greater than or equal to 20% when assayed on 293 cells; and substantially free of RCR after interaction of retroviral vector sequences and continuous culture of more than 2 weeks with an indicator cell line.

Further provided by this invention is a method of producing recombinant retroviral particles obtained by introducing into the packaging cells obtained according to the methods disclosed herein, a recombinant retroviral vector and propagating the resulting producer cells under conditions favorable for the production and secretion of retroviral vector supernatant.

With respect to the propagation of the producer cells, methods are provided for obtaining a retroviral vector supernatant having high transduction efficiency by culturing the producer cells in a packed-bed bioreactor and harvesting the resultant supernatant. In one method, the packed-bed bioreactor has a surface to volume ratio of 5 to 50 $cm^2/ml$, and the producer cells are cultured at a temperature of 30° C. to about 37° C.

The retroviral supernatants produced by these methods are also claimed herein.

This invention also provides a method for screening retroviral vector supernatant for high transduction efficiency and methods for producing retroviral vector supernatant for transducing cells with high efficiency in gene therapy applications.

Yet another embodiment of the invention is a method of increasing the transduction efficiency of a cell by transducing a cell with a retroviral vector supernatant obtained from the culture of one or more recombinant packaging cells produced by the methods of the invention. Vector supernatant containing particles of more than one tropism can be produced by the co-culture of two or more producer cells of complementary tropisms.

The present invention provides a method of producing viral vector supernatant of high transduction efficiency. The prevailing view in the art is that increasing the viral titer will result in an increase in the transduction efficiency. As shown herein, this is not the case. Rather, higher transduction efficiency is correlated with increased numbers of functional vector particles. Vector particles are not all produced identically and high titer supernatants can contain many nontransducing particles.

DESCRIPTION OF THE FIGURES

FIG. 4A is a comparison of the transduction efficiency of Lyt-2-encoding (LMiLy vector) viral supernatants produced from ProPak-A and PA317 cells cultured in a packed-bed bioreactor, as assayed on NIH/3T3 cells. FIG. 4B is a comparison of the transduction efficiency of vector supernatants (LMiLy vector) produced from ProPak-A and PA 317 cells cultured in an aerated packed-bed bioreactor, as assayed on 293 cells. FIG. 4C is a comparison of the transduction efficiencies achieved with Lyt2-encoding (LLySN) vector supernatants produced from PA317 or ProPak-A-based producer cells, as the proportion (%) of NIH/3T3 cells that stained with anti-Lyt2 antibody (Pharmingen, San Diego, Calif.) 2 days after inoculation of the NIH/3T3 cells with the dilutions of vector supernatant shown. Supernatants were prepared from confluent producer cell cultures after culturing for 12 hours at 32° C.

FIG. 5B is a comparison of transduction efficiencies measured on NIH/3T3, HeLa or Jurkat cells for three PA.LMTNL supernatants with the end-point titer measured on NIH/3T3 cells. 1E+05 means an end-point titer of 1×10$^5$ cfu/ml on NIH/3T3 cells. Error bars show the standard error for three determinations.

FIGS. 8A and 8B show the time-course of production of PA.SVNLZ retroviral vector in a 75 cm$^2$ tissue culture flask at 32° C. or 37° C. measured as either transduction efficiency (FIG. 8A) or end-point titer on NIH/3T3 cells (FIG. 8B) or.

FIG. 16A shows transduction after spinoculation with single supernatants. FIG. 16B shows transduction after spinoculation with single or mixed (ampho+xeno) supernatant.

In FIG. 17A, cell lines were inoculated at unit gravity with LLySN vector from ProPak-X (PP-X), ProPak-A (PP-A), or PG13 (PG)-based producer populations. MLV(V-G). LMiLy is an MLV(VSV-G) pseudotype supernatant prepared by transient transfection. In FIG. 17B, Quail cells (Qcl. 3; Cullen et al., 1983) were inoculated with LMiLy vector particles bearing the chimeric envelope (Eax; prepared by transient transfection), the xenotropic (ProPak-X) or the amphotropic (ProPak-A) envelope.

MODE(S) FOR CARRYING OUT THE INVENTION

Definitions

Figure 1:
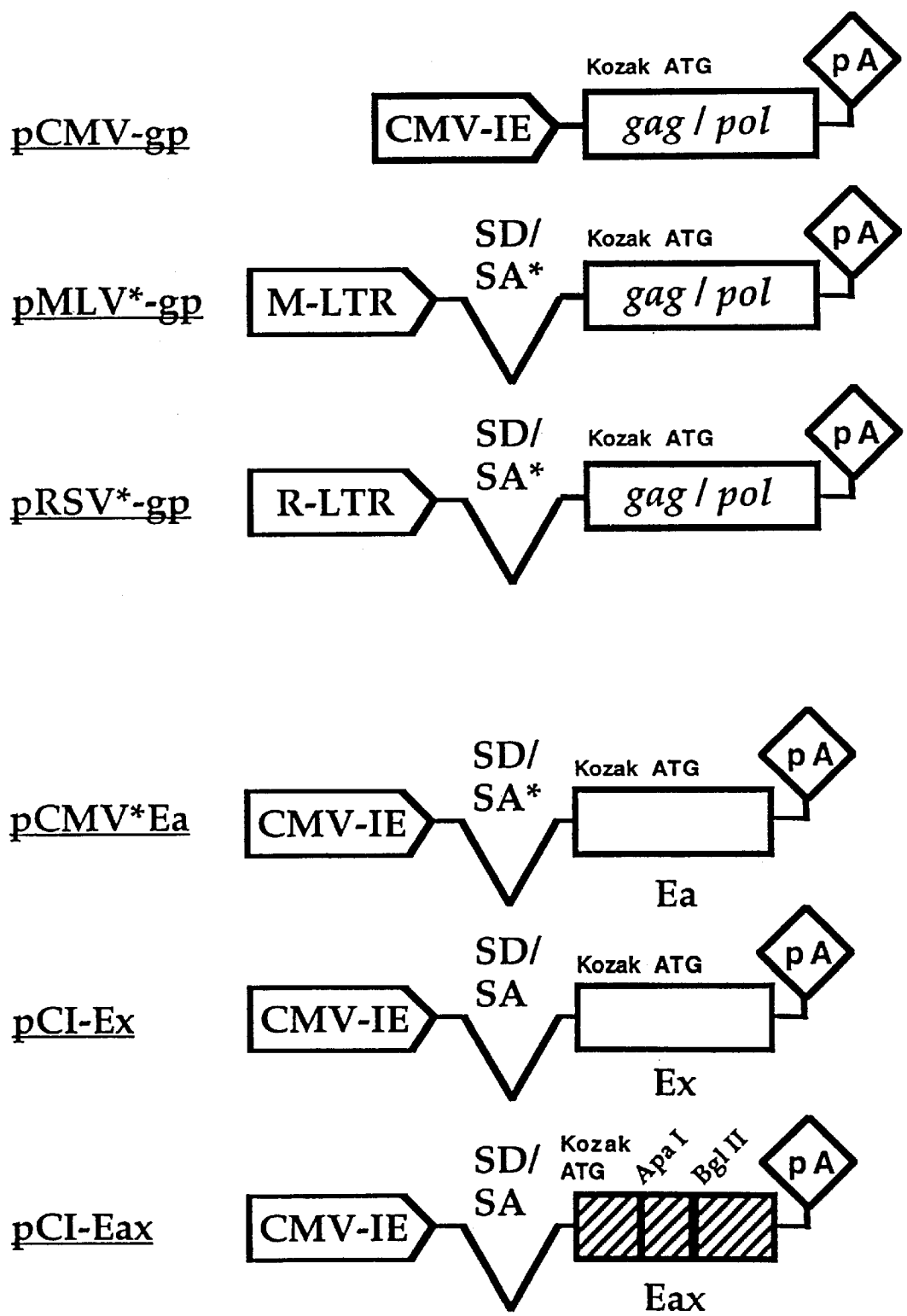
FIG. 1 schematically shows the plasmid constructs for expression of MLV structural genes, that were used as insertion plasmids for construction of the packaging cell lines ProPak-A and Pro-Pak-X. The top three constructs are for expression of Gag-Pol and the bottom three are Env expression constructs. Minimal MLV sequences are a common feature among these plasmids. CMV-IE denotes cytomegalovirus immediate early promoter. SD/SA denotes splice donor/splice acceptor site. MLV is the murine leukemia viral promoter present in the viral LTR. RSV LTR is the LTR promoter of Rous Sarcoma Virus. SV40 denotes the simian virus 40 early promoter. pA is the poly-adenylation site. Ea refers to the amphotropic envelope gene, Ex refers to the xenotropic envelope gene, and Eax denotes the chimeric ampho/xenotropic envelope gene.

Unless otherwise specified herein, common definitions are intended by the words and terms used herein. For example, "retrovirus" denotes a class of viruses which use RNA-directed DNA polymerase, or "reverse transcriptase" to copy a viral RNA genome into a double-stranded DNA intermediate which can be incorporated into chromosomal DNA (a "provirus") of an avian or mammalian host cell. Retrovirus also exist as free virions, that contain the structural and enzymatic proteins of the retrovirus (including reverse transcriptase), two copies of the viral genome, and portions of the host cell's plasma membrane in which is embedded the viral envelope glycoprotein. Many such retroviruses are known to those skilled in the art and are described, for example, in Weiss et al., eds, *RNA Tumor Viruses*, 2nd ed., Cold Spring Harbor Press, Cold Spring Harbor, N.Y. (1984 and 1985). Plasmids containing retroviral genomes also are widely available from the American Type Culture Collection (ATCC), and other sources as described in Gacesa and Ramji, *Vectors: Essential Data*, John Wiley & Sons, New York (1994). The nucleic acid sequences of a large number of these viruses are known and are generally available from databases such as GENBANK, for example. The complete nucleic acid sequence of the MoMLV and other MLVs is known in the art.

"Packaging cell line" is a recombinant cell line containing nucleic acid expressing retroviral Gag, Pol and Env structural proteins. Because the packaging cell line lacks the retroviral nucleic acid coding for packaging signal and other cis-acting elements, infectious virions cannot be produced.

A "producer cell" is a packaging cell as defined above which also contains a replication-defective retroviral vector which is packaged into the vector particle. The producer cell produces transducing retroviral-based particles containing "foreign" (i.e., non-retroviral) genes, such as therapeutic or marker genes.

A "target cell" is a cell to be transduced with a recombinant retroviral vector. Thus, target cells may be, for example, a cell line used for assessing the quality of a retroviral vector preparation, a primary cell for genetic modification ex vivo, or a cell within a patient that will be modified by in vivo introduction of a retroviral vector.

The terms "polynucleotide", "oligonucleotide", "nucleic acids" and "nucleic acid molecules" are used interchangeably, and refer to a polymeric form of nucleotides of any length, either deoxyribonucleotides or ribonucleotides, or analogs thereof. Polynucleotides may have any three-dimensional structure, and may perform any function, known or unknown. The following are non-limiting examples of polynucleotides: a gene or gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

The term polynucleotide, as used herein, refers interchangeably to double- and single-stranded molecules. Unless otherwise specified or required, any embodiment of the invention described herein that is a polynucleotide encompasses both the double-stranded form and each of two complementary single-stranded forms known or predicted to make up the double-stranded form.

A "gene" can refer to a polynucleotide or a portion of a polynucleotide comprising a sequence that encodes a protein. It is often desirable for the gene also to comprise a promoter operatively linked to the coding sequence in order to effectively promote transcription. Enhancers, repressors and other regulatory sequences also can be included in order to modulate activity of the gene, as is well known in the art (see, e.g., the references cited herein).

A "detectable marker" gene is a gene that allows cells carrying the gene to be specifically detected (i.e., to be distinguished from cells which do not carry the marker gene). A large variety of such marker genes are known in the art. Preferred examples of such marker genes encode proteins appearing on cellular surfaces, thereby facilitating simplified and rapid detection and/or cellular sorting.

A "selectable marker" gene is a gene that allows cells carrying the gene to be specifically selected for or against, in the presence of a corresponding selective agent. By way of illustration, an antibiotic resistance gene can be used as a positive selectable marker gene that allows a host cell to be positively selected for in the presence of the corresponding antibiotic. A variety of positive and negative selectable markers are known in the art, some of which are described herein.

In the context of polynucleotides, a "linear sequence" or a "sequence" is an order of nucleotides in a polynucleotide in a 5' to 3' direction in which residues that neighbor each other in the sequence are contiguous in the primary structure of the polynucleotide. A "partial sequence" is a linear sequence of part of a polynucleotide which is known to comprise additional residues in one or both directions.

"Hybridization" refers to a reaction in which one or more polynucleotides react to form a complex that is stabilized via hydrogen bonding between the bases of the nucleotide residues. The hydrogen bonding may occur by Watson-Crick base pairing, Hoogsteen binding, or in any other sequence-specific manner. The complex may comprise two strands forming a duplex structure, three or more strands forming a multi-stranded complex, a single self-hybridizing strand, or any combination of these. A hybridization reaction may constitute a step in a more extensive process, such as the initiation of a PCR, or the enzymatic cleavage of a polynucleotide by a ribozyme.

Hybridization reactions can be performed under conditions of different "stringency". Conditions that increase the stringency of a hybridization reaction are widely known and published in the art: See, for example, Sambrook et al. (1989) infra "$T_m$" is the temperature in degrees Centigrade at which 50% of a polynucleotide duplex made of complementary strands hydrogen bonded in an antiparallel direction by Watson-Crick base paring dissociates into single strands under the conditions of the experiment. $T_m$ may be predicted according to standard formula; for example:

$$T_m=81.5+16.6 \log[Na^+]+0.41\ (\%\ G/C)-0.61\ (\%\ F)-600/L$$

where $Na^+$ is the cation concentration (usually sodium ion) in mol/L; (% G/C) is the number of G and C residues as a percentage of total residues in the duplex; (% F) is the percent formamide in solution (wt/vol); and L is the number of nucleotides in each strand of the duplex.

A linear sequence of nucleotides is "identical" to another linear sequence, if the order of nucleotides in each sequence is the same, and occurs without substitution, deletion, or material substitution. It is understood that purine and pyrimidine nitrogenous bases with similar structures can be functionally equivalent in terms of Watson-Crick base-pairing; and the inter-substitution of like nitrogenous bases, particularly uracil and thymine, or the modification of nitrogenous bases, such as by methylation, does not constitute a material substitution. An RNA and a DNA polynucleotide have identical sequences when the sequence for the RNA reflects the order of nitrogenous bases in the polyribonucleotide, the sequence for the DNA reflects the order of nitrogenous bases in the polydeoxyribonucleotide, and the two sequences satisfy the other requirements of this definition. Where at least one of the sequences is a degenerate oligonucleotide comprising an ambiguous residue, the two sequences are identical if at least one of the alternative forms of the degenerate oligonucleotide is identical to the sequence with which it is being compared. For example, AYAAA is identical to ATAAA, if AYAAA is a mixture of ATAAA and ACAAA.

When comparison is made between polynucleotides, it is implicitly understood that complementary strands are easily generated, and the sense or antisense strand is selected or predicted that maximizes the degree of identity between the polynucleotides being compared. For example, where one or both of the polynucleotides being compared is double-stranded, the sequences are identical if one strand of the first polynucleotide is identical with one strand of the second polynucleotide. Similarly, when a polynucleotide probe is described as identical to its target, it is understood that it is the complementary strand of the target that participates in the hybridization reaction between the probe and the target.

A linear sequence of nucleotides is "essentially identical" to another linear sequence, if both sequences are capable of hybridizing to form duplexes with the same complementary polynucleotide. Sequences that hybridize under conditions of greater stringency are more preferred. It is understood that hybridization reactions can accommodate insertions, deletions, and substitutions in the nucleotide sequence. Thus, linear sequences of nucleotides can be essentially identical even if some of the nucleotide residues do not precisely correspond or align. Sequences that correspond or align more closely to the invention disclosed herein are comparably more preferred. Generally, a polynucleotide region of about 25 residues is essentially identical to another region, if the sequences are at least about 80% identical; more preferably, they are at least about 90% identical; more preferably, they are at least about 95% identical; still more preferably, the sequences are 100% identical. A polynucleotide region of 40 residues or more will be essentially identical to another region, after alignment of homologous portions if the sequences are at least about 75% identical; more preferably, they are at least about 80% identical; more preferably, they are at least about 85% identical; even more preferably, they are at least about 90% identical; still more preferably, the sequences are 100% identical.

In determining whether polynucleotide sequences are essentially identical, a sequence that preserves the functionality of the polynucleotide with which it is being compared is particularly preferred. Functionality can be determined by different parameters. For example, if the polynucleotide is to be used in reactions that involve hybridizing with another polynucleotide, then preferred sequences are those which hybridize to the same target under similar conditions. In general, the $T_m$ of a DNA duplex decreases by about 10° C. for every 1% decrease in sequence identity for duplexes of 200 or more residues; or by about 50° C. for duplexes of less than 40 residues, depending on the position of the mismatched residues. Essentially identical sequences of about 100 residues will generally form a stable duplex with each other's respective complementary sequence at about 20° C. less than $T_m$; preferably, they will form a stable duplex at about 15° C. less; more preferably, they will form a stable duplex at about 10° C. less; even more preferably, they will form a stable duplex at about 50° C. less; still more preferably, they will form a stable duplex at about $T_m$. In another example, if the polypeptide encoded by the polynucleotide is an important part of its functionality, then preferred sequences are those which encode identical or essentially identical polypeptides. Thus, nucleotide differences which cause a conservative amino acid substitution are preferred over those which cause a non-conservative substitution, nucleotide differences which do not alter the amino acid sequence are more preferred, while identical nucleotides are even more preferred. Insertions or deletions in the polynucleotide that result in insertions or deletions in the polypeptide are preferred over those that result in the down-stream coding region being rendered out of phase; polynucleotide sequences comprising no insertions or deletions are even more preferred. The relative importance of hybridization properties and the encoded polypeptide sequence of a polynucleotide depends on the application of the invention.

A polynucleotide has the same "characteristics" of another polynucleotide if both are capable of forming a stable duplex with a particular third polynucleotide under similar conditions of maximal stringency. Preferably, in addition to similar hybridization properties, the polynucleotides also encode essentially identical polypeptides.

"Conserved" residues of a polynucleotide sequence are those residues which occur unaltered in the same position of two or more related sequences being compared. Residues that are relatively conserved are those that are conserved amongst more related sequences than residues appearing elsewhere in the sequences.

"Related" polynucleotides are polynucleotides that share a significant proportion of identical residues.

A "probe" when used in the context of polynucleotide manipulation refers to an oligonucleotide which is provided as a reagent to detect a target potentially present in a sample of interest by hybridizing with the target. Usually, a probe will comprise a label or a means by which a label can be attached, either before or subsequent to the hybridization reaction. Suitable labels include, but are not limited to radioisotopes, fluorochromes, chemiluminescent compounds, dyes, and proteins, including enzymes.

A "primer" is an oligonucleotide, generally with a free 3'-OH group, that binds to a target potentially present in a sample of interest by hybridizing with the target, and thereafter promotes polymerization of a polynucleotide complementary to the target.

Processes of producing replicate copies of the same polynucleotide, such as PCR or gene cloning, are collectively referred to herein as "amplification" or "replication". For example, single or double-stranded DNA may be replicated to form another DNA with the same sequence. RNA may be replicated, for example, by an RNA-directed RNA polymerase, or by reverse-transcribing the DNA and then performing a PCR. In the latter case, the amplified copy of the RNA is a DNA with the identical sequence.

A "polymerase chain reaction" ("PCR") is a reaction in which replicate copies are made of a target polynucleotide using one or more primers, and a catalyst of polymerization, such as a reverse transcriptase or a DNA polymerase, and particularly a thermally stable polymerase enzyme. Generally, a PCR involves reiteratively forming three steps: "annealing", in which the temperature is adjusted such that oligonucleotide primers are permitted to form a duplex with the polynucleotide to be amplified; "elongating", in which the temperature is adjusted such that oligonucleotides that have formed a duplex are elongated with a DNA polymerase, using the polynucleotide to which they have formed the duplex as a template; and "melting", in which the temperature is adjusted such that the polynucleotide and elongated oligonucleotides dissociate. The cycle is then repeated until the desired amount of amplified polynucleotide is obtained. Methods for PCR are taught in U.S. Pat. Nos. 4,683,195 (Mullis) and 4,683,202 (Mullis et al.).

A "control element" or "control sequence" is a nucleotide sequence involved in an interaction of molecules that contributes to the functional regulation of a polynucleotide, including replication, duplication, transcription, splicing, translation, or degradation of the polynucleotide. The regulation may affect the frequency, speed, or specificity of the process, and may be enhancing or inhibitory in nature. Control elements are known in the art. For example, a "promoter" is an example of a control element. A promoter is a DNA region capable under certain conditions of binding RNA polymerase and initiating transcription of a coding region located downstream (in the 3' direction) from the promoter. Retroviral long terminal repeat sequences (LTR) contain strong promoters that are suitably used in the inventions described herein.

"Operatively linked" refers to a juxtaposition of genetic elements, wherein the elements are in a relationship permitting them to operate in the expected manner. For instance, a promoter is operatively linked to a coding region if the promoter helps initiate transcription of the coding sequence. There may be intervening residues between the. promoter and coding region so long as this functional relationship is maintained.

The "gag" gene of a retrovirus refers to the 5' gene on retrovirus genomes and is an abbreviation for group-specific antigens. It is translated to give a precursor polyprotein which is subsequently cleaved to yield three to five capsid proteins.

The "pol" gene refers to a gene encoding a polymerase. Thus, the pol gene encodes for a retrovirus reverse transcriptase and also encodes the IN protein needed for viral integration into cell DNA.

The "env" or envelope region of a retrovirus genome codes for the envelope proteins. For the purpose of this invention, the "env " gene is to include not only the naturally occurring env sequence from a virus, but also modifications to the env gene, such as env genes that are modified to alter target specificity of retrovirus or alternative env genes that are used to generate "pseudotyped" retrovirus. Preferred env genes for use in this invention include, but are not limited to amphotropic env, murine xenotropic env, Gibbon Ape Leukemia virus (GaLV) env and the VSV-G protein-encoding gene.

The terms "polypeptide", "peptide" and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified; for example, disulfide bond formation, glycosylation, lipidation, acetylation, phosphorylation, or any other manipulation, such as conjugation with a labeling component.

The "biochemical function" or "biological activity" of a polypeptide includes any feature of the polypeptide detectable by suitable experimental investigation. "Altered" biochemical function can refer to a change in the primary, secondary, tertiary, or quaternary structure of the polypeptide; detectable, for example, by molecular weight determination, circular dichroism, antibody binding, difference spectroscopy, or nuclear magnetic resonance. It can also refer to a change in reactivity, such as the ability to catalyze a certain reaction, or the ability to bind a cofactor, substrate, inhibitor, drug, hapten, or other polypeptide. A substance may be said to "interfere" with the biochemical function of a polypeptide if it alters the biochemical function of the polypeptide in any of these ways.

A "fusion polypeptide" is a polypeptide comprising regions in a different position in the sequence than occurs in nature. The regions may normally exist in separate proteins and are brought together in the fusion polypeptide; or they may normally exist in the same protein but are placed in a new arrangement in the fusion polypeptide. A fusion polypeptide may be created, for example, by chemical synthesis, or by creating and translating a polynucleotide in which the peptide regions are encoded in the desired relationship.

An "isolated" polynucleotide, polypeptide, protein, antibody, nucleic acid, oracid, or other substance refers to a preparation of the substance devoid of at least some of the other components that may also be present where the substance or a similar substance naturally occurs or is a purification technique to enrich it from a source mixture. Enrichment can be measured on an absolute basis, such as weight per volume of solution, or it can be measured in relation to a second, potentially interfering substance present in the source mixture. A substance can also be provided in an isolated state by a process of artificial assembly, such as by chemical synthesis or recombinant expression.

A polynucleotide used in a reaction, such as a probe used in a hybridization reaction, a primer used in a PCR, or a polynucleotide present in a pharmaceutical preparation, is referred to as "specific" or "selective" if it hybridizes or reacts with the intended target more frequently, more rapidly, or with greater duration than it does with alternative substances. Similarly, a polypeptide is referred to as "specific" or "selective" if it binds an intended target, such as a ligand, hapten, substrate, antibody, or other polypeptide more frequently, more rapidly, or with greater duration than it does to alternative substances. An antibody is referred to as "specific" or "selective" if it binds via at least one antigen recognition site to the intended target more frequently, more rapidly, or with greater duration than it does to alternative substances. A polynucleotide, polypeptide, or antibody is said to "selectively inhibit" or "selectively interfere with" a reaction if it inhibits or interferes with the reaction between particular substrates to a greater degree or for a greater duration than it does with the reaction between alternative substrates.

A "cell line" or "cell culture" denotes higher eukaryotic cells grown or maintained in vitro. It is understood that the descendants of a cell may not be completely identical (either morphologically, genotypically, or phenotypically) to the parent cell.

The term "primate" as used herein refers to any member of the highest order of mammalian species. This includes (but is not limited to) prosimians, such as lemurs and lorises; tarsioids, such as tarsiers; new-world monkeys, such as squirrel monkeys (*Saimiri sciureus*) and tamarins; old-world monkeys such as macaques (including *Macaca nemestrina*, *Macaca fascicularis*, and *Macaca fuscata*); hylobatids, such as gibbons and siamangs; pongids, such as orangutans, gorillas, and chimpanzees; and hominids, including humans.

"Mean residence time" is the average amount of time the culture medium remains in contact with the producer cells during the production phase. The optimal mean residence time is determined by the following considerations: 1) cell specific vector production rate; 2) rate of vector inactivation; 3) cell specific nutrient uptake rates; 4) cell specific metabolite production rates; 5) temperature; 6) volumetric cell density; and 7) the target cells for which the vector supernatant is intended. Given a volumetric producer cell density of $\geq 1 \times 10^6$ cells/ml, the optimal mean residence time ranges from 3 to 6 hours with PA317-based cultures; from 6 to 12 hours with ProPak-A-based cultures; and 12 to 24 hours with ProPak-X or PG13-based cultures. These mean residence times are based upon maximal transduction of cell lines.

DESCRIPTION OF EMBODIMENTS

This invention provides a method for obtaining a safe recombinant retroviral packaging cell capable of producing retroviral-based vectors and retroviral vector supernatant. The method comprises the steps of selecting a retrovirus that will provide the retroviral env and gag-pol oligonucleotide sequences for the recombinant production of retroviral env and gag-pol gene products and obtaining a eukaryotic cell free of endogenous related retroviral nucleic acids or oligonucleotides of the same retroviral type. Although any retrovirus can be suitably used in the method of this invention, the use of the murine leukemia virus (MLV) is presently described. Thus, if any of gag, pol or env genes are to be derived from a MLV, the candidate packaging cell should be screened for absence of endogenous MLV retroviral nucleic acid and those sequences closely related to MLV which, by recombination, would produce replication competent retrovirus.

The env gene product determines the target cell specificity of the recombinant retrovirus particle and will, therefore, be selected to provide optimal transduction of the target cells of interest. Env may be the MLV amphotropic Env or any envelope capable of combining to form infectious "pseudotyped" retrovirus particles. For example, MLV amphotropic and murine xenotropic retroviral vectors are known to transduce human cells. Other env genes of interest include those from Gibbon Ape Leukemia Virus (GaLV), RD114, FeLV-C, FeLV-B, BLV, and HIV-1. See PCT Publication No. WO 92/14829 (page 25, line 1 through 1 through page 34, line 1). In addition, the env gene can be modified to more specifically target the recombinant retrovirus to the target cell of interest. For, example, the Env protein may be modified by combination with an antibody binding site specific for a cell surface antigen on the target cells of interest, e.g. an anti-CD34 antibody for targeting to hematopoietic stem and progenitor cells (Cossett et al. (1995) *J. Virol.* 69:6314–6322 and Kasahara, et al. (1994) *Science* 266:1373–1376). The env gene can also be modified so as to broaden the cell tropism of the virus, for e.g. by constructing a chimeric env that can bind to both amphotropic and xenotropic receptors or to a unique receptor on cells. In one embodiment, a chimeric amphotropic/xenotropic envelope gene, Eax, was constructed as described in Examples 6 and 7. Vector particles with a Eax envelope displayed dual cell tropism and will therefore transduce a broader range of target cells.

For clinical gene therapy applications it is important that the retroviral vector sequences and structural gene sequences be designed to minimize recombination to form replication competent retrovirus (RCR). By introducing the gag-pol and env gene sequences into the packaging cell separately so that they integrate in different areas of the packaging cell genome, the rate of RCR formation is decreased since multiple recombination events are required to generate RCR. Nevertheless, RCR are sometimes found in recombinant retroviral vector preparations. One possible reason is the presence of endogenous retroviral sequences in the murine cells (NIH/3T3) that the most commonly used packaging cell lines are based on, which may recombine with the introduced retroviral sequences. Therefore, the safe packaging cells of the present invention are generated from a eukaryotic cell line lacking endogenous retroviral sequences which would be capable of producing RCR by recombination with introduced retroviral sequences.

Thus, in one embodiment, the packaging cells of the present invention are derived from a cell line having no detectable endogenous retroviral sequences related to MLV. In addition, as described in the Examples herein, the cell line is preferably screened for the ability to stably secrete Gag-Pol and Env proteins and to efficiently transduce target cells rather than to produce high end-point titers alone. Preferably the eukaryotic cell line will be a non-murine cell line, more preferably a primate cell line, and most preferably a human cell line. The inventors have found that human 293 cells are free of retroviral sequences related to MLV, and when used as the basis for stable packaging cells, are able to produce high transduction efficiency retroviral vectors.

A cell free of related retroviral nucleic acid is obtained by screening a candidate cell for endogenous retroviral nucleic acid using methods well known to those of skill in the art and exemplified below. For example, several available cell lines such as the *Mus dunni* tail fibroblasts (see Lander and Chattopadhyay (1984) *J. Virol.* 52:695–698) are reportedly free of endogenous retroviral nucleic acid and thus, are suitably used in the methods disclosed herein. Alternatively, one of skill in the art can determine if the cell line contains endogenous retroviral nucleic acid by isolating a nucleic acid sample from the candidate cell line and probing for the endogenous DNA or RNA using methods such as traditional Southern and Northern hybridization analysis or the polymerase chain reaction ("PCR"), using retroviral specific probes, and when available, commercially available PCR kits (Invitrogen, San Diego, Calif.). Southern and Northern hybridization analyses are described, for example in Sambrook et al. (1989) infra. PCR methods are described in *Gene Expression Technology*, Goeddel, et al. eds., Academic Press, Inc. New York (1991). A cell is free of endogenous related retroviral nucleic acid if no hybridization is detected, even at low stringency conditions of 500 mM sodium ions, or if the primer used for the PCR analysis does not provide amplified nucleic acid. Preferably highly conserved sequences spanning viral LTR, packaging sequence and gag-pol gene regions are used as probes.

The candidate eukaryotic cell is of any suitable type, i.e., murine, non-murine, mammalian, primate, canine and human, provided that the cell line lacks endogenous retroviral sequences, grows well in culture, can be transfected or transduced with the appropriate gag-pol and env expression constructs and can express the viral proteins. The candidate cell line is preferably primate, and most preferably human. It has been found that primate and preferably human-based packaging cells can be used to produce retroviral vectors resistant to human complement.

In addition, the method further comprises using minimal gag-pol and env sequences to further decrease the chances of recombination to produce RCR. A minimal gag-pol open reading frame (ORF) and minimal env ORF are obtained from the selected retroviruses. The minimal ORF of the retroviral sequences are defined to include only those retroviral sequences from the ATG through the stop codon of the gene with no flanking sequences. Fragments of the gene as well as biological equivalents thereof also can be used provided that functional protein is produced when introduced into the candidate packaging cell line. In one embodiment, isolated retroviral nucleic acid coding for the minimal gag-pol and env ORF is selected for use. In a preferred embodiment, the nucleic acid is selected from MLV and the minimal sequences are determined to consist of nucleotides from about 621 to 5837 (gag-pol) (numbering from Shinnick et al. (1981)) and about nucleotides 37 to 2000 (env) (numbering from Ott et al. (1990). These nucleotide positions will vary with different MLVs. It should be understood, although not always explicitly stated, that nucleic acid sequences or molecules that are "equivalent" are determined to produce the same phenotypic effect as the isolated minimal ORF described herein, can be utilized as the minimal ORF sequences in the methods described herein. For example, altered, but phenotypically equivalent nucleic acid molecules are referred to as "equivalent nucleic acids".

The minimal gag-pol and env ORF nucleic acid molecules can be isolated using the technique described in the experimental section described below or replicated using PCR (Perkin-Elmer) and published sequence information. For example, the sequence can be replicated by PCR (Perkin-Elmer) which, in combination with the synthesis of oligonucleotides, allows easy reproduction of DNA sequences. The PCR technology is the subject matter of U.S. Pat. Nos. 4,683,195, 4,800,159, 4,754,065, and 4,683,202 and described in *PCR: The Polymerase Chain Reaction* Mullis et al. eds., Birkhauser Press, Boston (1994) and references cited therein. As is apparent to those of skill in the art, modifications and/or additions to the viral sequences are made to facilitate isolation and expression of the amplified DNA.

It is conceived that amphotropic and xenotropic cell lines are produced by this method and is determined by the selection of the env gene. Thus, the selection of the gag-pol and env gene are not restricted to isolation from the same virus, or the same virus type. An example of an amphotropic-producing packaging cell line produced by this method is ProPak-A and an example of a xenotropic packaging cell line, also produced by this method, is ProPak-X.

Thus, the invention further provides the isolated genes operatively linked to a promoter of RNA transcription, as well as other regulatory sequences for replication and/or transient or stable expression of the DNA. To minimize the chance of RCR it is preferred to avoid using extraneous viral sequences. The term "operatively linked" is defined above.

The promoter may be a minimal MLV-LTR, and is preferably "heterologous" to the retroviral gene. Suitable promoters are those that drive stable, high-level expression of gag-pol and env. Examples of suitable promoters include, but are not limited to, the cytomegalovirus immediate early (CMV) promoter, Rous Sarcoma Virus (RSV) LTR, *Moloney murine* leukemia virus (MMLV) LTR, or other viral LTR sequences. Vectors and plasmids which contain a promoter or a promoter/enhancer, with termination codons and selectable marker sequences, as well as a cloning site into which an inserted piece of DNA can be operatively linked to that promoter, are well known in the art and commercially available. To minimize the chance of RCR formation, gag-pol and env genes are preferably incorporated into separate expression plasmids and the plasmids introduced sequentially into the eukaryotic host cells. In plasmid amplification, the bacterial host cells are propagated at temperatures in the range from about 28° C. to about 32° C. and more preferably at about 30° C., to prevent recombination of viral sequences carried on the plasmids and to maintain the integrity of the plasmids.

The separate expression plasmids containing the retroviral gag-pol and env genes are then introduced in separate, sequential steps into the candidate packaging cells by techniques well known to those of skill in the art, such as calcium phosphate precipitation, electroporation and lipofection (Sambrook et al. (1989) supra). The insertion technique also can involve the use of a modified integrase enzyme that will recognize a specific site on the target cell genome. Such-site specific insertion allows the genes to be inserted at sites on host cells' DNA that will minimize the chances of insertional mutagenesis, minimize interference from other host cellular sequences, and allow insertion of sequences at specific target sites so as to reduce or eliminate the expression of undesirable genes.

Introduction of gag-pol and env genes can be done in either order. After insertion and integration of the gag, pol and env genes, the cells are screened for retroviral gene expression. If a selectable marker gene, such as antibiotic resistance, was used in combination with the retroviral sequences, the population can be enriched for cells for expressing the selectable marker (and therefore the retroviral genes) by growing the candidate cells in the presence of the antibiotic. Cells which survive and propagate will contain both the antibiotic resistance gene and the retroviral sequences. Still further, an ELISA with the appropriate antibody to a product of the expressed sequences will be a simple and quick assay to determine whether and to what extent the cells contain and express the retroviral genes.

Thus, the invention also provides an ELISA method to screen for expression of retroviral genes in candidate packaging cells to identify a retroviral packaging cell capable of producing recombinant, transducing retroviral vector particles. In particular, the ELISA will be used to screen for production of retroviral structural proteins such as Gag, Pol and Env. The ELISA method of the invention can also have diagnostic use in patients who have undergone gene therapy.

In one specific embodiment, Env protein is detected in a sandwich ELISA assay using an antibody from hybridoma 83A25 as primary antibody, to capture the protein. The captured protein is then detected using as secondary antibody, antiserum 79S-834, followed by an enzyme-conjugated antispecies antibody and the substrate for the enzyme. In a similar manner, Gag is detected separately using as primary antibody, an antibody from hybridoma R187 followed by antiserum 77S-227, enzyme-conjugated antispecies antibody and enzyme substrate. The primary antibody can be provided in the form of hybridoma culture supernatant, ascites or purified antibody. The anti-species antibody is preferably conjugated to a label such as an enzyme. Suitable enzymes include horeseradish peroxidase and alkaline phosphatase. The appropriate substrate to the particular enzyme is used. This particular embodiment of the ELISA assay is described in detail in the Examples below.

Preferably, the candidate packaging cell lines are further screened for the ability to produce vector supernatant having high transduction efficiency. Transduction efficiency is measured by the ability of the vector supernatant to transduce a target cell population. The target cell population can be human 293 cells, NIH/3T3 cell or primary cells. This invention also provides recombinant packaging cells obtained by the method described above. The recombinant packaging cell lines are an improvement over prior art packaging cell lines because, when transduced with a suitable retroviral vector and propagated, the cell lines of this invention produce a retroviral titer having high transduction efficiency. Thus, the cell line of this invention is characterized by producing viral supernatant that is resistant to human complement; has a high transduction efficiency; and is substantially free of RCR after continuous culture of more than 2 weeks and up to at least 12 weeks. As used herein, "transduction efficiency" refers to the percentage of the inoculated target cell population which has been marked with the vector. Gene marking can be measured by determining the fraction of cells which have integrated proviral vector (eg. by PCR) or by determining the fraction of cells expressing the transgene (eg. by FACS analysis). A recombinant retrovirus preparation (e.g., supernatant or supernatant concentrate) that has high transduction efficiency will produce an increased percentage of inoculated target cells that have been marked with the viral vector. Packaging cells of the present invention are able to produce recombinant retroviral supernatants capable of higher transduction efficiency than standard murine, PA317 cells as assayed on NIH/3T3 cells, and particularly as assayed on human 293 or primary cells. Suitable reagents and methods for performing this analysis are provided in the experimental section below.

Also provided herein is a method of producing retroviral vector supernatant comprising transducing the novel packaging cells produced according to the method described above with a suitable retroviral vector to generate producer cells. This invention further provides the retroviral supernatant so produced. In addition to the gene of interest to be delivered to the host cell, the retroviral vector will contain the "packaging signal" that allows the retroviral vector nucleic acid to be packaged in the vector particle in the recombinant packaging cell line, and the long terminal repeat that allow the vector nucleic acid to become effectively integrated into the target cell genome. The LTRs are positioned at either end of the proviral nucleic acid and also generally contain regulatory sequences such as promoter/enhancers that affect expression of the therapeutic or marker gene of interest. The gene or genes of interest also can be operably linked to a suitable promoter which can be constitutive, cell-type specific, stage-specific and /or modulable. Enhancers, such as those from other virus, can also be included.

In a separate embodiment, the retroviral vectors can contain genes coding for selectable and/or detectable markers that facilitate isolation of transduced cells. In other embodiments, it may be desirable for the vector to include a "suicide gene" that allows recipient cells to be selectively eliminated at will. Isolation, insertion and use of such markers and suicide genes are well known to those of skill in the art as exemplified in PCT Publication Nos. WO 92/08796 and WO 94/28143.

Prior art methods to improve gene transfer (transduction) efficiency with retroviral vectors often focused on increasing the end-point titer. The evidence presented herein does not support a correlation between end-point titer and transduction efficiency. The evidence presented herein also does not support the conclusion that increasing end-point titer necessarily increases transduction efficiency because non-transducing particles interfere with transducing virions and reduce transduction efficiency without reducing-end point titer. Indeed, the evidence shows that packaging cell line clones should be screened for ability to generate supernatant based on transduction efficiency rather than on end-point titers.

Thus, the invention further provides a method of producing retroviral vector supernatant having higher transduction efficiency which is more suitable for gene therapy, comprising culturing producer cells in a packed-bed bioreactor having a surface to volume ratio of about 5 to 50 cm$^2$/ml, culturing the producer cells population at a temperature of around 30° C. to about 37° C. and harvesting supernatant produced by said producer cells at such time as the transduction efficiency of the supernatant is optimal for a target cell, thereby obtaining a high transduction efficiency supernatant.

As used herein, a packed-bed bioreactor refers to a cell culture vessel comprising a bed matrix in which cells grow in a confined three-dimensional space. Reactor volume size, and volume of packed-bed matrix can vary depending on the quantity of retroviral supernatant required.

The matrix which comprises the packed-bed has the following properties:

1) The matrix is made of a material which allows for the attachment and growth of anchorage-dependent cells. The material can also be surface-coated or surface-treated to achieve this quality; 2) The matrix can entrap cells normally cultured in suspension so as to confine them to a three-dimensional space; 3) The matrix has a large surface area to volume ratio (5 to 50 cm$^2$/ml), enabling cells to grow to high volumetric densities ($10^6$ to $10^8$ cells/ml). This property ensures a high volumetric vector production. In a specific embodiment, the surface to volume ratio is from about 20 to about 30 cm$^2$/ml and preferably is about 24 cm$^2$/ml; 4) The matrix has a large void volume when packed to minimize the pressure-drop across the bed during operation. A negligible pressure drop ensures an even supply of nutrients to cells throughout the bed.

The bioreactor is available commercially and the bed matrix can be packed separately. Preferably, the bed matrix is constructed such that the pressure drop across the bed matrix is in the range of 0–0.25 mbar/cm. Ideally, the pressure drop is negligible.

It is intended that any retroviral producer cell line can be cultured in the packed-bed bioreactor. However, the producer cells derived from the packaging cell lines produced according to the above method are particularly well suited for use in this method to produce retroviral vector supernatants. Such cells include, but are not limited to, producer cells derived from 3T3 or 293 cells. Examples of 3T3 and 293-based producer cell lines are those based on the PA317, GP-Am12, CRIP, PG13, ProPak-A and ProPak-X packaging cell lines.

After seeding of producer cells into the packed-bed reactor, cells can be cultured at temperatures ranging from 30° to 37° C. Preferably, the cells will be initially cultured at 37° C. to allow for maximal cell growth. Once the culture achieves a high cell density ($10^6$ cells/ml or greater), the temperature can be lowered to 32° during the production phase to minimize the loss of transducing vector due to thermal inactivation. The temperature selected for the production phase will depend on the following variables: temperature differences in the cell specific vector production rate; the rate of vector inactivation at a given temperature; cell density; and the rate at which the vessel is perfused with fresh medium.

The time to harvest the retroviral supernatant to obtain optimal transduction efficiency will vary with the parental cell type of the producer cells. "Mean residence time" and "transduction efficiency" are defined above. Optimal transduction efficiency for a retroviral supernatant refers to the highest percentage of the inoculated target cell population that is marked with the viral vector, obtained under the culture conditions tested. If the producer cells are derived from PA317 cells, the supernatant can be harvested after a mean residence time of from 2 to 12 hours starting from the time the producer cells reach a cell density of at least $10^6$ cells per ml. For human 293-derived producer cells, the supernatant is harvested after a mean residence time of from 1 to 24 hours, usually from 6 to 24 hours. Mean residence time can be decreased as cell density increases.

The packed-bed bioreactor can be operated in a fed-batch or perfusion mode. Fed-batch operation refers to the changing of a part or all of the culture medium at discrete time intervals. Perfusion mode refers to the continual supply of fresh medium at a specified perfusion rate which is equivalent to the rate at which vector supernatant is continually harvested. The perfusion mode of operation is preferred as it maintains a more stable culture environment, yielding less stress on the producer cells. Depending on the producer cell line and the volumetric cell density, the optimal perfusion rate can vary from 1 reactor volume per day to 24 reactor volumes per day. Preferably, the perfusion rate is from 2–12 reactor volumes per day, even more preferably at 2–6 reactor volumes per day, and most preferably, at a constant rate of about 4 reactor volumes per day. In the most preferred embodiment, the perfusion rate increases proportionally to the cell density. The cell density can be monitored indirectly by nutrient consumption, metabolite production, or preferably, by oxygen uptake. The optimal perfusion rate, for a given producer cell line at a given volumetric cell density, is established by determining the mean residence time of the culture medium required to produce a vector supernatant which yields the maximum transduction efficiency of the target cell population.

The cell culture conditions and parameters described above are also applied to a method of producing retroviral supernatant having high transduction efficiency, from non-murine derived producer cells. After seeding in the packed-bed bioreactor, the cells can be continuously cultured at 37° C. or 32° C. Alternatively, the cells are initially cultured at 37° C. until the cells produce a confluent monolayer, and are thereafter cultured at 32° C. The producer cells derived from the non-murine packaging cell lines produced according to the above method are particularly suited for use in this method for obtaining vector supernatant. Such cells include, but are not limited to producer cells derived from 293 cells, HT1080 cells and D17cells. In one particular embodiment, the non-murine producer cells are derived from 293 cells and the retroviral supernatant is harvested after a mean residence time of from 6 to 24 hours, starting from the time the producer cells reach a cell density of at least $10^6$ cells per ml.

To achieve maximal producer cell densities in the packed-bed bioreactor, proper aeration of the vessel is important. It has been noted that with sufficient oxygen transfer, supernatants with higher transduction efficiencies are obtained. Aeration conditions providing air saturation greater than 20%, preferably between 20% and about 60% are necessary to achieve efficient vector production. Most preferred are aeration conditions providing greater than 40% of air saturation.

One of skill in the art can easily determine the most suitable culture medium for the cells using commercially available basal medium and supplementing the medium as provided by the art. Cells can be cultured in the medium supplemented with fetal bovine serum (FBS), and vector supernatants produced in the presence of FBS. However, for clinical use, serum-free medium is preferred. To achieve this, cells can be initially expanded and grown in the packed-bed bioreactor in medium supplemented with FBS, and switched to a serum-free medium formulation for the production of serum-free vector supernatants. Most preferably, cells will be cultured and vector supernatants produced in serum-free media starting with cells derived from a serum-free master cell bank.

The disclosed method also can be utilized to produce retroviral vector supernatant having high transduction efficiency by seeding primate producer cells in a packed-bed bioreactor. Suitable primate producer cells include those derived from 293 cells, ProPak-A and ProPak-X cells. When the producer cell is derived from a 293 cell, it is preferable to harvest the retroviral supernatant when the culture medium's mean residence time in the reactor is about 6–24 hours, starting from the time the producer cells reached a cell density of at least $10^6$ cell per ml.

The invention further provides a method of obtaining high transduction efficiency MLV-based retroviral supernatant suitable for gene therapy, comprising culturing human-derived producer cells under the conditions described above. Human-derived producer cells are seeded in a packed-bed bioreactor having a surface area to volume ratio of about 5 to 50 $cm^2/ml$, at a concentration starting from about 2 to $3 \times 10^4$ cells/$cm^2$, under constant perfusion, with aeration sufficient to maintain the culture medium at about 20% to 60% air saturation, preferably at or greater than 40% air saturation. The cells are cultured at a temperature of about 37° C. until they grow to a cell density of at least $10^6$ cells per ml whereupon the temperature is then lowered to 32° C. Retroviral supernatant is then collected after an additional 6 to about 24 hours of incubation time. Human cells useful in this method include, but are not limited to those derived from 293 cells, HT 1080 cells, ProPak-A cells and ProPak-X cells.

The present method of producing retroviral vector supernatants also encompasses co-culturing of two or more producer cell lines under the conditions described above. In this circumstance, the packed-bed bioreactor is seeded with two or more different producer cell lines, preferably containing the same vector and having complementary tropisms, e.g. producer cells derived from human amphotropic and xenotropic packaging cell lines. This co-culture technique results in an amplification of vector copy number within the producer cells, and yields vector supernatants which contain a mixture of retroviral vector particles targeted to distinct receptors expressed on most human cells.

The culture supernatant produced by the methods described herein is also within the scope of this invention. The supernatant has been shown to transduce cells, and in particular, stem cells very efficiently.

Prior to transduction, the stem cells are isolated and selected. Methods of isolating and selecting cells are well known in the art. For example, sorted $CD34^+Thy1^+Lin^-$ cells from either adult bone marrow (ABM) or mobilized peripheral blood (MPB) are used. $CD34^+Thy1^+Lin^-$ are highly enriched in human hematopoietic stem cells. See. U.S. Pat. No. 5,061,620.

Various methods can be used to isolate stem cells. For the purpose of illustrating one method of preparing stem cells from ABM, 20 mL of fresh bone marrow can be isolated by aspiration of the iliac crest from normal human volunteers. Marrow is separated by taking the mononuclear cell fraction following a Ficoll-Perque separation, positive-selected for $CD34^+$ cells according to the method described by Sutherland et al. (1992) Exp. Hematol. 20:590. Briefly, cells are resuspended in staining buffer (SB) (HBSS containing 10 mM HEPES, 2% heat-inactivated FCS) at $5 \times 10^7$ cells/mL. QBEND10 (anti-CD34) (Amac, Westbrook, Me.) is added at $\frac{1}{100}$ dilution, and then the cells are incubated on ice for 30 min. Cells are then washed in SB with a FCS underlay, and resuspended at $4 \times 10^7$/mL in SB. An equal volume of washed Dynal sheep anti-mouse $IgG_1Fc$ magnetic beads (Dynal, Oslo, Norway), is added at a 1:1 bead to cell ratio, to give a final cell concentration of $2 \times 10^7$ cells/mL. After 30 min incubation on ice, with gentle inversion, the tube was placed against a Dynal magnet (Dynal) for 2 minutes, and $CD34^-$ cells removed. Following two washes, 20 mL of 'glycoprotease' (O-sialoglycoprotein endopeptidase, Accurate Chemical, Westbury, N.Y.) plus 180 mL of RPMI (JRH Biosciences)/20% FCS is added and the beads incubated at 37° C. for 30 min to cleave the QBEND10 epitope, and release $CD34^+$ cells from the beads. Beads are then washed three times to maximize cell recovery. The glycoprotease used for the release step in the positive selection procedure has been shown not to effect subsequent ex vivo expansion of progenitors (Marsh et al. (1992) Leukemia 6:926).

Mobilized peripheral blood (MPB) samples can be obtained with informed consent from multiple myeloma patients. Patients are treated on day 1 with cyclophosphamide at 6 g/m (1.5 g/m² every 3 hours×4 doses). From day 1 until the start of leukopheresis (usually 10–28 days), granulocyte macrophage colony stimulating factor (GM-CSF) is given at 0.25 mg/m²/day. Apheresis for total white cells is started when the peripheral blood white cell count is greater than 500 cells/ml and the platelet count is greater than 50,000 cells/ml. Patients are apheresed daily until from $6 \times 10^8$ mononuclear cells (MNC) are collected.

Fresh MPB samples are then elutriated with a JE5.0 Beckman counterflow elutriator equipped with a Sanderson chamber (Beckman, Palo Alto, Calif.). Cells are resuspended in elutriation medium (Biowhittaker, Walkersville, Md.) at pH 7.2, supplemented with 0.5% human serum albumin (HSA). The rotor speed is set at 2000 RPM, the cells are introduced, and the first fraction collected at a flow rate of 9.6 ml/min. Fractions 2 and 3 are collected at the respective flow rates of 14 and 16 ml/min. The larger cells remaining in the chamber are collected after stopping the rotor. Cells are resuspended in RPMI supplemented with 5% HSA, 10 mg/ml DNAse I and penicillin/streptomycin at 50 U/ml and 50 mg/ml, respectively. Fractions 2 and 3 are pooled and incubated with 1 mg/ml heat-inactivated human gamma-globulin to block non-specific Fc binding. Granulocytes are further depleted by incubation with CD15 conjugated to magnetic beads (Dynal M450, Oslo, Norway) followed by magnetic selection.

$CD34^+Thy1^+Lin^-$ cells are isolated from ABM and MPB by flow cytometry as follows. Antibodies to CD14 and CD15 were obtained as FITC conjugates from Becton-Dickinson. Antibodies to Thy-1 (GM201) can be obtained from a commercial source or prepared and detected with anti-IgG1-PE conjugate from Caltag. Antibody to CD34 (Tük 3) also can be commercially obtained and detected with an anti-IGg3-Texas Red conjugate (Southern Biotechnologies).

Anti-CD34 antibody or an IgG3 isotype matched control is added to cells in staining buffer (HBSS, 2% FCS, 10 mM HEPES) for 20 minutes on ice, together with anti-Thy-1 antibody at 5 µg/ml. Cells are washed with a FCS underlay, and then incubated with Texas Red conjugated goat anti-mouse IgG3 antibody and phycoerythrin-conjugated goat antimouse IgG1 antibody for 20 minutes on ice. Blocking IgG1 is then added for 10 minutes. After blocking, the FITC-conjugated lineage antibody panel (CD14 and CD15) is added, and incubated for another 20 minutes on ice. After a final washing, cells are resuspended in staining buffer containing propidium iodide (PI).

Cells are sorted on a Vantage cell sorter (Becton Dickinson) equipped with dual argon ion lasers, the primary laser emitting at 488 nm and a dye laser (Rhodamine 6G) emitting at 600 nm (Coherent Innova 90, Santa Cruz, Calif.). Residual erythrocytes, debris and dead cells are excluded by light scatter gating plus an FL3 (PI) low gate. The sorted cell population is diluted 1:1 in HBSS, pelleted, and resuspended in HBSS for hemocytometer counting.

For transduction, the sorted cells are suspended in fresh or freshly thawed retroviral supernatant diluted in appropriate media containing cytokines. Cells and vector are then centrifuged and resuspended and cultured in cytokine-enriched media for about three days. For culturing CD34+ hematopoietic stem or progenitor cells, the cytokines are preferably a combination including, but not exclusively, IL-3, IL-6, LIF and SCF. After three days, the cells are harvested and used to determine bulk transduction frequency as described below. Alternatively, the cells can be introduced into a patient by methods well known to those of skill in the art for gene therapy.

Further provided by the invention is a method of increasing the gene transduction efficiency of a cell by transducing target cells with a retroviral vector supernatant derived from one or more recombinant packaging cells produced by the methods of the present invention. Preferably, the target cell is a primary hematopoietic cell such as a stem cell. In a specific embodiment, the retroviral supernatant is derived from the culture of ProPak-A.6 or ProPak-A.52 and ProPak-X. The transduction efficiency of a cell population can also be increased by inoculating or transducing a target cell population with vector particles of more than one tropism. This is achieved by transducing the cells with a vector particle having a modified envelope protein as described above, wherein the envelope protein can bind to more than one receptor. Examples 6 and 7 below provide transduction of target cells with a vector particle having a chimeric amphotropic/xenotropic envelope encoded by the Eax env gene. Alternatively, the cells are simultaneously transduced with vector supernatants containing particles of complementary tropisms, eg. amphotropic and xenotropic vector supernatants, mixed into a single inoculum. The inoculum containing vector supernatants of different tropisms can be prepared by mixing the two supernatants obtained from their respective, separately cultured producer cells, or the two complementary producer cell lines can be co-cultured to produce a single supernatant containing the two types of vector particles. In a co-culture, a production vessel, preferably a packed-bed bioreactor, is seeded with a mixture of producer cells with complementary tropisms that produce vector particles which are capable of transducing human cells.

In one embodiment of the present invention, cells are transduced with a retroviral supernatant produced from the co-culture of a ProPak-A and a ProPak-X producer cell line, specifically, ProPak-A.52.LMiLy and ProPak-X.LMiLy. The co-culture of ProPak-A and ProPak-X producer cells have the advantage that they do not produce RCR. Close to 100% gene transfer was achieved using such co-culture supernatants on MPB-derived CD34+ cells.

Yet another aspect of the invention is a method of producing a packaging cell line capable of expressing more than one envelope protein with tropism for human cells, e.g. amphotropic and xenotropic envelope proteins. This packaging cell line is derived by introduction of expression plasmids for other envelope genes into an existing packaging cell line. For example, ProPak-A.6 cells can be transfected with the expression plasmid pCI-Ex and cell clones isolated which secrete vector particles that transduce quail cells or other cells which are transduced by xenotropic particles but not by amphotropic particles. Such multitropism particles would be expected to transduce target cells with higher efficiency in the situation where the target cells express the individual receptors but at concentrations too low to allow stable vector-cell complex formation by the pure amphotropic or xenotropic particles.

The following examples are intended to illustrate, not limit the scope of the invention disclosed herein.

Experimental

As noted above, successful retroviral-mediated gene therapy requires safe and efficient packaging cell lines for vector particle production. Existing packaging lines for murine leukemia virus-based vectors are predominantly derived from NIH/3T3 cells which carry endogenous murine viral sequences which could participate in recombination to form replication competent retrovirus (RCR), thereby rendering them unsafe. Provided herein are methods for constructing safe and efficient retroviral packaging cell lines for vector particle production as well as the cell lines so obtained.

Materials and Methods

Unless otherwise stated, materials and reagents are prepared and methods are conducted, as set forth below. Producer cell lines are named by noting the packaging cell line and inserted vector. For example, PA.SVNLZ denotes a producer cell line derived from packaging cell line PA317 carrying the vector SVNLZ. PP-A and PP-X denote ProPak-A and ProPak-X, respectively.

PA317-Based Cell Lines and Retroviral Vectors

The retroviral vector producer cell lines disclosed herein were generated from the amphotropic PA317 packaging cell line produced according to the methods of Miller and Buttimore, 1986) *Mol. Cell Biol.* 6:2895–2902. Producer cell lines, the GP+E86 packaging cell line produced according to the method of Markowitz, et al. 1988) *J. Virol.* 62:1120–1124, and NIH/3T3 cells (ATCC CRL1658) were cultured in Dulbecco's modified Eagle medium (DMEM) supplemented with 4.5 g/L of glucose, 4 mM L-glutamine and 5% Cosmic Calf Serum (CCS, Hyclone, Utah). The human epithelial carcinoma line HeLa (ATCC CCL2) was cultured in DMEM supplemented with 4.5 g/L of glucose, 4 mM L-glutamine and 10% fetal bovine serum (FBS, Hyclone, Utah). The human lymphoid cell line Jurkat was cultured in RPMI supplemented with 4.5 g/L of glucose, 2 mM L-glutamine, and 10% FBS. All cell lines were maintained in an incubator at 37° C. under 5% $CO_2$ unless otherwise stated.

Figure 2:
FIG. 2 shows the structure of several of the retroviral vectors used in this study. The name of each vector is indicated on the left. Open boxes represent the MLV LTR elements; RevM10, trans-dominant mutant of the HIV Rev protein; TK, Herpes Simplex virus-1 thymidine kinase promoter; Neo, neomycin phosphotransferase; SV, simian virus 40 early promoter; nls, nuclear localization signal; IRES, internal ribosomal entry site element; NGFR, nerve growth factor receptor; puro, puromycin resistance gene; CMV, CMV-IE promoter. LMiLy and LLySN encode the Lyt2 surface antigen expressed either directly from the retroviral LTR promoter in LLySN, or via an IRES element (ires) in LMiLy. LLySN contains the neomycin phosphotransferase gene (Neo) expressed from an internal SV40 promoter (SV).
Figure 2:
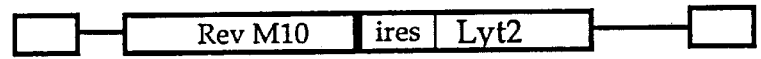
Figure 2:
Figure 2:
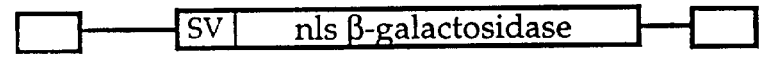
Figure 2:
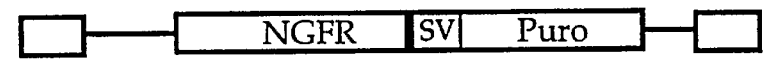
Figure 2:

The SVNLZ (see Bonnerot, et al. (1987) *Proc. Natl. Acad Sci. U.S.A.* 84:6795–6799) and LMTNL vectors are known in the art (See for example, Escaich et al. (1995) *Human Gene Therapy* 6:625–634). FIG. 2 sets forth a map of these vectors. The SVNLZ vector encodes the LacZ gene with a nuclear localization signal expressed from the simian virus 40 early promoter (FIG. 2). The LMTNL vector encodes a transdominant mutant of the HIV Rev protein (RevM10) expressed from the MMLV-LTR, and the neomycin phosphotransferase (neo) gene expressed from the thymidine kinase promoter (FIG. 2).

PA317 Culture Conditions

For vector production, PA317-based producer cells were seeded into culture vessels at a density of $3 \times 10^4$ cells/cm$^2$ unless otherwise noted. Once the cells had formed a confluent monolayer (approximately 3 days), the medium was changed and the temperature lowered from 37° C. to 32° C. Three types of culture vessels were used: (1) 75-cm$^2$ tissue culture flasks with filter caps (Costar, Cambridge, Mass.); (2) 900-cm$^2$ roller bottles with filter caps (Costar, Cambridge, Mass.); or (3) a 500 ml bench scale packed-bed bioreactor (New Brunswick Scientific, Edison, N.J.) with 10 g of Fibra Cell discs (12,000 cm$^2$). Samples from the bioreactor (1 ml) were removed with a sterile syringe through a sampling port. Supernatant samples were cleared of cellular debris by filtration through 0.45 μm nitrocellulose filters (Nalgene, Rochester, N.Y.), snap-frozen in methanol/dry-ice, and stored at −70° C. Frozen supernatants were thawed at 37° C. and kept on ice until assayed. All supernatants used in this study were free of replication competent retrovirus as determined by the S+L− assay on PG4 cells as described in Cornetta, et al. (1993) *Human Gene Therapy* 4:579–588 and Forestell et al. (1996) *J. Virological Methods* 60:171–178.

Assays for Retroviral Vectors

LacZ end-point titration

NIH/3T3 cells were plated into 24 well plates at $5 \times 10^4$ cells per well, and inoculated the next day with 0.2 ml of diluted vector supernatant ($10^{-1}$ to $10^{-6}$ dilution series) in the presence of polybrene (8 μg/ml). After three hours, the inoculum was aspirated and 0.5 ml of fresh medium added. Three days post inoculation, the cells were fixed with 0.5% glutaraldehyde and stained with X-gal using the protocol of Bagnis et al. (1993) *Oncogene* 8:737–743. The end-point titer (cfu/ml) was calculated by counting a statistically representative number of blue colonies in a well, multiplied by the dilution factor, and divided by the volume of the inoculum. All end-point titrations were performed in duplicate.

For the xenotropic vectors prepared using ProPak-X, titrations were performed using the same procedure except that human 293 cells were used as the target cells.

LacZ transduction efficiency

Cells were plated into 24 well plates at $5 \times 10^4$ cells per well, and inoculated the next day with 0.2 ml of a 1:1 dilution of vector supernatant with medium in the presence of polybrene (8 µg/ml). Three hours later, the inoculum was aspirated and 0.5 ml of fresh medium added. Transduction efficiencies were determined three days post-inoculation by flow cytometry using the FluoReporter lacZ detection kit (Molecular Probes, Inc., Eugene, Oreg.). For NIH/3T3 or 293 cells, the reaction with fluorescein di-β-D-galactopyranoside (FDG) was quenched after one minute with 1 mM phenethylthio-β-D-galactopyranoside (PETG). For Jurkat and HeLa cells, PETG was added after a one hour incubation on ice. Acquisition and analysis were performed using a Becton Dickinson FACScan and the LYSYS software package. Transduction efficiency was determined as the percentage of cells expressing the lacZ gene (green fluorescence intensity) above the basal fluorescence levels defined as that of non-transduced control cells.

G418 resistance end-point titer

Titrations were performed in 6 well plates seeded with $2.5 \times 10^4$ NIH/3T3 cells per well, and inoculated the next day with 1.0 ml of diluted vector supernatant ($10^{-1}$ to $10^{-6}$ dilution series). Three hours later, the inoculum was aspirated and 2.0 ml of fresh medium was added. One day after inoculation, G418 was added to each well at a final concentration of 0.7 mg/ml, and the medium was changed as required until individual colonies could be seen (typically 10 to 14 days). The end-point titer (cfu/ml), was calculated by counting a statistically representative number of G418 resistant colonies in a well and multiplied by the dilution factor.

For the xenotropic vectors prepared using ProPak-X, titrations were performed using the same procedure except that human 293 cells were used as the target cells.

G418 resistance transduction efficiency

Cells were seeded into 6 well plates at $1 \times 10^5$ cells per well. The next day, cells were inoculated with 1.0 ml of a 1:1 dilution of vector supernatant with medium in the presence of polybrene (8 µg/ml). Three hours later, the inoculum was aspirated and 2.0 ml of fresh medium was added. Three days post-inoculation, adherent cells were trypsinized and seeded into 6 well plates at a 10-fold dilution series from $10^5$ cells/well to 1 cell/well. Jurkat cells were plated in methylcellulose medium to allow individual colonies to be scored. Duplicate plates were seeded, and incubated in the presence or absence of G418. The percentage transduction efficiency was calculated as the number of G418-resistant colonies divided by the number of colonies that formed in the absence of G418, multiplied by 100.

The following methods relate to Examples 6–12.

Retroviral packaging cell culture

Packaging and producer cell lines were grown in Dulbecco's modified Eagle's medium (DMEM: JRH Biosciences, Lenexa, Kans.) supplemented with fetal bovine serum (FBS: HyClone Laboratories Inc., Logan, Utah) at either 5% (PA317 (Miller and Buttimore, (1986) *Mol. Cell. Biol.* 6: 2895–2902), PG13 (Miller et al., (1991) *J. Virol.* 65: 2220–2224)) or 10% (ProPak).

Expression Constructs and Retroviral Vectors

Gag-Pol and Env proteins were expressed from separate plasmids which, along with the retroviral vectors used in this study, are described in FIGS. 1 and 2. Methods are described herein for derivation and analysis of cells expressing MLV proteins, analysis of Gag-Pol and Env proteins in tissue culture supernatants, and titration of retroviral vectors encoding the Lyt2 antigen (Rigg et al. (1995) *J. Immunol. Meth.* 188: 501–509). A producer cell line and the respective retroviral vector supernatant are indicated by the cell name followed by a period and the name of the vector, e.g., ProPak-A.LLySN (Amphotropic), ProPak-X.LLySN (Xenotropic), PA317.LMiLy or PG13.LMiLy. Co-cultures of ProPak-X and ProPak-A-based producer cell lines are indicated with a slash, i.e. ProPak-A/X.LMiLy.

Vector Supernatant Production

Producer cells were seeded into culture vessels at a density of $3 \times 10^4$ cells/cm$^2$ or greater. Once the cells had formed a confluent monolayer (approximately 3 days), the medium was changed and the temperature lowered from 37° C. to 32° C. Thereafter, supernatant was harvested at 12 hour intervals. For supernatant production in T-flasks from pools of LLySN-carrying producer cells, medium was repeatedly harvested for up to 10 days at 32° C. Supernatants were then compared for their ability to transduce NIH/3T3 or 293 cell lines, and those supernatants that yielded the highest transduction were used in the studies reported here. Three types of culture vessels were used: (1) 75-, 162- or 225-cm$^2$ tissue culture flasks with filter caps (Costar, Cambridge, Mass.); (2) 900-cm$^2$ roller bottles with filter caps (Costar, Cambridge, Mass.); and (3) a 500 ml packed-bed bioreactor (New Brunswick Scientific, Edison, N.J.) with 10 g of Fibra Cell discs (12,000 cm$^2$). The bioreactor was seeded with $5 \times 10^5$ cells/ml and the medium was circulated by a marine-type impeller. Supplemental aeration was achieved by direct micro-sparging of a medical grade mix of air with 5% $CO_2$, and 0.01% Pluronic F-68 (Sigma, St. Louis, Mo.) was added to prevent cell damage from shear. Vector supernatants were cleared of cellular debris by filtration through 0.45 µm nitrocellulose filters (Nalgene, Rochester, N.Y.), snap-frozen in methanol/dry-ice, and stored at −70° C. Aliquots were thawed at 37° C. and kept on ice until use. All supernatants used for gene transfer experiments were free of replication-competent retrovirus (RCR) as determined by the extended S+L− assay on PG4 cells (Forestell et al., (1996) *J. Virol. Meth.* supra).

Inoculation Procedures

Unless otherwise stated, cells were inoculated with vector once at unit gravity for 3 h at 37° C. Inoculation under centrifugation, termed spinoculation, (Kotani et al., (1994) *Hum. Gene Ther.* 5: 19–28; Bahnson et al., (1995) *J. Virol. Meth.* 54: 131–143; Forestell et al., (1996) supra) was at 2550 g for 3 or 4 h. Polybrene (8 µg/ml) or protamine sulfate (4 µg/ml) was added to inocula for cells lines or primary cells, respectively.

Primary Hematopoietic Cell Purification

PBL were isolated from peripheral blood mononuclear cells as described (Rigg et al., (1995) supra) and depleted of CD8-positive cells. The CD34-positive (CD34+) fraction was isolated from mobilized peripheral blood (MPB) or adult bone marrow (ABM) with the Baxter Isolex affinity column (Baxter Healthcare, Deerfield, Ill.). Further purification to obtain the fraction carrying the Thy-1 antigen (CD34+/Thy+) was achieved by high-speed flow cytometric sorting, as described by Sasaki et al, (1995) *J. Hemat.* 4: 503–514). Hematopoietic stem and progenitor cells (HSPC) were cultured in a 1:1 mixture of IMDM and RPMI media containing 10% FBS, IL-3 and IL-6 (20 ng/ml each; Sandoz Pharma, Basel, Switzerland), and stem cell factor (SCF; Amgen Inc., Thousand Oaks, Calif.) or leukemia inhibitory factor (LIF; Sandoz) (100 ng/ml).

Transduction Efficiency Assays

Transduction efficiencies achieved with Lyt2-encoding vector supernatants were quantitated as the proportion of target cells that expressed Lyt2 antigen 2 or 3 days following inoculation (Rigg et al., (1995) supra). Integration of the RevM10 gene into HSPC clonogenic progeny was determined by PCR. Methylcellulose (Stem Cell Technologies, Vancouver, Canada) was supplemented with IL-3, IL-6, SCF, erythropoietin (Amgen, Thousand Oaks, Calif.) and granulocyte-macrophage colony stimulating factor (Immunex, Seattle, Wash.). Individual colonies of all lineages (CFU-C) were picked after 12 to 14 days culture in methylcellulose culture, and assayed for the revM10 gene in cellular DNA using a PCR assay as described in Plavec et al. (1996) *Gene Therapy* 3:723. Colonies were scored positive if both revM10 and β-globin sequences were detected.

EXAMPLE

1

Construction of Packaging Cells

To minimize the chance of recombination with endogenous viral sequences to form RCR, candidate cell lines were screened for endogenous retroviral, and in particular, endogenous MMLV nucleic acids. Genomic DNA from a variety of cell lines was analyzed by Southern blot hybridization by the method generally disclosed in Sambrook et al., (1989) *Molecular Cloning: A Laboratory Manual* 2nd ed., Cold Spring Harbor Laboratory, New York, using probes specific to retrovirus MMLV long terminal repeat (LTR) or MMLV gag-pol sequences. The following cell lines were screened: CHO cells which are used to produce recombinant proteins; Vero and MRC-5 cells in which vaccines are produced (WHO (1989) "Technical Report Series No. 786" WHO, Geneva), and human embryonic kidney 293 cells (ATCC CRL 1573) that are used to produce adenovirus vectors for clinical gene therapy applications and retroviral vectors (Pear et al. (1993) *Proc. Natl. Acad. Sci. U.S.A.* 90:8392–8396; Finer et al. (1994) *Blood* 83:43–50). *Mus dunni* tail fibroblasts (NIH) also were included since these cells are reportedly free of endogenous MMLV sequences (Lander and Chattopadhyay (1984) *J. Virol.* 53:695–698). Genomic DNA from NIH/3T3 cells, the basis for the majority of existing packaging cell lines, hybridized very strongly with both MMLV-specific probes at low or high stringency. Hybridization conditions are provided in the key below Table 1. In contrast, neither probe cross-hybridized with genomic DNA from 293 or MRC-5 cells, even at low stringency (Table 1). In addition, no cross-hybridization was seen with genomic DNA from *Mus dunni*, MDCK, Vero or Fox Lung cells at high-stringency (see Table 1, below).

TABLE 1

Screening of cell lines for cross-hybridization to MMLV LTR or gag-pol sequences
Endogenous MMLV Sequences (Hybridization)

| Hybridization Probe: | LTR | | gag/pol | |
| --- | --- | --- | --- | --- |
| Wash Stringency: | Low | High | Low | High |
| Cell Lines Tested | | | | |
| 293 (ATCC CRL 1573) | – | – | – | – |
| MDCK (ATCC CCL 34) | ± | – | ± | – |
| *Mus dunni* tail fibroblasts | ± | – | ± | – |
| Vero (ATCC CCL 81) | – | – | ± | – |
| Fox Lung (ATCC CCL 168) | – | – | ± | – |
| MRC-5 (ATCC CCL 171) | – | – | – | – |
| NIH/3T3 (ATCC CRL 1658) | ++ | ++ | ++ | ++ |
| CHO-K1 (ATCC 61) | ++ | ++ | ++ | ++ |

Key:
Hybridization signal strength: –, none; ±, weak; +, moderate; ++, strong.
Probes: LTR (positions relative to cap site of genomic RNA): nucleotides −232 (Eco RV) to 563 (Pst I of 5′ leader sequence); gag-pol: nucleotides 739 (Pst I in gag) to 3705 (Sal I in pol).
Stringency (65° C. in all instances): Low, 500 mM Na+; High, 50 mM Na+.
ATCC: American Type Culture Collection, 12301 Parklawn Drive, Rockville, Maryland, 20852, U.S.A.

Fox Lung and MRC-5 were discounted due to poor growth or limited cell division potential respectively, which would preclude sub-cloning of stably-transfected cells. Thus, 293, MDCK, *Mus dunni* and Vero cells were identified as candidate cell lines from which to derive packaging cell lines.

To decrease the probability of RCR formation, separate expression plasmids were constructed for gag-pol and env, as disclosed in Danos (1991) *Proc. Natl. Acad Sci. U.S.A.* 85:6460–6464; Danos and Mulligan, 1988) *Proc. Natl. Acad. Sci. U.S.A.* 85:6460–6464; Markovitz et al. 1988) *J. Virol.* 62:1120–1124; Miller (1990) *Human Gene Therapy* 1:5–14; Morgenstern and Land (1990) *Nucl. Acids Res.* 18:3587–3596. In contrast to existing packaging cells, however, only the minimum genetic information required to encode Gag-Pol and Env proteins was included. The structural gene sequences were amplified by polymerase chain reaction (PCR) using the primers shown below to obtain the open reading frames (ORFs) from the initiation to the termination codons of the gag-pol or env genes flanked by Not I restriction sites, and the fragments were subcloned into pBluescript SK+ (Stratagene, La Jolla, Calif.). Oligonucleotide primers (Genosys Biotechnologies, Woodlands, Tex.) corresponding to the N-terminus of the genes also placed the AUG in the ideal context for translation (Kozak (1987)) *J. Mol. Biol.* 196:947–950), and those corresponding to the C-terminus encoded a second in-frame stop codon. The integrity of PCR products was verified by DNA sequencing. The gag-pol ORF was amplified from the plasmid pVH-2, which carries the infectious Moloney MLV sequence (Miller and Verma (1984) *J. Virol.* 49:214–222), using the primer pair:

5'-AAAAAAAGCGGCCGCGCCGCCACC<u>ATG</u>GGCCAGACTGTTACCAC-3' (SEQ ID NO: 1), and

5'-AAAAAAAGCGGCCGCTCAttaGGGGGCCTCGCGGG-3' (SEQ ID NO: 2).

The underlined ATG is that of the p15Gag (bases 621 to 623) and the codon in lower case corresponds to the pol stop codon (bases 5835 to 5837). The expression plasmid pCMV-gp with the human cytomegalovirus immediate early (CMV) promoter was constructed by inserting the gag-pol fragment into the pcDNA3 plasmid (Invitrogen, San Diego, Calif.) from which the neomycin resistance expression cassette (DraIII to BsmI) had been deleted. FIG. 1 schematically shows the plasmid constructs used for expression of MMLV structural genes. Plasmids carrying the gag-pol ORF were propagated at 30° C. to prevent recombination under the conditions set forth in Joshi and Jeang (1993) *BioTechniques* 14:883–886.

To amplify the env gene, a contiguous amphotropic envelope sequence was constructed from p4070A constructed according to the method of Ott et al. (1990) *J. Virol.* 64:757–766, and amplified with the primer pair:

5'-TAATCTACGCGGCCGCCACCATGGCGCGTTCAACGCTC-3'
(SEQ ID NO: 3)
and
5'-AATGTGATGCGGCCGCtcaTGGCTCGTACTCTATGG-3'
(SEQ ID NO: 4).

The underlined ATG corresponds to bases 37 to 39, and the stop codon (lower case), bases 1998 to 2000 (Ott et al. (1990) supra. The CMV promoter-env expression plasmid pCMV*Ea was created by insertion of the env ORF in place of the beta-galactosidase gene of pCMV13 (Clontech, Palo Alto, Calif.) modified by mutation of an extraneous ATG in the SV40 intron to ACG (SD/SA*). The integrity of the PCR products was verified by DNA sequencing.

To further identify the optimal cell line, sandwich ELISA assays were developed to detect Gag and Env proteins in transfected cells and particularly in supernatants. Plates were coated with hybridoma culture supernatants from either 83A25 (available from the NIH) as disclosed in Evans et al. (1990) *J. Virol.* 64:6176–6183, for Env, or R187 (ATCC CRL 1912) for Gag. Captured proteins were detected with 79S-834 and 77S-227 anti-sera (Quality Biotech, Camden, N.J.), respectively, and horseradish peroxidase-conjugated anti-species antibodies and substrate 2,2-Azinobis (3-ethylbenzothiazoline-6-sulfonic acid) (Pierce, Rockford, Ill.).

The ability to produce vector particles was assessed by transfection of a gag-pol expression plasmid into candidate cell lines and selection of drug-resistant pools. Only the supernatants from gag-pol-transfected 293 or Mus dunni cells contained Gag protein. No Gag was secreted by transfected Vero or MDCK cells, although Gag was present in the cell lysates. Vero and MDCK cells were discounted as candidate cell lines, and human 293 cells were elected to derive packaging cells.

Construction of ProPak-A

To derive amphotropic packaging cells, the pCMV*Ea plasmid was introduced into 293 cells (ATCC CRL 1573) by co-transfection (Profection Kit, Promega, Madison, Wis.) at a ratio of 15:1 with the pHA58 plasmid (as disclosed in Riele et al. (1990) *Nature* 348:649–651) conferring resistance to hygromycin B (250 mg/ml; Boehringer, Indianapolis, Ind.). Stably-selected populations were stained with anti-Env antibody (83A25, available from the NIH) and individual Env-positive cells were isolated by automatic cell deposition on a FACStar Plus (Becton Dickinson, San Jose, Calif.). Three clones with the highest fluorescence intensity were further characterized. All three yielded equivalent titers upon transient co-transfection with gag-pol and vector plasmids.

Next, the pCMV-gp construct was stably transfected into one of the three 293-Env clones by cotransfection with the plasmid pSV2pac (as disclosed in Vara et al. 1986) *Nuci. Acids Res.* 14:4617–4624). Puromycin-resistant (1 mg/ml; Sigma, St. Louis, Mo.) clones were grown to confluence, medium was exchanged and supernatants were collected 16 hours later, filtered, and analyzed for Gag and Env production by using the sandwich ELISA as described in the previous page. Sixteen clones were identified (16/37) that secreted high levels of Gag and Env antigens. Of these, six clones produced virus in transient transfections at titers within 2 to 3-fold of Oz 2 cells (Table 2A), the amphotropic equivalent of BOSC 23 cells (see Pear et al. (1993) *Proc. Natl. Acad Sci. U.S.A.* 90:8392–8396).

TABLE 2A

Comparison of end-point titers from transiently-transfected ProPak-A cell clones

| Transient Titers - MFG lac Z Vector Cell Line or Clone # | End-Point Titer (cfu × $10^{-5}$/ml) |
|---|---|
| Oz2 | 13.8 ± 0.3 |
| ProPak.12 | 8.8 ± 0.8 |
| ProPak.31 | 8.0 ± 0.5 |
| ProPak.6 | 7.5 ± 0.0 |
| ProPak.27 | 6.8 ± 1.2 |
| ProPak.21 | 6.0 ± 1.0 |
| ProPak.5 | 6.0 ± 2.0 |

Supernatants were collected after 16 hours at 32° C., and end-point titers determined on NIH/3T3 cells using the materials and methods disclosed above.
cfu: colony forming units.

Cells were seeded at $2 \times 10^5$ cells/cm$^2$ in 6-well plates, and transfected 16 hours later with 2.5 mg/well MFG-lacZ DNA (Dranoff et al. (1993) supra and described herein) was in the presence of 25 mM chloroquine (Pear et al. (1993), supra). Titers are the average and range for duplicate transfections. Oz 2 cells also are called Bing cells and are the amphotropic equivalent of BOSC23 cells (Pear et al., 1993).

TABLE 2B

Comparison of end-point titers from stable producer cell clones with the LMTNL Vector

| | End-Point Titer |
|---|---|
| Producer Clone | (G418$^r$ cfu × $10^{-6}$/ml) |
| PA317.LMTNL | 1.7 ± 0.7 |
| ProPak-A.6.LMTNL.6 | 2.1 ± 0.3 |
| ProPak-A.6.LMTNL.7 | 2.2 ± 0.8 |

Supernatants were collected after 16 hours at 32° C., and end-point titers determined on NIH/3T3 cells
cfu: colony forming units.
Supernatants were harvested from confluent cultures of producer cell clones in T-75 flasks.
The average and range for triplicate samples is given.

One clone with high transient transfection titers was selected and designated ProPak-A.6. ProPak-A.6 was deposited with the American Type Culture Collection (ATCC), 10801 University Blvd. Manassas, Va. 20110-2209 on Dec. 15, 1995, under the provisions for the Budapest Treaty for the Deposit of Microorganisms for the Purposes of Patent Procedure, and was accorded ATCC Accession No.CRL 12006. Transient titers reflect the efficiency of transient transfection, and the titers obtained with ProPak-A cells are lower than those achieved with Oz 2 cells, possibly because Oz 2 is based on a 293T cell clone selected for high transient transfection efficiency (Pear et al. (1993) supra).

Construction of ProPak-X

A xenotropic packaging cell line, designated ProPak-X, was constructed as follows. The ATG in the splice donor/splice acceptor of pCMV plasmid was mutated to ACG as described above. The CMV promoter was excised (EcoRI/XhoI, blunt-ended), and replaced with the MoMLV LTR (Asp 718/HindIII, blunt-ended) from plasmid pVH2. The β-galactosidase gene was replaced by the gag-pol ORF (NotI fragment) to generate pMoMLVgp. pMoMLVgp was co-transfected with pHA58 into 293 cells (ATCC CRL 1573) by calcium phosphate co-precipitation and hygromycin B-resistant cells were selected. Clones were screened for the level of Gag secretion and one clone secreting high levels of Gag was selected (designated ProGag); this clone yielded high viral titers in transient transfection.

The plasmid pNZBxeno, containing the murine xenotropic env gene, was obtained from Christine Kozak (NIH). The non-contiguous env sequences in pNZBxeno were made contiguous by digestion with SalI and EcoRI and ligation into the SalI site of pBluescript (Stratagene). The xeno env ORF was amplified by PCR and cloned into XhoI/XbaI digested pCI (Promega) to generate the expression plasmid pCI*Ex. pCI*Ex was co-transfected with pSV2pac into the cell line selected as above (ProGag) by calcium phosphate precipitation and puromycin-resistant cells were selected. The resulting cells were screened for Env expression by flow cytometry and clones designated ProPak-X, expressing high levels of Env were screened for ability to produce transducing vector. Samples of one clone, clone 36 designated ProPak-X.36, have been deposited with the American Type Culture Collection (ATCC), 10801 University Boulevard, Manassas, Va. 20110-2209 U.S.A. on Dec. 15, 1995, under the provisions for the Budapest Treaty for the Deposit of Microorganisms for the Purposes of Patent Procedure, and the deposit was accorded ATCC Accession No.CRL 12007.

Supernatant produced by ProPak-X based producer cells were tested for end-point titer and transduction efficiency as described above, except that human 293 cells were used as the target cells.

In a similar manner to ProPak-X, amphotropic cell lines were also derived by transfection of the amphotropic envelope-encoding plasmid, pCMV*Ea, into ProGag cells and isolation of clones yielding high transduction efficiencies. One of these, clone number 52 (ProPak-A.52), is used extensively in experiments described herein.

Lack of RCR

The safety of the ProPak-A cells was determined by stringent testing for the ability to recombine to generate RCR. In previous work it was found that the vector BC140revM10 (Bevec et al. (1992) Proc. Natl. Acad Sci. USA. 89:9870–9874) reproducibly gave rise to RCR in PA317 cells. BC140revM10 carries the extended packaging sequence, including the ATG of the gag ORF. The LMTNL vector (constructed as described in Escaich et al. (1995) supra), in contrast, lacks part of the 5' untranslated region and contains no gag sequences and is therefore less likely to recombine and form RCR. (See FIG. 2). The BC140revM10 or LMTNL vectors were each introduced into PA317 or ProPak-A cells and culture supernatants were tested for RCR (using the methods disclosed in Haapala et al. (1985) J. Virol. 53:827–833 and Printz et al. (1995) Gene Therapy 2:143–150) at weekly intervals. The PA317/BC140revM10 combination (transfected or transduced) gave rise to RCR detectable by direct inoculation of culture supernatant onto PG4 cells at 4 weeks (Table 3, below). Cultures were maintained for 4 more weeks, and also tested by co-culture of producer cells with M. dunni cells to amplify any RCR in the culture, followed by S+L– assay on PG4 cells. Even by this stringent assay for RCR, the ProPak-A-based producer pools were all free of RCR (Table 3).

TABLE 3

Assay for presence of RCR in cultures carrying the BC140revM10 or LMTNL vectors

| Packaging Cell Line | Transfected with: | Transduced with: | Supernatant RCR (wk) | Co-culture RCR (wk 8) |
|---|---|---|---|---|
| ProPak-A | pBC140revM10 | N/A | (>8) | Negative |
| ProPak-A | pLMTNL | N/A | (>8) | Negative |
| ProPak-A | N/A | M(G).BC140revM10 | (>8) | Negative |
| ProPak-A | N/A | M(G).LMTNL | (>8) | Negative |
| PA317 | pBC140revM10 | N/A | 4 | Not tested |
| PA317 | pLMTNL | N/A | (>8) | Negative |
| PA317 | N/A | M(G).BC140revM10 | 4 | Positive |
| PA317 | N/A | M(G).LMTNL | (>8) | Negative |

RCR detected by S + L-assay on PG4 cells (ATCC CRL 2032) by inoculation with supernatant from producer cell cultures, or after 3 passages of co-culture with Mus dunni cells.
N/A: not applicable.
(>8): no RCR detected 8 weeks after G418-resistant pools established.
M(G).: transient MMLV(VSV-G) pseudotype (Yee et al. (1994) Proc. Natl. Acad. Sci. 91: 9564–9568) used as inoculum.

RCR detected by S+L– assay on PG4 cells (ATCC CRL 2032) by inoculation with supernatant from producer cell cultures, or after 3 passages of co-culture with Mus dunni cells.
N/A: not applicable.
(>8): no RCR detected 8 weeks after G418-resistant pools established.
M(G).: transient MMLV(VSV-G) pseudotype (Yee et al. (1994) Proc. Natl. Acad. Sci. 91:9564–9568) used as inoculum.

Resistance to inactivation by human serum

Figure 3:
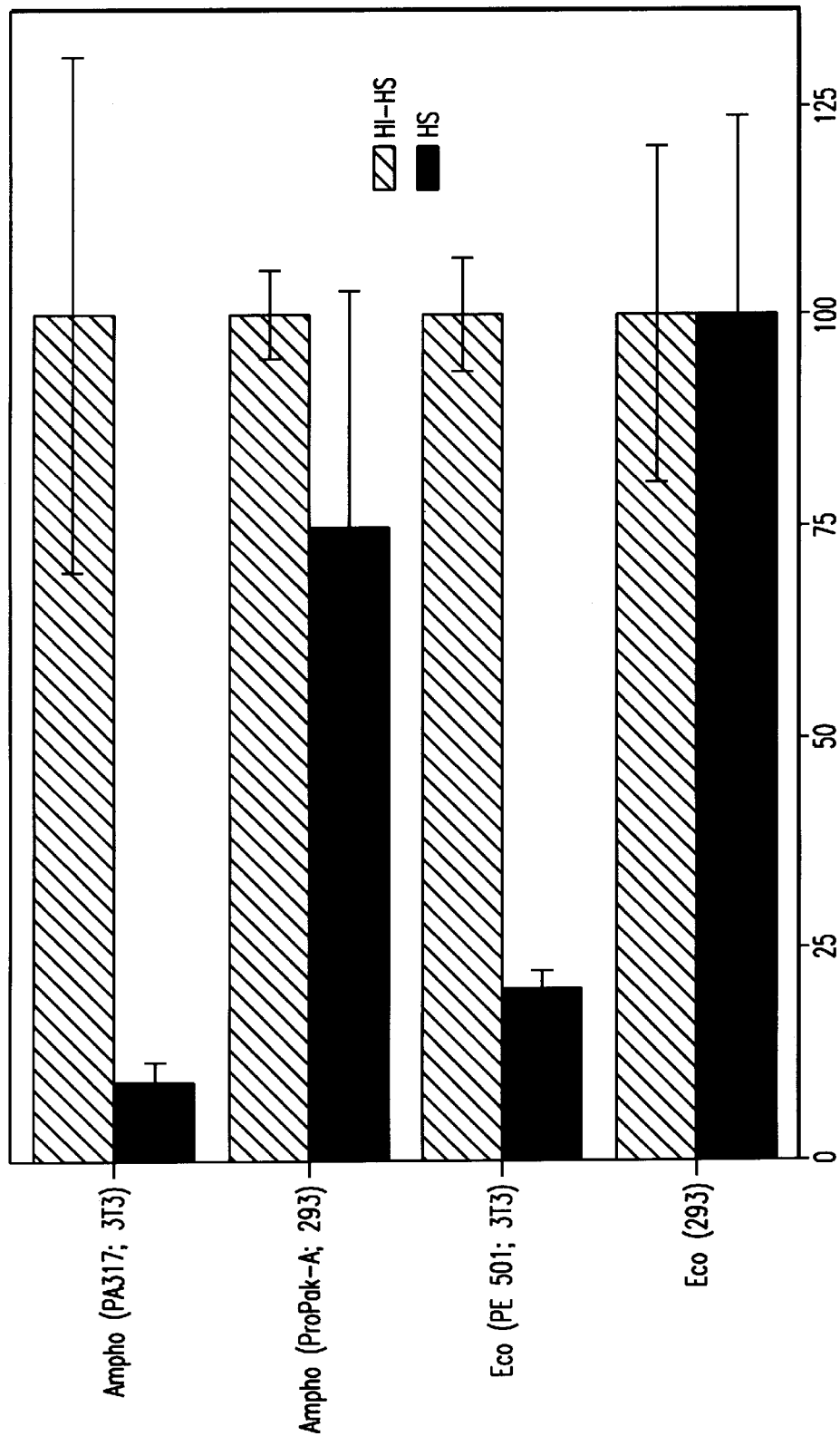
FIG. 3 shows the result of exposing to human serum, supernatants containing lacZ-encoding vector prepared from stable producer cells (PA317; PE501), by transient transfection of vector into packaging cells (ProPak-A) or by co-transfection of packaging and vector constructs into 293 cells (293). Supernatants were mixed with an equal volume of a pool of human serum from 4 healthy donors, incubated for 1 hour at 37° C., and the residual titer determined on NIH/3T3. The serum was either untreated (HS) or had been heat-inactivated for 30 min at 56° C. (HI-HS). The human serum pool had a hemolytic titer ($CH_{50}$; EZ Complement Assay, Diamedix, Miami, Fla.) of 117 to 244 before, and <8 after heat-inactivation. End-point titers (cfu×10−5/ml) of supernatants treated with heat-inactivated serum (100%) were: PA317, 5.0; ProPak-A, 1.0; PE501, 1.4, and 293, 1.1. The bars indicate the range for duplicate samples. HI-HS denotes heat inactivated human serum. HS denotes human serum.

Recently, interest has arisen in the in vivo application of retroviral gene transfer by direct administration of vector particles into human beings. In addition, targeting of particles bearing hybrid ligand-ecotropic env genes to specific receptors has been reported (Kasahara et al. (1994); Science 266:1373–1376 Somia et al. (1995); Proc. Natl. Acad. Sci. U.S.A. 92:7570–7574; Cosset et al. (1995) J. Virol. 69:6314–6322). A pre-requisite is that the particles are not inactivated by human serum. Therefore, ProPak-A.6 or A.52, ProPakX or PA317-packaged vector particles were analyzed for susceptibility to inactivation by human serum. In addition ecotropic supernatants packaged in either PE501 cells (NIH/3T3-based; see Miller and Rosman, (1989) BioTechniques 7:980–990) or in 293 cells were analyzed. Vector particles with the various envelopes produced from 293 cells were resistant, while supernatants packaged in NIH/3T3 cells were inactivated by incubation with human serum (FIG. 3). Takeuchi et al. (1994) supra, concluded that resistance of vector particles to human serum was determined by both the host cell type and the viral envelope. The data submitted herein shows that packaging of amphotropic, xenotropic and ecotropic vectors in 293-based cells is sufficient to confer resistance to human complement.

For the data presented in Examples 2 and 3, herein, the parental packaging cell line was PA317, unless otherwise noted.

EXAMPLE 2

Comparison of End-Point Titer and Transduction Efficiency

For gene therapy applications, it is necessary to generate large volumes of characterized supernatants, which cannot be easily prepared by transient transfection.

It was therefore necessary to determine the stable end-point titers and the transduction efficiencies. End-point titers were determined for supernatants from producer cell clones which had been transduced with the PA.LMTNL vector, in which an internal thymidine kinase promoter (T in vector name) drives the neomycin phosphotransferase gene (N). As shown in Table 2B, end-point titers from ProPak-A-based producer cells were marginally higher than those for the best PA317-based producer clone. In addition, the titers from ProPak-A.LMTNL producer pools were stable when passaged for 3 months in the absence of drug selection.

Figure 4A:
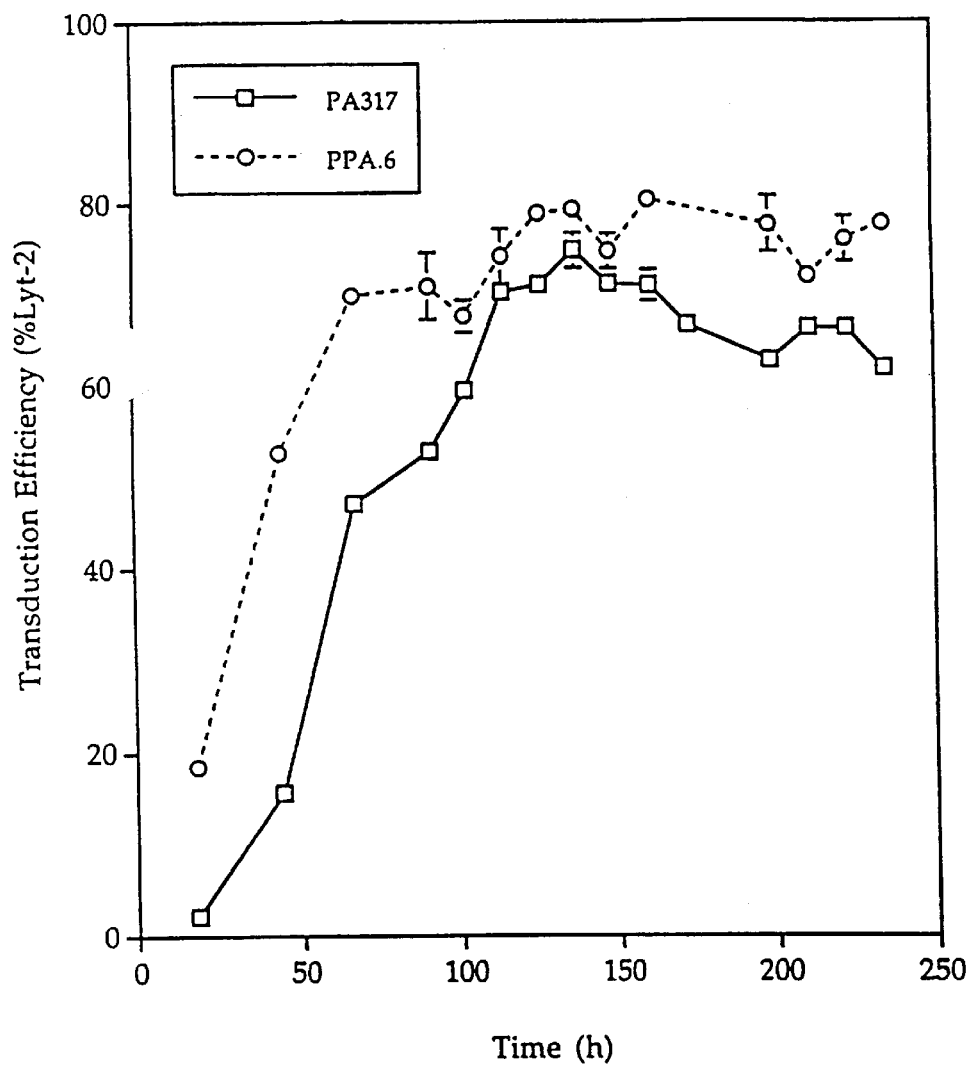
FIGS. 4A, 4B and 4C show transduction efficiencies of vector supernatants.
Figure 4B:
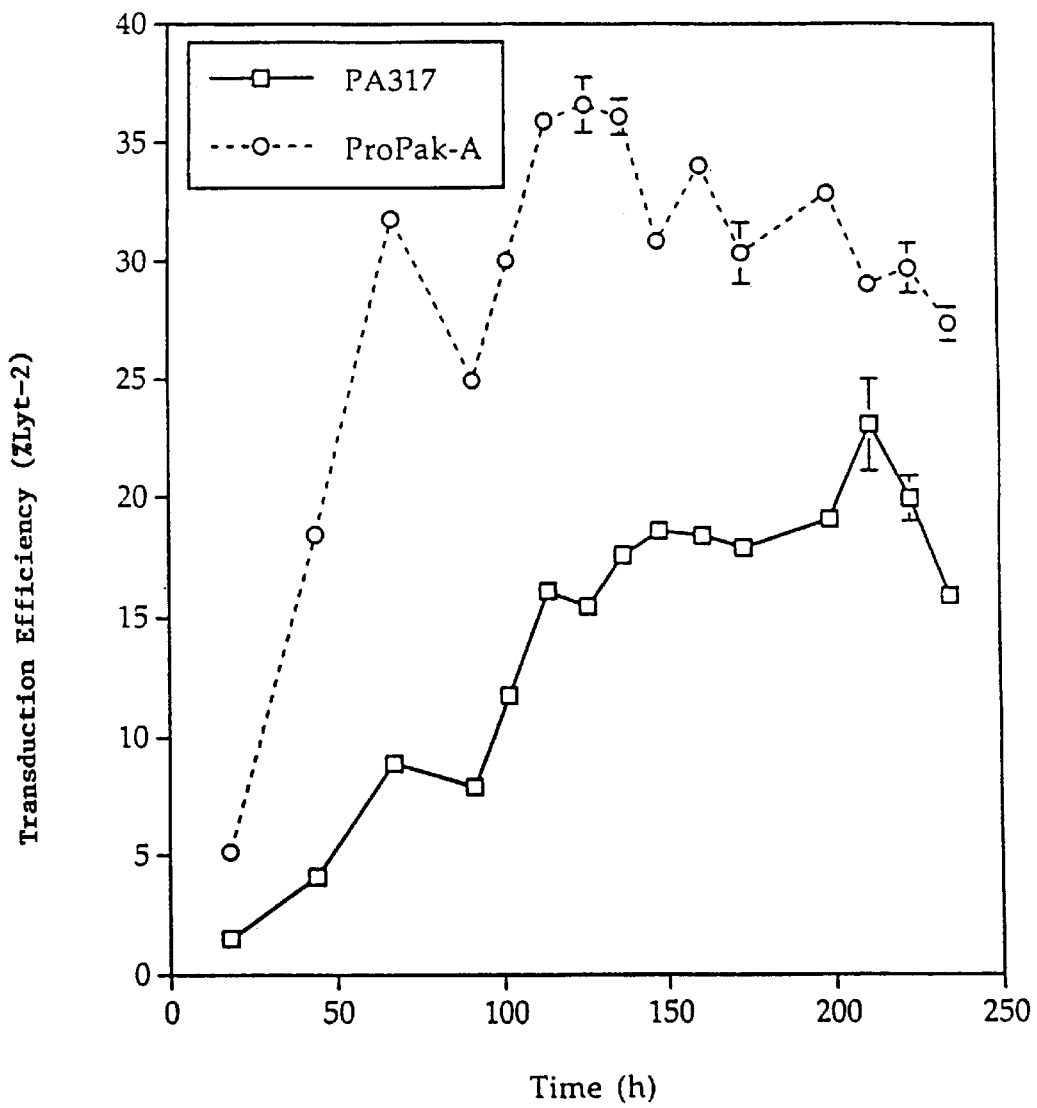
Figure 4C:
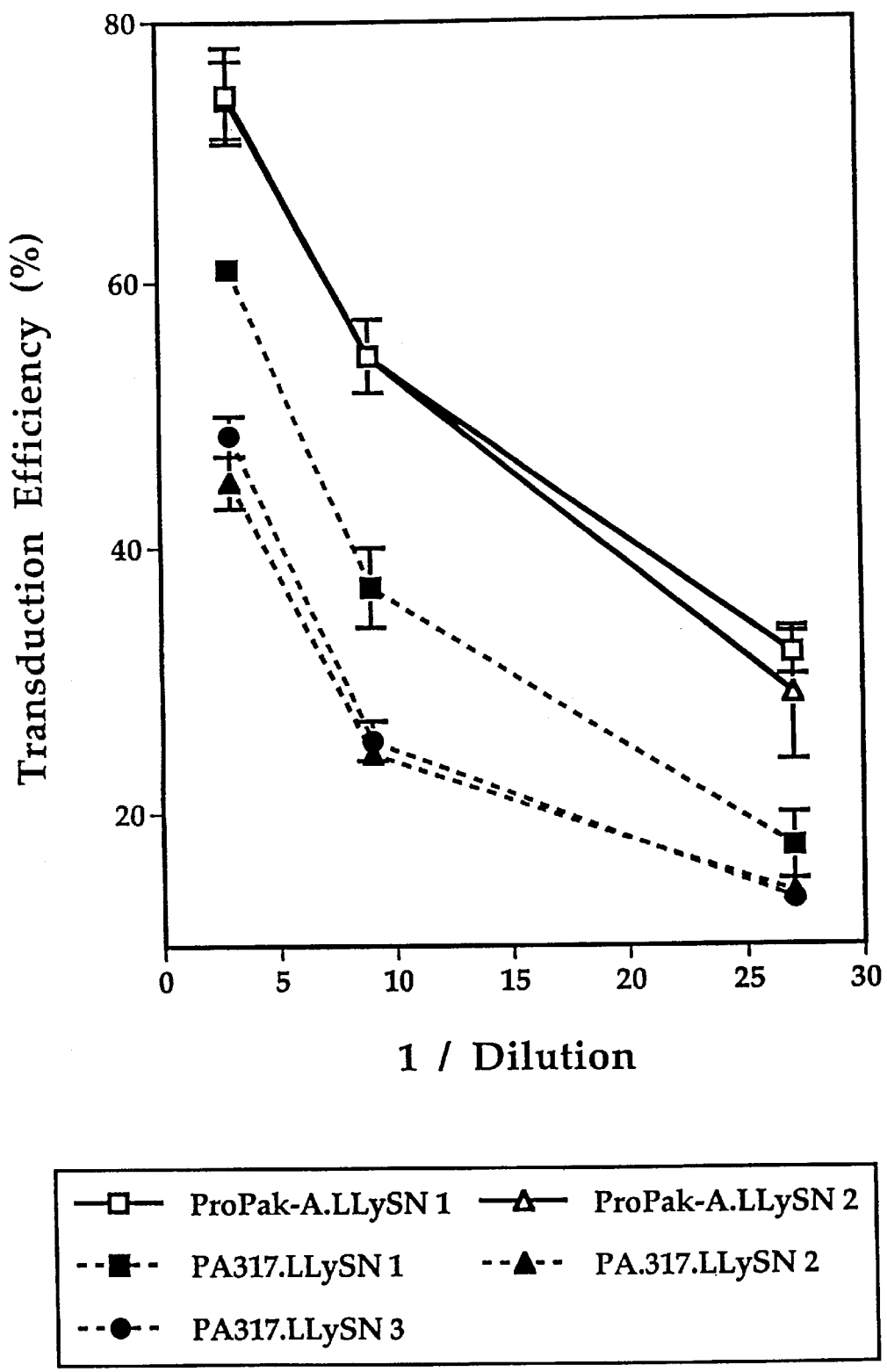

As shown herein, while end-point titers are broadly used, transduction efficiency is a better measure of gene transfer potency. However, the assay can be laborious with vectors encoding drug resistance genes. Therefore PA317- or ProPak-A-based producer cell populations carrying a vector (LLySN, FIG. 2) derived from the LXSN vector (Miller and Rosman (1989) supra) were prepared by insertion of the Lyt2 surface marker gene (Tagawa et al. 1986) supra). Surface expression of the Lyt2 antigen allows simple, quantitative determination of transduction efficiency by FACS. Higher transduction efficiencies were achieved with supernatants from two independently-derived ProPak-A-LLySN populations than with supernatants from three PA317.LLySN pools assayed on NIH/3T3 cells (see FIG. 4C). Surprisingly, when the same supernatants were assayed for transduction efficiency on human 293 cells, the superiority of ProPak-A is even greater (FIG. 4B).

Figure 5B:
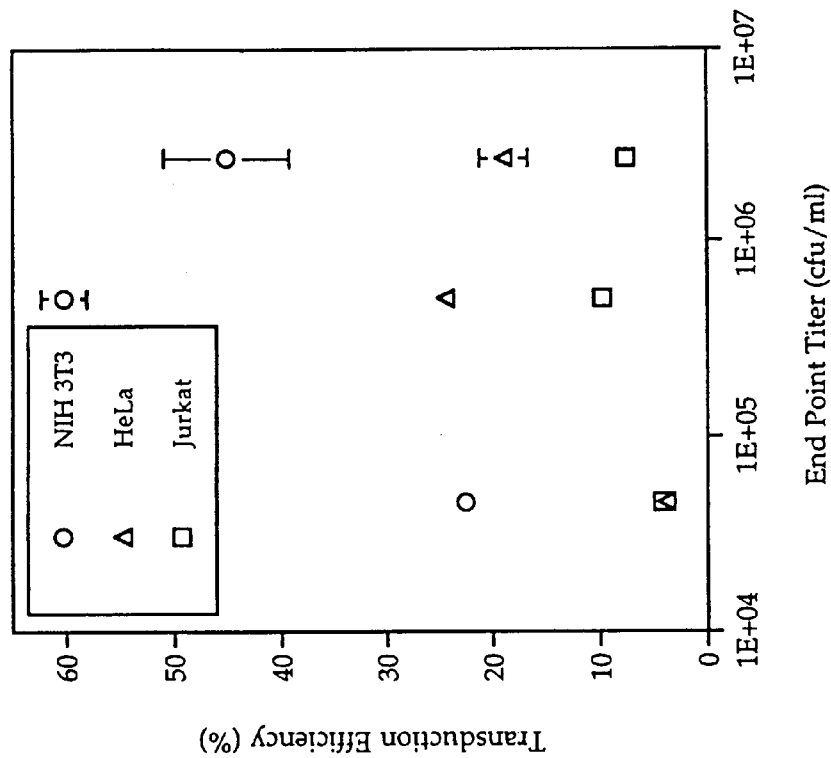
FIGS. 5A and 5B show the results of comparison of transduction mediated by various viral vector supernatants. 5A is a comparison of end-point titer and transduction efficiency for PA.SVNLZ supernatants measured on NIH/3T3 cells.
Figure 5A:
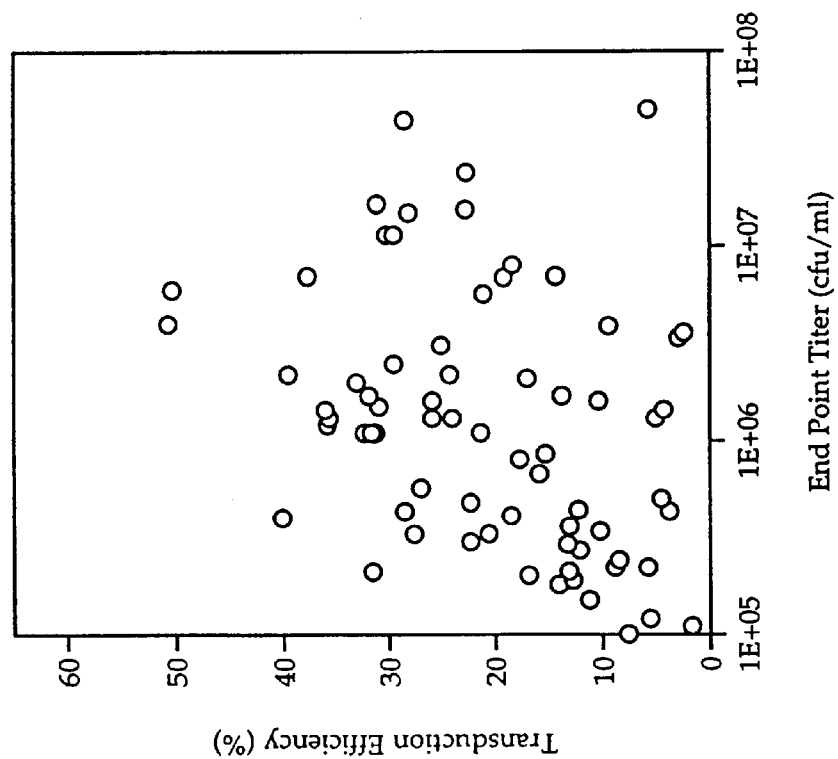

To determine the relationship of end-point titer to transduction efficiency, supernatants were harvested from producer cells cultured under a variety of conditions to optimize production of retroviral vector supernatants. In addition to assaying end-point titers, the proportion of cells transduced after a single inoculation (i.e. transduction efficiency) also was determined. FIG. 5A shows the end-point titers and transduction efficiencies obtained with 70 different PA317-derived-β-galactosidase-encoding SVNLZ (PA.SVNLZ; FIG. 2) vector supernatants. No direct correlation between the end-point titer and transduction efficiency of the supernatants was found (correlation factor, r=0.07). To confirm that the lack of correlation between transduction efficiency and end-point titer was not specific to the NIH/3T3 cells or the flow cytometry method used to quantitate the proportion of cells transduced with the PA317-derived SVNLZ vector, supernatants containing an amphotropic retrovirus encoding the neomycin phosphotransferase gene (LMTNL, FIG. 2) were tested on NIH/3T3 as well as Jurkat and HeLa cells (FIG. 5B). The results demonstrate that the supernatant which yielded the highest transduction efficiency on NIH/3T3 cells also gave the highest transduction efficiency on both Jurkat and HeLa cells (FIG. 5B). Furthermore, the supernatant which yielded the highest transduction efficiency did not have the highest end-point titer, again distinguishing between these two functional measurements. Similar results also were obtained with the PA.SVNLZ vector on several different cell lines suggesting that the lack of correlation between end-point titer and transduction efficiency is neither specific to the indicator gene nor to the target cell species.

Concentration of Vector Supernatants

The lack of correlation between end-point titer and transduction efficiency also was apparent when the effect of physically concentrating retroviral vector supernatants by ultrafiltration was examined. Vector supernatants were concentrated using three different ultrafiltration systems. The Sartocon Mini cross flow ultrafiltration system (Sartorius, Bohemia, N.Y.) was used with a 77.4 $cm^2$, 100,000 kDa molecular weight cut-off (MWCO) polysulfone module at a feed pressure of 3 pounds per square inch (psi). Concentration was achieved within one hour at room temperature. An Amicon Stirred Cell model 8050 (Amicon, Beverly, Mass.) was used with a YM100 ultrafilter (3.4 $cm^2$, 100,000 kDa MWCO). Positive pressure was maintained with sterile, filtered regulated air, and concentration achieved in 30 minutes at room temperature. Small volumes (5 to 20 ml), were concentrated using Filtron 300,000 kDa MWCO centrifugal concentrators (Filtron Tech. Corp., Northborough, Mass.). Concentration was achieved within 45 minutes by centrifugation at 3,000 g in a Beckman GS-6KR centrifuge (Beckman, Palo Alto, Calif.) at 4° C.

Figure 6:
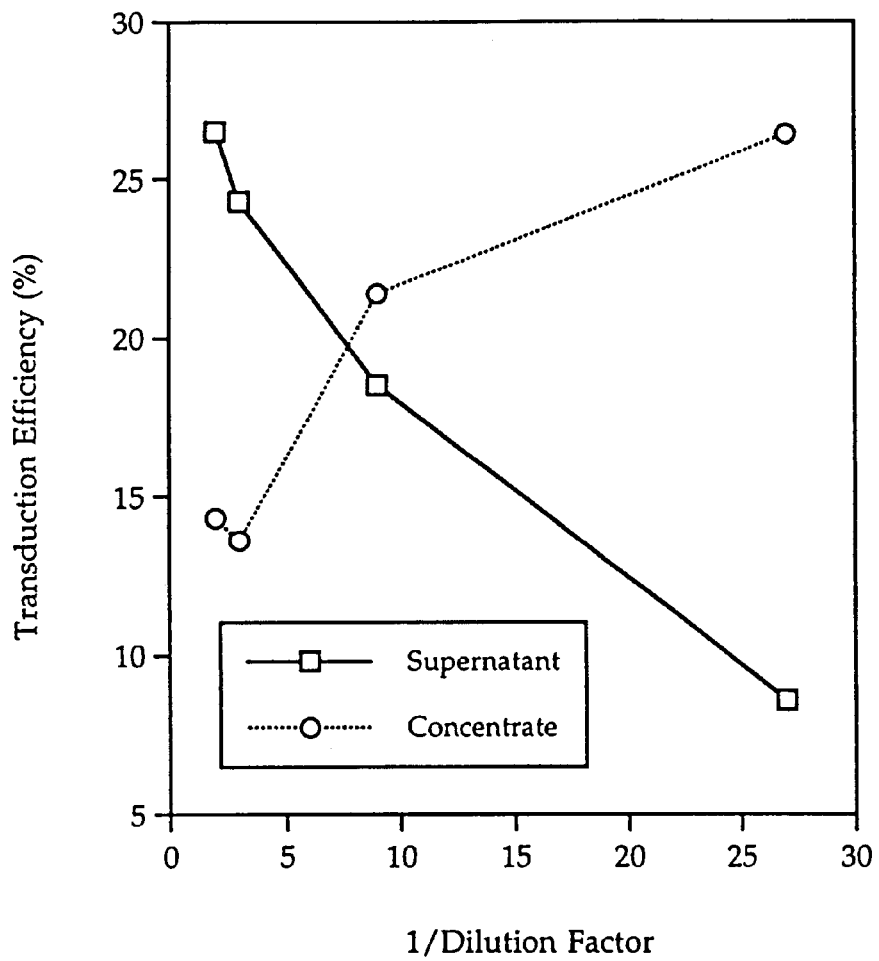
FIG. 6 shows the transduction efficiency of PA.SVNLZ supernatants before or after concentration. The original supernatant and the concentrate (see Example 2 and Table 4) were diluted with medium and inoculated onto NIH/3T3 cells.

Table 4 summarizes data from five independent experiments using two different retroviral vectors and the three different ultrafiltration systems. End-point titers increased in proportion to the volume reduction (up to 19-fold), indicating that the vector was not inactivated by this procedure. However, higher transduction efficiencies were not achieved. Equivalent transduction efficiencies were achieved with supernatants produced at 32° C. before and after concentration (Table 4). In contrast, retroviral vector supernatants produced at 37° C. had lower transduction efficiencies following ultrafiltration (Table 4). Interestingly, the lower transduction efficiencies could be restored to the level of the original supernatant by diluting the concentrates (see FIG. 6), suggesting that an inhibiting agent had been co-concentrated with the transducing particles. In principle, the inhibitor could be non-transducing retroviral particles, non-vector-associated envelope protein, or a non-viral component of the tissue culture supernatant.

TABLE 4

CONCENTRATION OF RETROVIRAL VECTORS BY
DIFFERENT ULTRAFILTRATION SYSTEMS

| Expt. | Temp (° C.) | Vector | Ultrafiltration System | Volume Reduction | End Point Titer (cfu/ml × 10$^{-6}$) | | Transduction Efficiency (%) | |
|---|---|---|---|---|---|---|---|---|
| | | | | | Before Conc. | After Conc. | Before Conc. | After Conc. |
| 1 | 37 | SVNLZ | Sartocon 100 kD | 8.4x | 0.34 | 2.4 | ND | 4.5 |
| 2 | 37 | SVNLZ | Amicon 100 kD | 6.7x | 1.6 | 7.0 | 25.9 | 14.3 |
| 3 | 37 | SVNLZ | Filtron 300 kD | 5.9x | 8.0 | 50.0 | 17.6 | 5.7 |
| 4 | 32 | SVNLZ | Filtron 300 kD | 14.3x | 0.3 | 5.7 | 22.3 | 21.1 |
| 5 | 32 | LMTNL | Filtron 300 kD | 7.5x | 2.9 | 44.0 | 28.5 | 27.0 |

Envelope-Specific Inhibition of Retroviral Vector Transduction

To address the nature of the inhibiting agent, tissue culture supernatant from different packaging cell lines or NIH/3T3 cells was tested to determine whether it could inhibit transduction. Supernatants from packaging cell lines contain all the necessary vector particle proteins, but lack vector genomes and hence are unable to transduce cells. Ecotropic vectors use different receptors to enter cells than amphotropic vectors and competition for binding to receptors can occur only between viral particles with the same tropism. PA.SVNLZ supernatant was mixed with supernatant from the following: parental amphotropic PA317 packaging cells; supernatant from the ecotropic GP+E86 packaging cell line; PA.SVNLZ concentrate from above or supernatant from NIH/3T3 cells, and the transduction efficiency and end-point titers were measured.

Addition of supernatant from NIH/3T3 cells or the GPE+86 packaging cell line had no effect on transduction efficiency or end-point titer (Table 5). In contrast, addition of either parental PA317 or concentrated vector supernatant derived from producer cell line PA.SVNLZ reduced transduction efficiency, even though in the latter case, the end-point titer was increased by addition of the concentrated PA.SVNLZ supernatant (Table 5). These data indicate that inhibition of amphotropic vector transduction by amphotropic envelope protein in particulate or free form.

TABLE 5

Comparison of the transduction of NIH/3T3 cells achieved with
PA.SVNLZ supernatant diluted 1:1 with other supernatants

| Supernatant | Transduction † Efficiency (%) | End-Point † Titer (cfu/ml × 10$^{-6}$) |
|---|---|---|
| NIH/3T3 | 22.9 ± 0.5 | 1.4 ± 0.5 |
| GP + E86 (no vector) | 24.0 ± 0.5 | 2.0 ± 0.3 |
| PA317 (no vector) | 12.1 ± 0.4 | 2.5 ± 0.3 |
| Conc. PA.SVNLZ* | 12.7 ± 0.4 | 3.7 ± 0.1 |

*8.4-fold concentrate with Sartocon 100 kD ultrafilter (Experiment 1, Table 4)
† values given are the average of two samples, and the range.

Stability of Retroviral Vector Particles at Different Temperatures

Concentration of supernatant produced at 37° C. reduced transduction efficiency relative to the original supernatant (Table 4). It is possible that these supernatants contain a higher proportion of inactivated vector than supernatants produced at 32° C. To test vector particle stability at different temperatures, SVNLZ supernatant produced at 32° C. was incubated at either 37° C., 32° C., or 0° C. for various lengths of time. The original supernatant had a transduction efficiency of 25% (see FIG. 7A), and after incubation for 24 hours at 37° C., 32° C. or 0° C. the transduction efficiencies were reduced to 2, 14 and 22% respectively. Incubation at 0° C. for 4 days further reduced the transduction efficiency to 12%, while the end-point titer remained relatively stable (see FIG. 6B). At all temperatures examined, transduction efficiency declined more rapidly than end-point titer. The half-life of vector particles at 37° C. was calculated as 4.1 hour based on the end-point titer, similar to previous reports. The half-life of vector at 32° C. and 0° C. was 12.0 hours and 123.4 hours, respectively. It is interesting to note that at all temperatures examined, end-point titer remained relatively stable (2.5±0.4×10$^6$ cfu/ml) for at least the first eight hours. This initial stability in end-point titer, which was not observed for transduction efficiency, has been seen in three separate experiments using either the PA.SVNLZ or PA.LMTNL vector.

Retroviral Production Kinetics

Figure 7A:
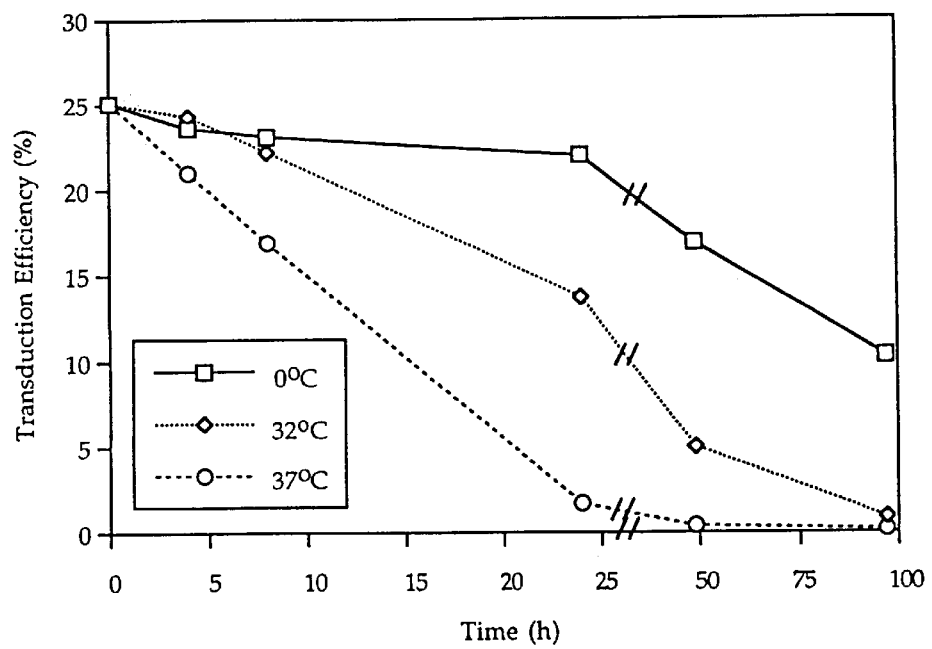
FIGS. 7A and 7B show measurement of transduction efficiency (FIG. 7A) or end-point titer of PA.SVNLZ retroviral vector supernatant on NIH/3T3 cells (FIG. 7B), showing the inactivation of vector incubated at 37° C., 32° C. or 0° C.
Figure 7B:
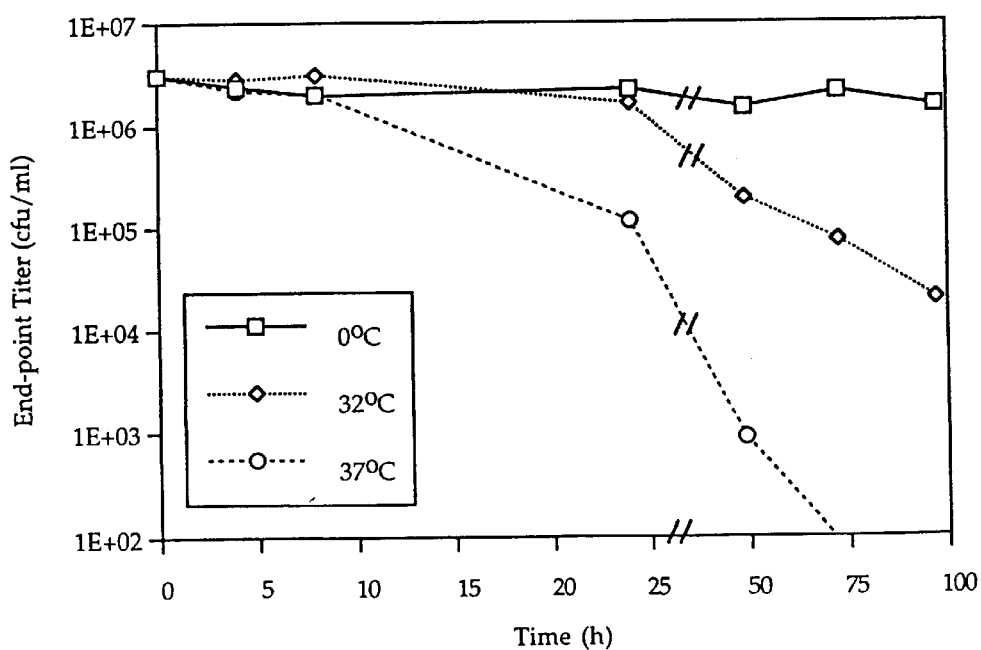
Figure 8A:
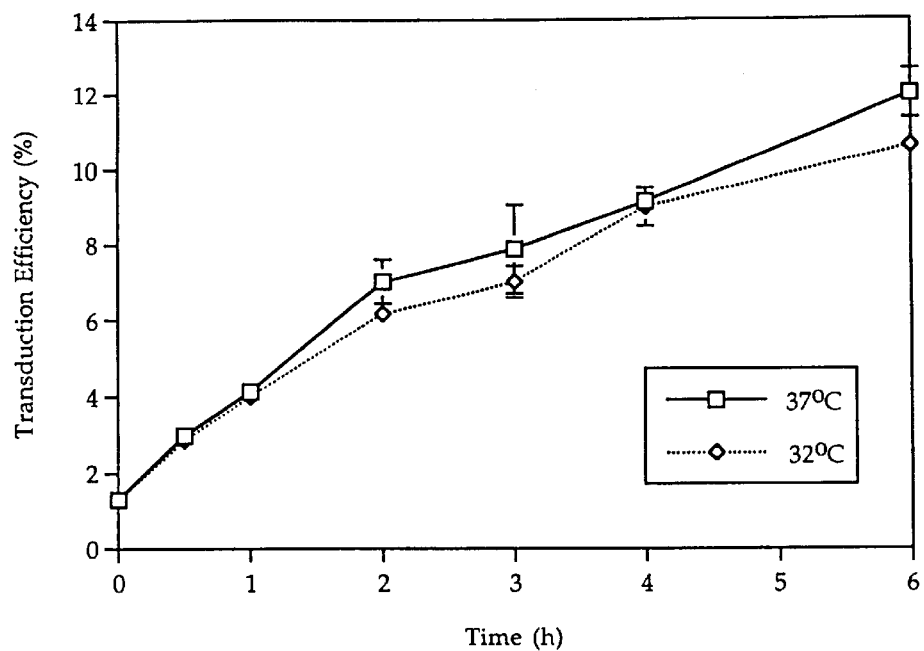
Figure 8B:
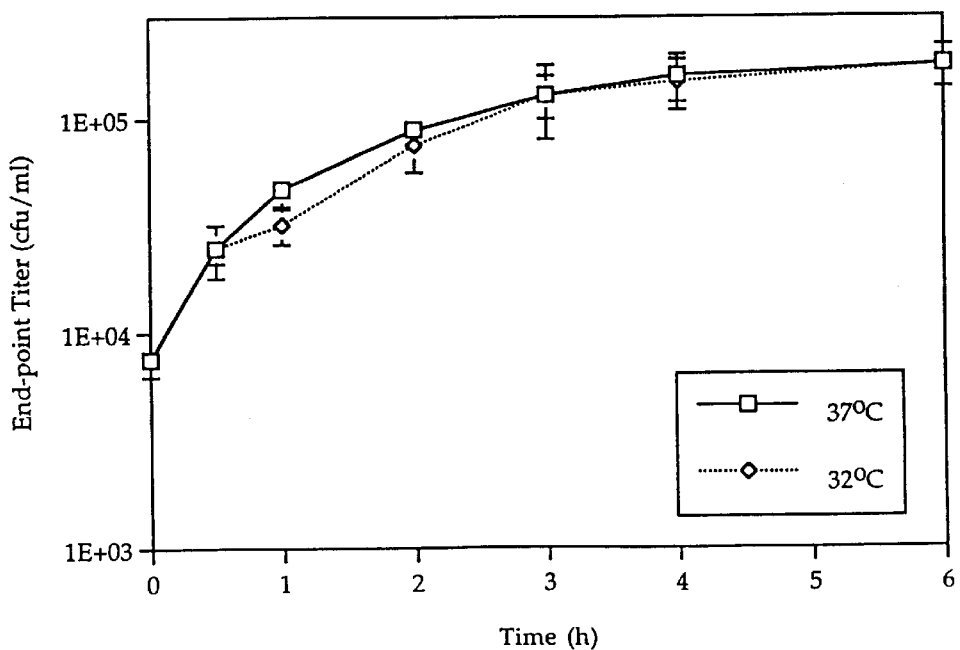

Given the greater stability of retroviral vector particles at 32° C. than at 37° C., experiments were performed to study the kinetics of vector production at these temperatures. SVNLZ producer cells were grown to approximately 80% confluency at 37° C., at which time the medium was changed and the cells placed at either 37° C. or 32° C. Supernatant samples were collected at different time points, snap-frozen, and assayed for both end-point titer (FIG. 8A) and transduction efficiency (FIG. 8B). Over the first 6 hours, similar amounts of transducing vector accumulated in cultures at 37° C. or 32° C. (FIGS. 7A and 7B). Calculations incorporating the inactivation rate of the vector at 37° C. or 32° C. show that the rate of vector production is slightly higher at 37° C. than at 32° C. (0.031 cfu/cell/hour compared to 0.027 cfu/cell/hour). Consistent with this, the amount of p30 capsid or gp70 envelope protein present in the samples measured by ELISA demonstrated that vector secretion is also marginally higher at 37° C. than at 32° C. Similar results were also found with the LMTNL vector.

Figure 9:
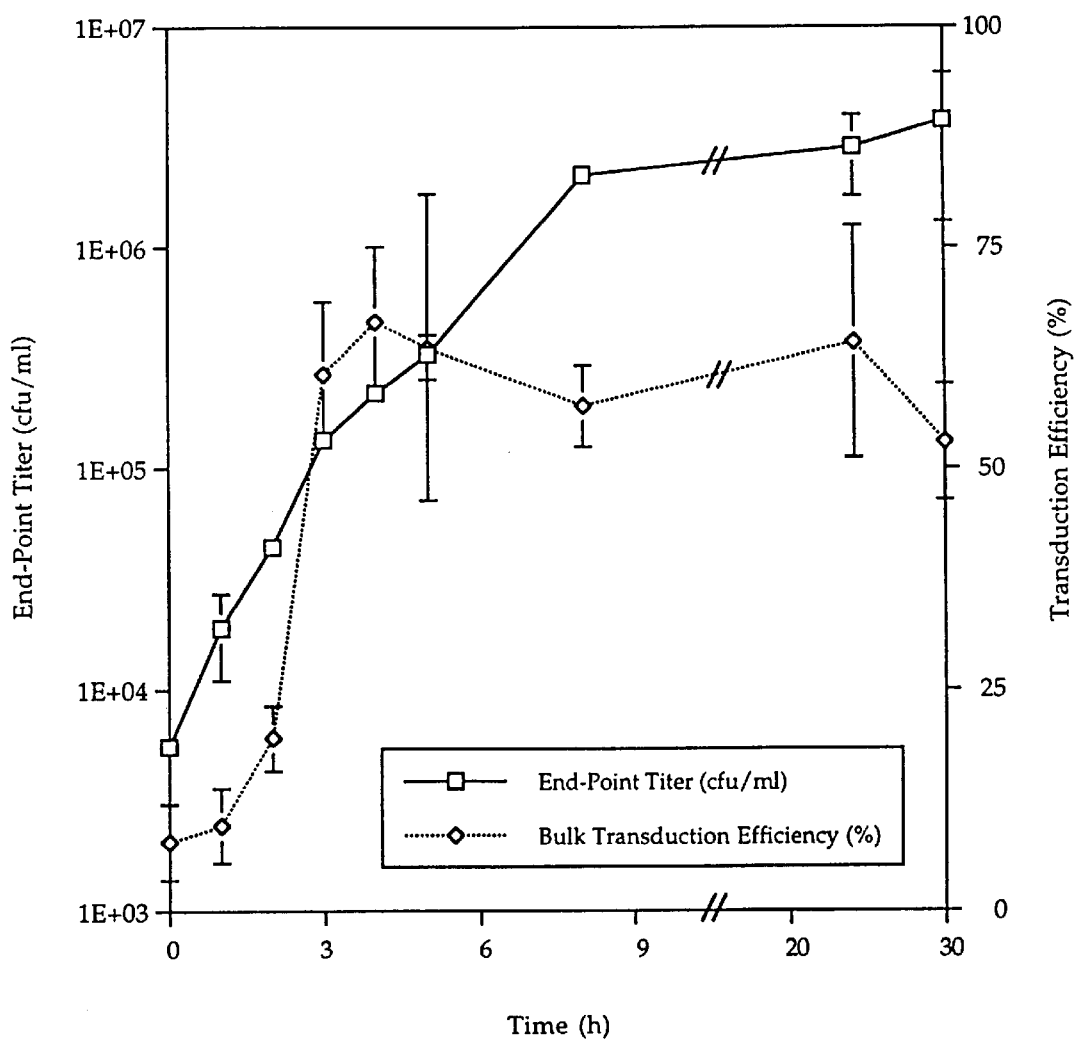
FIG. 9 is a time-course of PA.LMTNL vector production from a confluent roller bottle culture at 32° C. as measured by transduction efficiency or end-point titer.

While the rate of virion inactivation is lower at 32° C. than 37° C., the inactivation of vector particles at 32° C. is still significant (FIG. 7A), and the time that supernatants remain at this temperature should therefore be minimized. Experiments were performed to determine the minimum time required to produce supernatants with maximal transduction efficiency. FIG. 9 gives the time-course of vector production from a confluent PA.LMTNL producer cell culture in a roller bottle at 32° C., and shows that the transduction efficiency reaches a plateau 3 hours after medium exchange.

EXAMPLE 3

Comparison of Production Methods

Figure 10A:
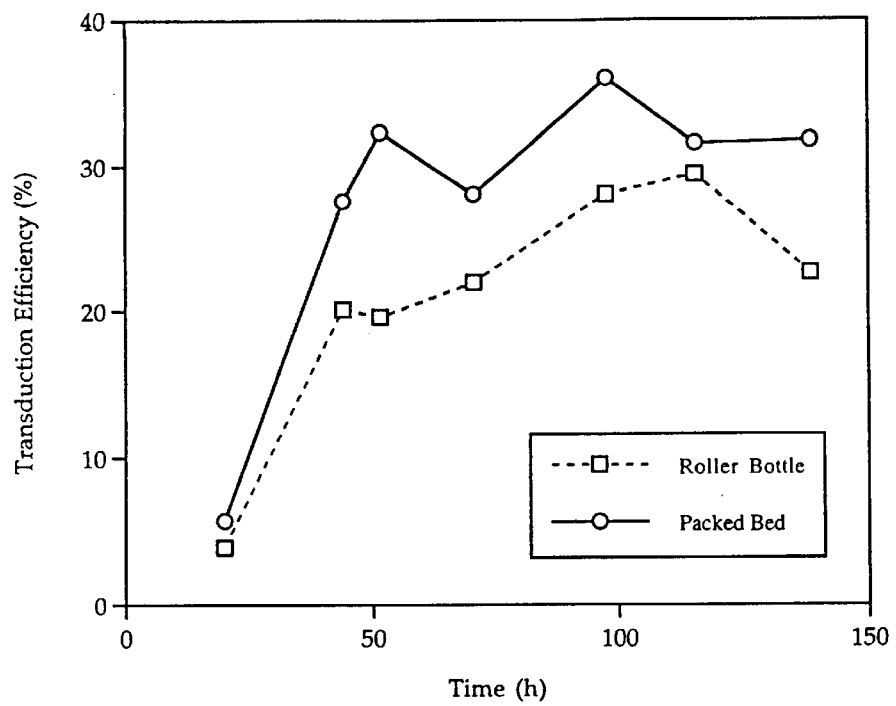
FIGS. 10A and 10B show a time-course of vector production for PA.SVNLZ producer cultures in a roller bottle (900 cm$^2$) or packed bed-bioreactor (12,000 cm$^2$) shown by transduction efficiency (FIG. 10A) or end-point titer (FIG. 10B). 1E+05 means an end-point titer of 1×10$^5$ cfu/ml on NIH/3T3 cells.
Figure 10B:
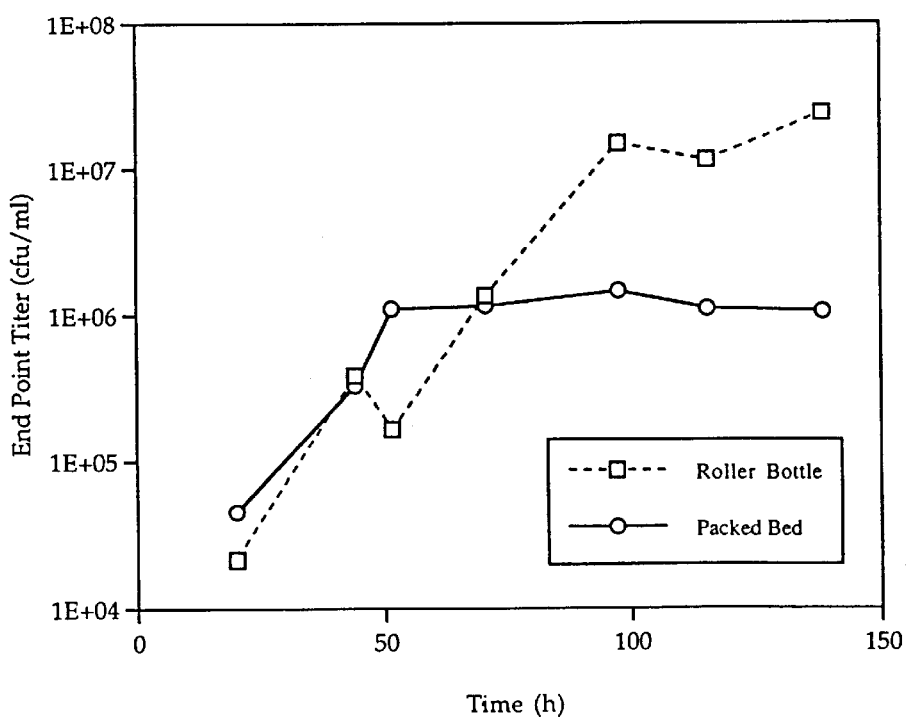

The kinetics of vector production from PA317-based producer cell lines suggest that once producer cells reach confluency, supernatants should be collected every 3 to 5 hours to obtain supernatant with a high transduction efficiency. To achieve these conditions, a bench scale packed-bed bioreactor was operated under either fed-batch (periodic medium exchange) or perfusion mode (continual medium perfusion). In the latter, supernatant leaving the bioreactor was collected into a container at 0° C. to minimize inactivation. Initial experiments with the PA.SVNLZ producer cell line cultured in the packed-bed bioreactor operated in fed-batch mode showed comparable vector production by end-point titer and transduction efficiency to that in tissue culture flasks. Next, the packed-bed bioreactor was operated in perfusion mode and compared to a roller bottle operated in fed-batch mode (Table 6). Sampling of supernatants from the bioreactor or roller bottles began one day after cells were seeded. In both cultures, incubation was initially at 37° C. and lowered to 32° C. after 50 hours. The cells in both cultivation systems reached confluency after approximately 100 hours of incubation. Transduction efficiencies achieved with supernatants produced in the packed-bed bioreactor were greater than those from roller bottle cultures (FIG. 10A). However, supernatants produced in the packed-bed bioreactor had lower end-point titers than supernatants from the roller bottle (FIG. 10B) possibly due to the shorter residence time of the medium in the reactor (5.75 hours compared to 24 hours for the roller bottle). Over a 5 day period a total of 10 L of supernatant was collected using the packed-bed bioreactor, compared to 1 L from the roller bottle.

TABLE 6

Operating Parameters of Different Production Systems

| Parameter | Packed Bed Bioreactor* | Roller Bottle+ |
|---|---|---|
| Surface Area (cm$^2$) | 12,000 | 1,700 |
| Volume (ml) | 500 | 200 |
| Mode of Operation | perfusion | fed-batch |
| Dilution Rate (Vol./day) | 4.2 | 1.0 |
| Total Production Vol. (ml) | 10,000 | 1,000 |
| Seeding Density (cells/ml) | $6.5 \times 10^5$ | $2.3 \times 10^5$ |
| Final Density (cells/ml) | $5.91 \times 10^6$ | $9.06 \times 10^6$ |
| End-Point Titer (cfu/ml) | $1.45 \times 10^6$ | $2.40 \times 10^7$ |
| Transduction Efficiency (%) | 36.0 | 29.5 |

*10 g of Fibercell discs in bench-top New Brunswick Scientific bioreactor
+Corning expanded surface area roller bottle

EXAMPLE 4

Comparison of Vector Production from ProPak-A and PA317 Cells Supernatant Production from Bioreactor 10 g of the New Brunswick Scientific Fiber Cell disks (catalog #M 1176-9984) were placed into the spinner basket of the packed-bed bioreactor (catalog #M1222-9990) and washed several times with PBS before autoclaving. Prior to seeding, the bioreactor and Fibercell discs were washed twice in medium containing 5% FBS.

The reactor was seeded with 2.4 to $3.6 \times 10^8$ producer cells (same for ProPak and PA317) in a total volume of 500 ml of medium (i.e. 2 to $3 \times 10^4$ cells/cm$^2$) (DMEM with 5% to 10% FBS). The agitation rate upon seeding was set at approximately 80 rpm. A minimum of 3 hours was required for all of the cells to become attached to the Fibercell discs.

Figure 11:
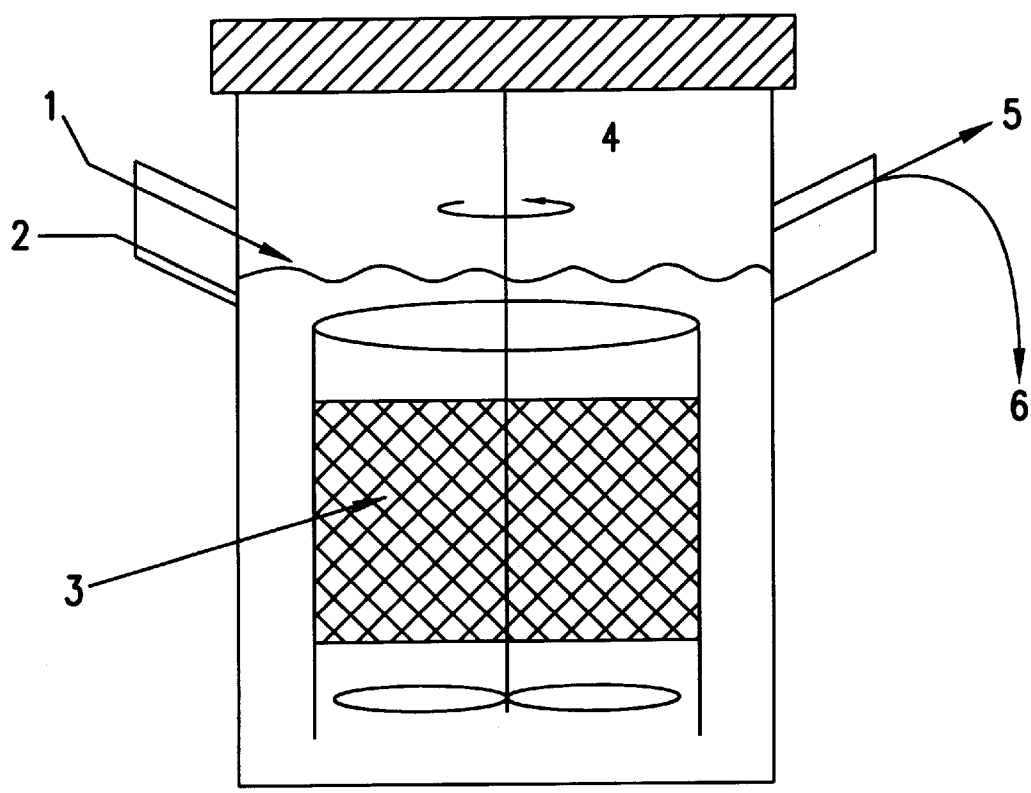
FIG. 11 illustrates a bioreactor that is suitable for the production of retroviral vector supernatant. The numbers indicate the following: 1: medium inlet from 10 L vessel; 2: air inlet medipure air/5% $CO_2$; 3: Fibercell discs 10 g; 4: agitation rate 80 rpm seeding, 250 rpm production; 5: medium outlet: to 2 L vessels on ice; and 6: supernatant samples.
Figure 12:
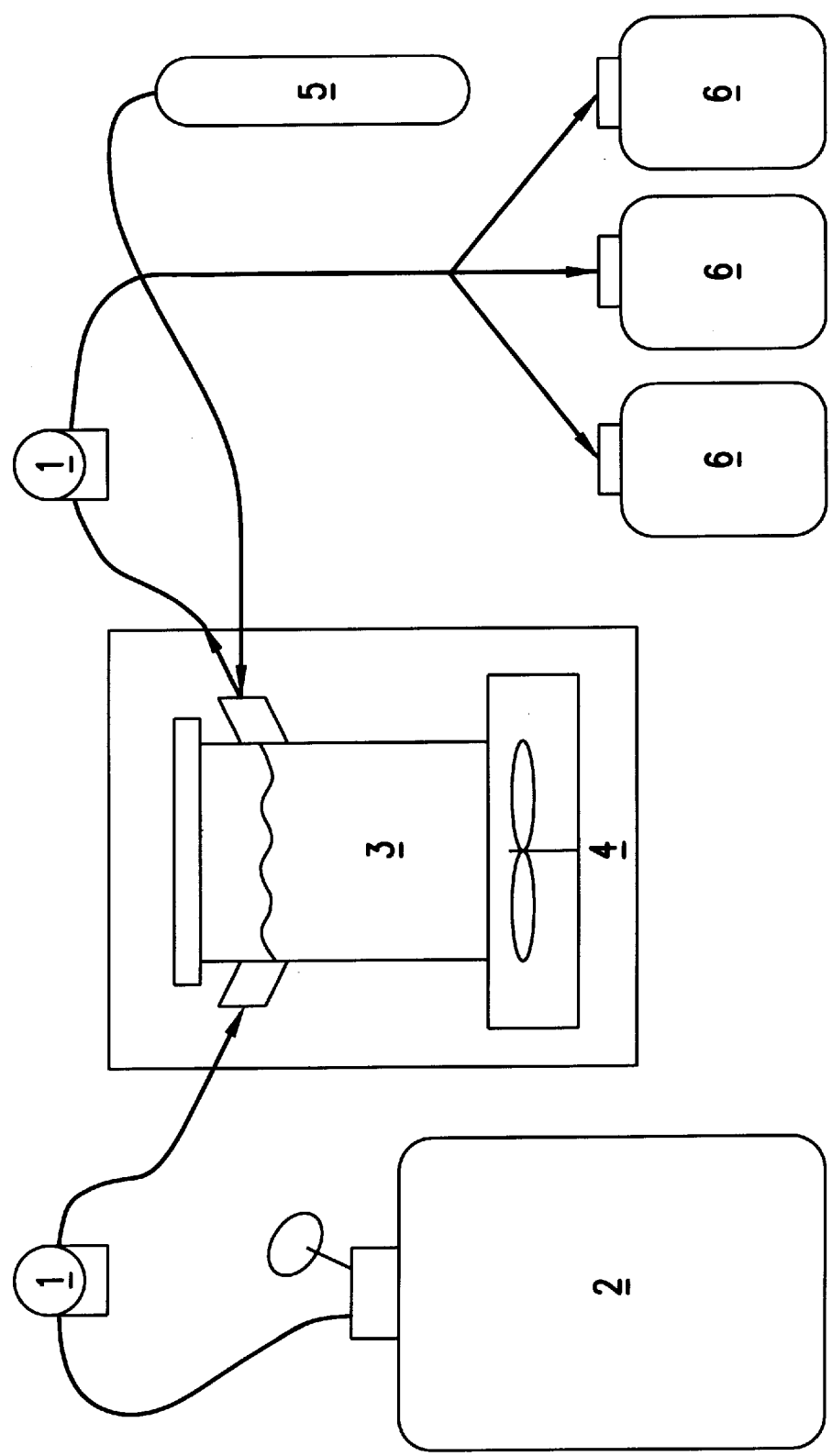
FIG. 12 illustrates the set up of a continuous perfusion packed-bed bioreactor that is suitable for the production of retroviral vector supernatant. The parts of the set-up are indicate by numbers as follows: 1, peristaltic pump; 2, medium feed tank (10 L); 3, packed bed bioreactor (500 ml); 4, magnetic stirrer; 5, air/$CO_2$ mix; 6, 2 L vessels for daily supernatant collection maintained at 0° C. Incubator temperatures are at 37° C. for growth of the producer cells and at 32°–37° C. for vector production.

Approximately 4 to 18 hours after seeding, 50% of the medium was exchanged, and 5 ml of Pluronic F68 (Sigma cat# P5556) was added to the bioreactor to a final concentration of 0.1%. At this time aeration was initiated by gently sparging medical grade air/5% $CO_2$ mix (Altair cat#39222) into the reactor through a 0.2 mm filter. Agitation was increased to approximately 250 rpm. Cells were allowed to grow for three days at 37° C. and then the temperature was lowered to 32° C. Medium exchanges should be performed on the cells every 4 to 12 hours, or the reactor operated in perfusion-mode. The perfusion rate was 2 to 6 reactor volumes per day. Perfused supernatant harvested from the bioreactor was collected into 2 L glass vessels (vented cap) kept on ice. The harvested supernatant was filtered through a 0.45 µm filter, aliquoted, and snap frozen in MeOH/dry ice. Snap-freezing can be performed in other ways such as in liquid nitrogen. The bioreactor and set-up of the continuous perfusion operation are shown in FIGS. 11 and 12.

Supernatant Preparation from Roller Bottles

Producer cells were seeded at $3 \times 10^4$ cells/cm$^2$ in 0.25 ml of DMEM plus 5% FBS per cm$^2$ of surface area. The rotational speed was set at 0.6 rpm. Cells were grown at 37° C. for two days. On day three the temperature was decreased to 32° C. The medium was aspirated and replaced with fresh DMEM medium plus 5% FCS (0.2 ml/cm$^2$ of surface area). Medium was added with a pipette to the bottom of the flask to prevent cells from peeling off and to avoid bubble formation and cell contact. The serum level may be lowered to 2% FBS.

For PA317-based producers, two batches of medium were collected every day (every 12 hours) and pooled to make a single lot. For ProPak-A based producers, supernatants were collected every 12 to 24 hours. Each batch was filtered through a 0.45 µm filter immediately, and kept at 4° C. until batches were pooled (preferably no longer than about 12 to 24 hours). The pooled batches were aliquoted, snap frozen, and stored at −80° C. Supernatant collection can continue as long as producer cells are healthy.

Figure 13:
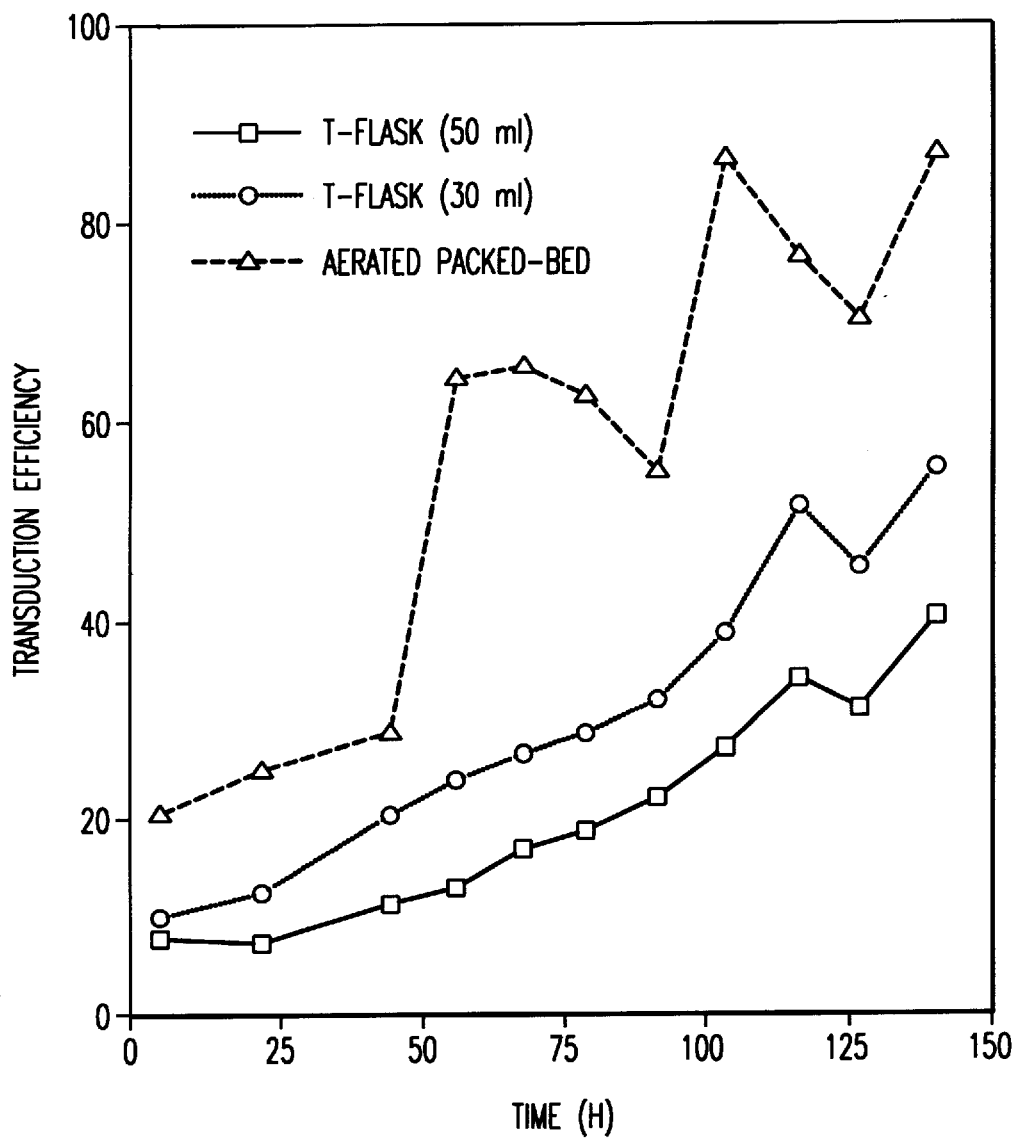
FIG. 13 show the results of the comparison of vector production from ProPak-A.855 producer cells in T-flasks versus aerated packed-bed bioreactor, and as measured on 293 cells. Time (h) is in hours. Transduction efficiency is presented as the percentage of cells expressing the vector-encoded surface marker protein. See FIG. 2 for structure of vector PG855.
Figure 14:
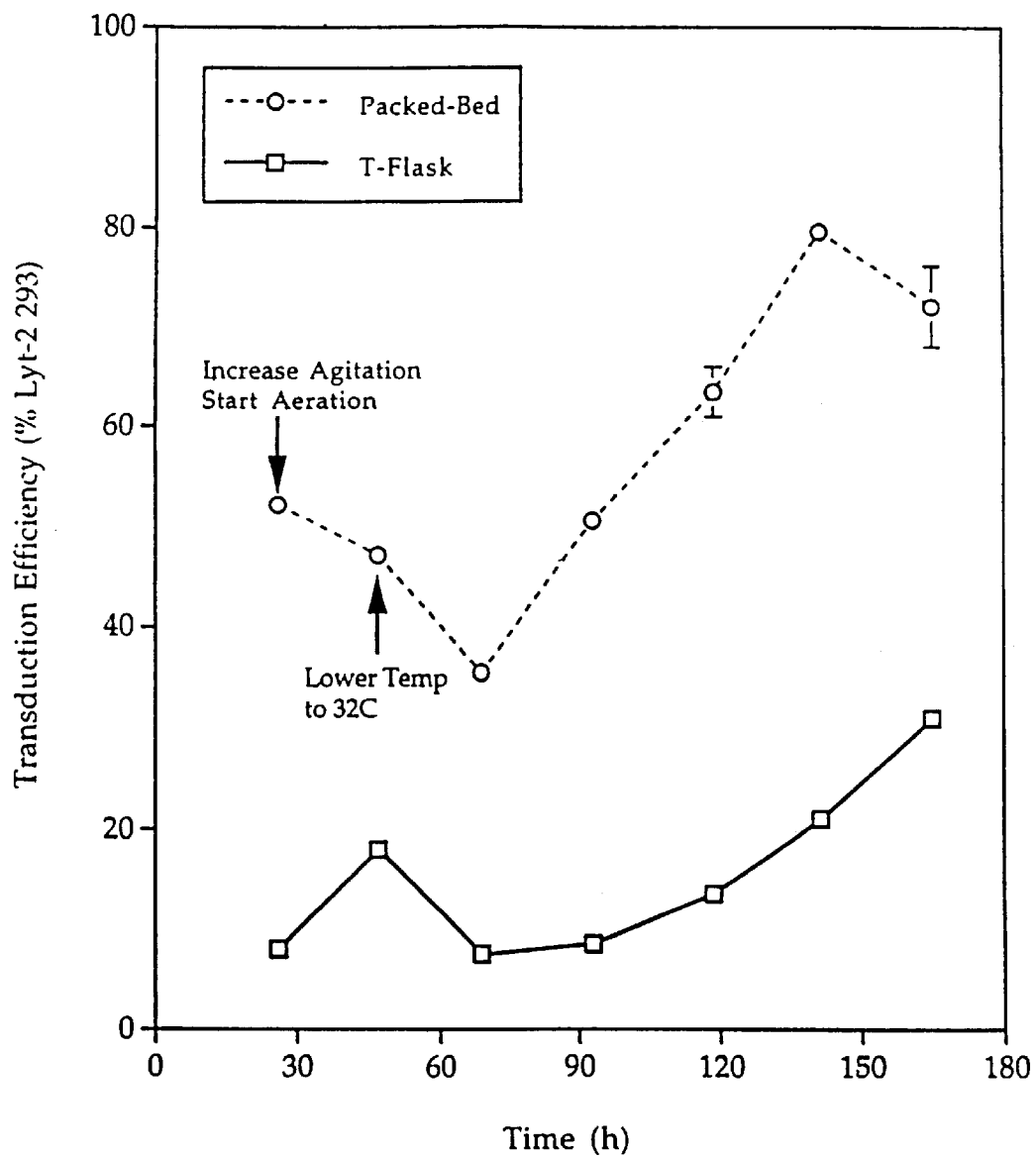
FIG. 14 shows transduction of 293 cells with ProPak-X-derived supernatants harvested at different times post seeding of cells in either a T-flask or the packed-bed bioreactor.
Figure 15:
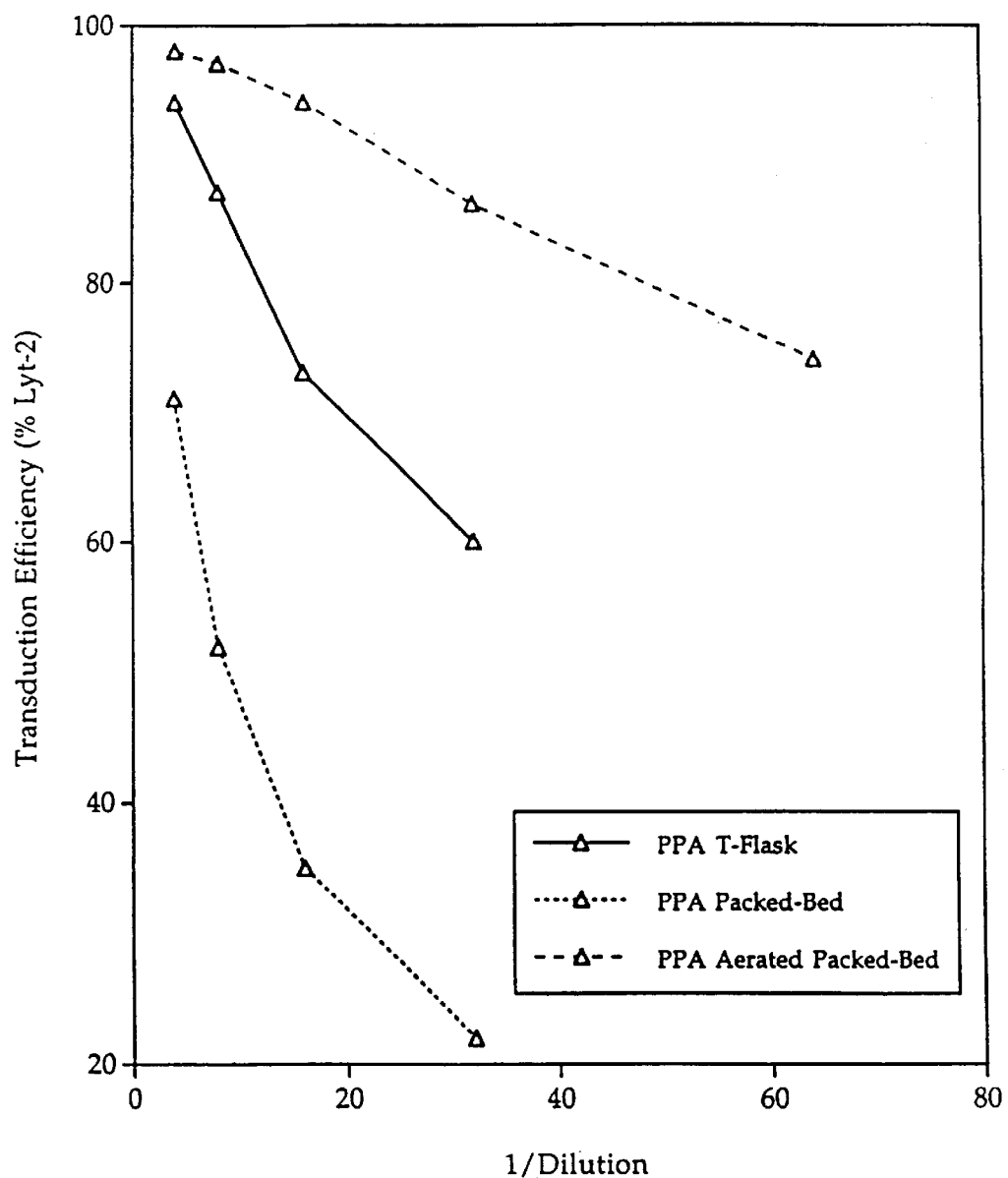
FIG. 15 is a comparison of transduction efficiency achieved with supernatants harvested from ProPak-A.LMiLy cells cultured in different vessels, as shown.

FIG. 13 shows the comparison of vector production from ProPak-A cells culture in T-flasks and in the packed-bed bioreactor with aeration as assayed on 293 cells. The supernatant produced using the packed bed bio-reactor mediates considerably higher transduction than that produced in T-flasks. FIG. 14 shows that ProPak-X cells also produced higher transduction efficiency supernatant when cultured in the packed-bed bioreactor compared to T-flasks. Dilution of vector supernatant produced by ProPak-A under different culture conditions is shown in FIG. 15. Again, the aerated packed-bed bioreactor produced higher quality vector supernatants as determined by transduction efficiency.

EXAMPLE 5

Primary Cell Transductions

Cell selection and analysis

Aphaeresed samples were obtained with informed consent from multiple myeloma or breast cancer patients. Stem cells were mobilized into the peripheral blood by treatment with cyclophosphamide (Cytoxan) and GM-CSF (multiple myeloma), G-CSF above (breast cancer), or Cytoxan+VP-16+CDDP+G-CSF (breast cancer). Apheresis for total white cells was started when the peripheral blood white cell count was greater than 500 cells/ml and the platelet count was greater than 50,000 cells/ml. Patients were apheresed daily until $6 \times 10^8$ mononuclear cells (MNC) were collected.

The cells were washed twice in PBS (partially depleting platelets), and CD34+ cells were positively selected using a Baxter Isolex™ cell selector. The recovered cells averaged 85% to 99% CD34+ purity as determined by FACS analysis.

Transduction

CD34$^+$ cells ($0.5 \times 10^6$) were suspended in 0.5 ml of freshly thawed retroviral supernatant and diluted 1:1 in Whitlock/Witte medium (50% IMDM, 50% RPMI 1640, 10% FCS, $4 \times 10^{-5}$ M 2-mercaptoethanol, 10 mM HEPES, 100 µ/ml penicillin, 100 mg/ml streptomycin, and 4 mM glutamine) containing cytokines at the following final concentrations: c-kit ligand (Amgen) 100 ng/ml or leukemia inhibiting factor (LIF, Sandoz); IL-3 (Sandoz) 20 ng/ml; IL-6 (Sandoz) 20 ng/ml. Protamine sulfate was added at a final concentration of 4 µg/ml or polybrene was added at a final concentration of 8 µg/ml. The cells and vector were centrifuged at 2800×g, 33° C. to 35° C., for three hours. The cells were resuspended in medium with cytokines and cultured for three days. After three days, cells were harvested and approximately $4 \times 10^5$ cells used to determine bulk transduction efficiency, and plated in methylcellulose to determine progenitor cell transduction efficiency (see below).

Figure 16A:
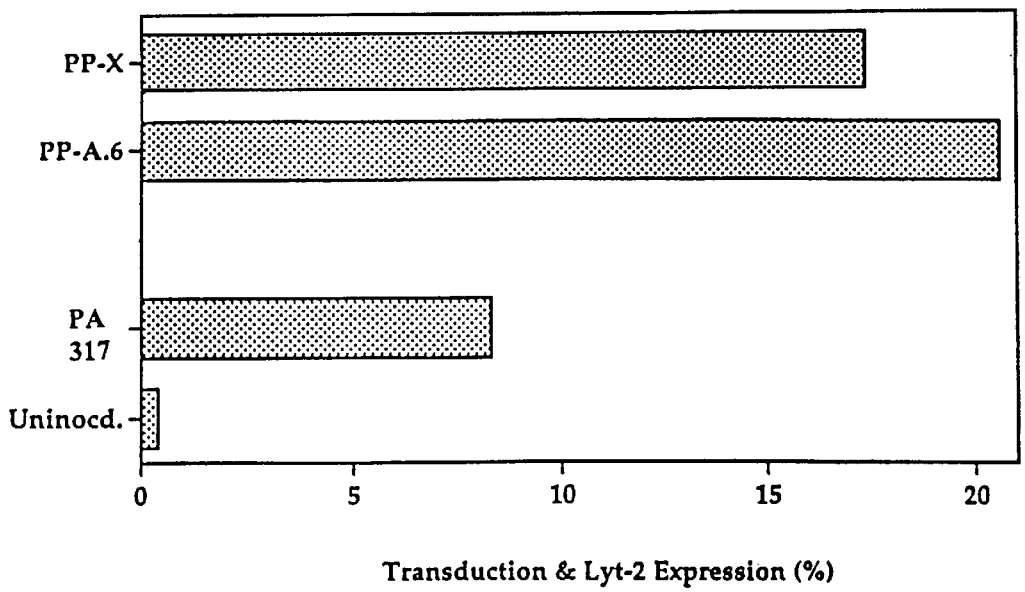
FIGS. 16A and 16B shows transduction of bone marrow (CD34$^+$) with LMiLy packed-bed supernatants.
Figure 16B:
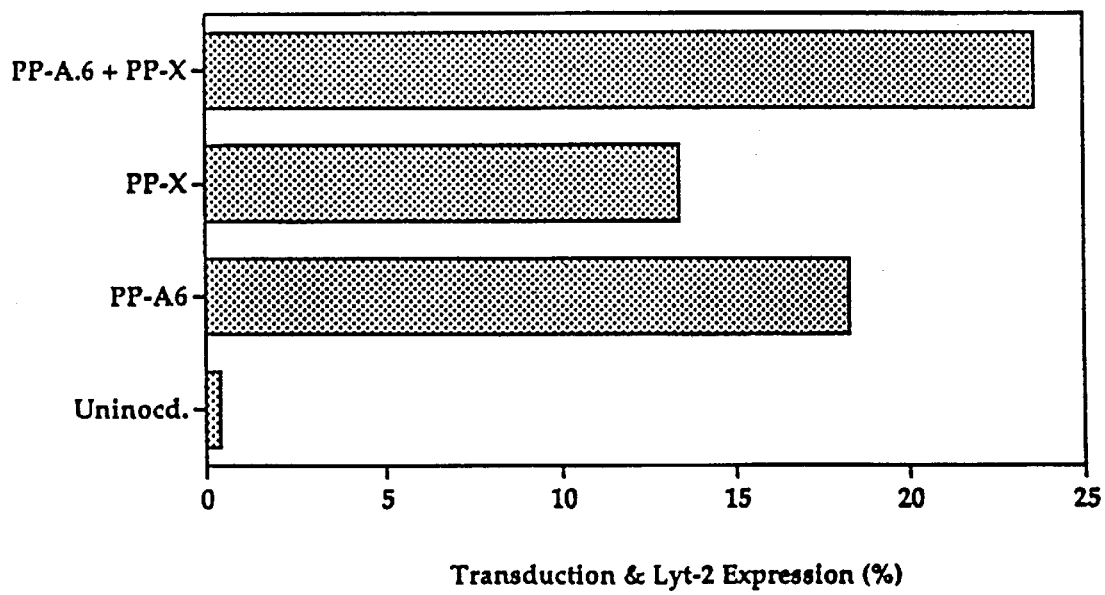

For the LLySN and LMily vectors, which contain the murine Lyt-2 marker gene, bulk transduction efficiency was determined by staining with APC or PE conjugated anti-Lyt-2 (Pharmingen) and sulfurhodamine conjugated anti-CD34. The results are shown in FIGS. 16A and 16B. Vector supernatant from either ProPak-A or ProPak-X transduced primary human cells with greater efficiency than that from PA317 cells. Furthermore, the combination of amphotropic and xenotropic vector can be useful to deliver two vectors to the same cell since they do not compete for the same receptor.

Methylcellulose assay

Cells from each transduction ($2.5 \times 10^3$ to $10 \times 10^3$) were added to 4 ml of methylcellulose medium (Stem Cell Technologies) plus 1 ml IMDM containing the following cytokines (final concentration): c-kit ligand 100 ng/ml; GM-CSF (Amgen) 10 ng/ml; IL-3 10 ng/ml; IL-6 10 ng/ml; rhEPO (Amgen) 2 units/ml. 1.0 ml of the cell/cytokine methylcellulose mixture was plated onto five 35 mm plates using a 5 ml syringe and 16 gauge needle, and the plates were placed in a 37° C. incubator for 2 weeks.

After 14 days, single methylcellulose colonies were picked and analyzed for the presence of neo or RevM10 by PCR.

Analysis

Individual colonies were picked by aspiration in 5 µl and transferred to 25 µl to 50 µl of PCR lysis buffer. PCR lysis buffer is a 1:1 mixture of buffer A (100 mM KCl, 10 mM Tris pH 8.2, 2.5 mM $MgCl_2$) and buffer B (10 mM Tris pH 8.3, 2.5 mM $MgCl_2$, 1% Tween 20, 1% NP40, 100 µl/ml proteinase K). The mixture was allowed to incubate overnight at 37° C. or for 2 h at 56° C. The proteinase K was inactivated by heating at 94° C. for 10 to 30 minutes, and 5–10 µl of the lysate was used for the PCR reaction.

The PCR reaction amplified a 100 bp fragment of the β-globin gene and either a 240 bp fragment of the neo gene or a 180 bp fragment of RevM10, depending on the vector used. The primers used were as follows.

| | | |
|---|---|---|
| Rev: | 5'TCgATTAgTgAACggATCCTT 3' | (SEQ ID NO: 5) |
| | 5'CTCCtgACTCCAATATTgCAg 3' | (SEQ ID NO: 6) |
| Neo: | 5'TCgACgTTgTCACTgAAgCg 3' | (SEQ ID NO: 7) |
| | 5'gCTCTTCgTCCAgATCATCC 3' | (SEQ ID NO: 8) |
| Beta-globin: | 5'ACACAACTgTgTTCACTAgC 3' | (SEQ ID NO: 9) |
| | 5'CAACTTCATCCACgTTCACC 3' | (SEQ ID NO: 10) |

The reactions were performed in a 40 µl final volume in a Perkin Elmer thermal cycler 9600 as follows: 5 min denaturation at 94° C.; 40 cycles of 30 sec at 94° C., 30 sec at 62° C., 1 min at 72° C.; and 10 min at 72° C. PCR products are visualized by ethidium bromide agarose gel electrophoresis (Sambrook et al. (1989) supra) and the PCR products confirmed by Southern blot hybridization. A sample was considered positive if both the Rev or neo band and the β-globin band were present. The results, summarized in Table 7, show that for two different tissues (MPB and ABM), the ProPak supernatants performed better than the PA317 supernatants.

The results in FIG. 16A show that both the xenotropic ProPak-X (X.36) and the amphotropic ProPak-A.6 were able to produce retroviral vector preparations which transduced human hematopoietic stem/progenitor cells with higher efficiency than that produced from PA317 cells.

TABLE 7

METHYL CELLULOSE DATA - CD34+ CELLS
(Number of Colonies)

| TISSUE | LABEL | PACKAGING CELLS | VECTOR | TESTED | POSITIVE | TRANSDUCTION EFFICIENCY (%) | PCR TARGET SEQUENCE |
|---|---|---|---|---|---|---|---|
| MPB | Ampho | PA 317 | LLySN | 24 | 4 | 17 | neo |
| MPB | Xeno | PP-X.36 | LLlySN | 24 | 7 | 29 | neo |
| MPB | Ampho | PP-A.6 | LLySN | 24 | 11 | 46 | neo |
| ABM | Ampho | PP-A.6 | LMiLy | 56 | 13 | 23 | rev |
| ABM | Ampho | PA 317 | LMiLy | 56 | 4 | 7 | rev |

Key:
MPB: Mobilized peripheral blood
ABM: Adult bone marrow from a cadaver
neo: Neomycin
rev: Rev M10

The following series of examples describe the generation of high quality vector supernatants with MLV-xenotropic, MLV-amphotropic or GaLV envelope and the ability of these different enveloped vectors from human or murine-based packaging cells to transduce primary human hematopoietic cells. The complementary tropisms and safety of the ProPak-A and ProPak-X cell lines were also exploited to produce vector supernatants by co-culture. It was demonstrated that after inoculation of hematopoietic stem and progenitor cells (HSPC) with co-culture supernatants containing both amphotropic and xenotropic vector particles, 100% of the colony-forming progeny contained transgene. Expression of transgene in cells with a phenotype characteristic of hematopoietic progenitor cells was also demonstrated.

EXAMPLE 6

Derivation of Packaging Cells

To facilitate derivation of packaging cell lines with a variety of envelopes, a cell line expressing the MLV Gag-Pol functions was first constructed. The gag-pol gene was expressed from the MMLV-LTR promoter, the CMV-IE promoter, or the Rous Sarcoma Virus LTR (FIG. 1). The gag-pol open reading frame (ORF) (Rigg et al., (1996) supra) was sub-cloned into the expression vector PMLV*. This plasmid was derived from pCMV* (Rigg et al. (1996) supra) by replacement of the CMV promoter with the MLV LTR (M-LTR) promoter. The envelope protein ORF's were sub-cloned into the restriction sites shown in plasmid pCI (Promega, Madison, Wis.) which contains the cytomegalovirus immediate early promoter (CMV-IE), a chimeric intron (SD/SA), and the simian virus 40 late polyadenylation sequence (pA).

The xenotropic envelope (Ex) gene was obtained by PCR from a linear template derived from plasmid pXeno (O'Neill et al. (1985) J. Virol. 53:100–106) using the following oligonucleotide primer pair:

5'-ACCTCGAGCCGCCAGCC<u>ATG</u>GAAGGTTCAGCGTTCTC-3'
(SEQ ID NO: 11)
and
5'-AATCTAGAC<span>tta</span>TTCACGCGATTCTACTTC-3'
(SEQ ID NO: 12).

The underlined ATG corresponds to nucleotides 291 to 293, and lower case letters denote the stop codon, nucleotides 223 to 225 (O'Neill et al. (1985) supra).

The chimeric envelope (Eax) gene was constructed by replacing the sequence between the Apa I and Bgl II sites of the amphotropic envelope gene (nucleotides 772 to 963; Ott et al. (1990) J. Virol. 64: 757–766) with a synthetic DNA corresponding to the sequence of the xenotropic envelope gene from 10A1 (nucleotides 801 to 965; Ott et al., (1990) supra).

Plasmids encoding Gag-Pol were cotransfected into 293 cells which are free of MLV-like sequences, which are free of endogenous MLV-like sequences (Rigg et al. (1996) supra). Transient Gag expression was detected by ELISA in all cases, but it was only possible to isolate clones stably expressing Gag at levels equivalent to the ProPak-A.6 cells (Rigg et al. (1996) supra) with the MLV-LTR driven Gag. Transient cotransfection with vector and envelope plasmids of the 293/Gag-Pol cells (called ProGag) yielded higher titer supernatants than cotransfection of Anjou cells (Pear et al. (1993) Proc. Natl. Acad. Sci. USA 90: 8392–8396).

Next, expression plasmids bearing the genes for the xenotropic (Ex, FIG. 1) or amphotropic (Rigg et al., (1996) supra) envelope proteins were stably introduced into ProGag cells, and clones expressing either xenotropic (called ProPak-X) or amphotropic (ProPak-A.52) envelope proteins were isolated by flow cytometry. In turn, the vectors LLySN and LMiLy (FIG. 2) were transduced into these cells, and the resulting producer cells were used to generate the supernatants used in this study.

Retroviral vectors LMiLy and LLySN have been described (Rigg et al. (1995) supra and Rigg et al, (1996) Virol. 218: 290–295). LMiLy and LLySN encode the Lyt2 surface antigen (Ly) (Tagawa et al., 1986) Proc. Natl. Acad. Sci. USA 83: 3422–3426) expressed either directly from the retroviral LTR (L) promoter in LLySN, or via an internal ribosomal entry site (i) in LMiLy. The packaging (psi) sequence in LMiLy is to nucleotide 566 (Shinnick et al., (1981) Nature 293: 543–548), and LLySN has the longer psi sequence and non-functional ATG (Bender et al., (1987) J. Virol. 64: 1639–1646; Miller and Rosman, (1989) Biotechniques 7: 980–990), and also contains the neomycin phosphotransferase gene (N) expressed from an internal SV40 promoter (S). Unless indicated otherwise, LLySN supernatants were prepared in T-flasks from G418 resistant cell populations, and LMiLy supernatants were prepared from producer cell clones in the sparged packed-bed bioreactor.

In contrast to Ex and Ea envelopes (FIG. 1), no cells stably expressing either the chimeric Eax (FIG. 1) or GaLV envelope proteins could be isolated in repeated attempts since cell lysis resulted. While transient supernatants could be prepared by co-transfection of ProGag cells with the Eax and vector expression plasmids, no stable expression of the Eax envelope was achieved in 293, ProGag or HT1080 cells. Most dramatic was transfection of the GALV envelope-encoding plasmid which resulted in total lysis of ProGag or 293 cell cultures within 24 hours. Transient GaLV supernatants could not be produced with cotransfected ProGag cells although the GaLV envelope gene was functional, since vector particles were released if murine cells were cotransfected.

EXAMPLE 7

Determination of Tropism

Figure 20A:
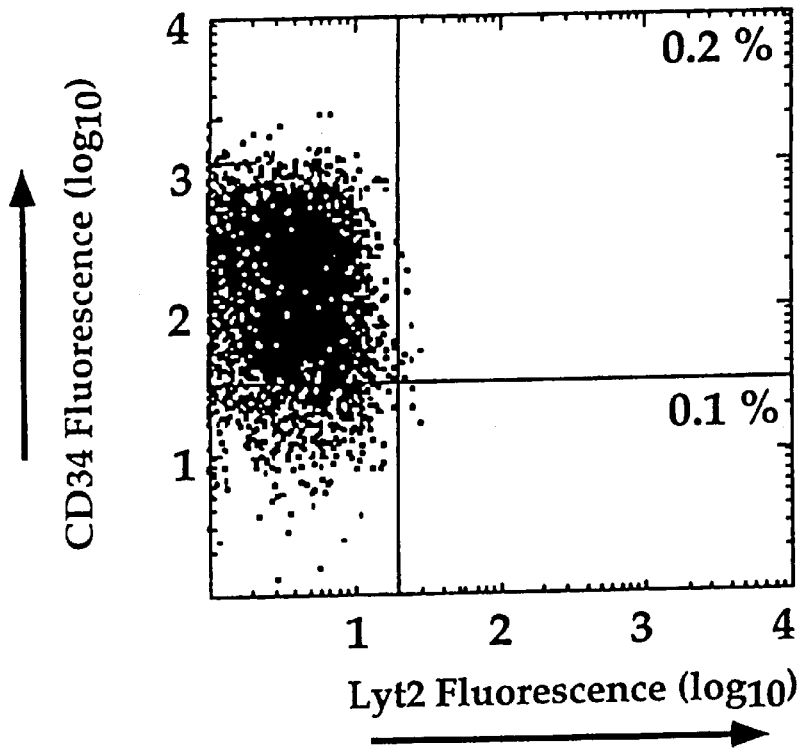
FIG. 20 shows phenotypic analysis 3 days after spinoculation of CD34-positive cells. Cells were stained with anti-Lyt2-phycoerythrin antibody, and either anti-CD34-sulphur rhodamine (panels A and B) or a panel of fluorescein isothiocyanate-labeled, lineage-specific antibodies (panels C and D). The panel of lineage-specific antibodies contained antibodies to the following hematopoietic cell lineages: thymocytes (CD2); granulocytes, monocytes and macrophages (CD14, CD15); natural killer cells (CD16); B lymphocytes (CD19); and erythrocytes (glycophorin). Samples were analyzed on a Becton-Dickinson Vantage flow cytometer. Panels A and C are from uninoculated, and panels B and D from inoculated cells. The values represent the proportion of the cell population in the respective quadrants.
Figure 20B:
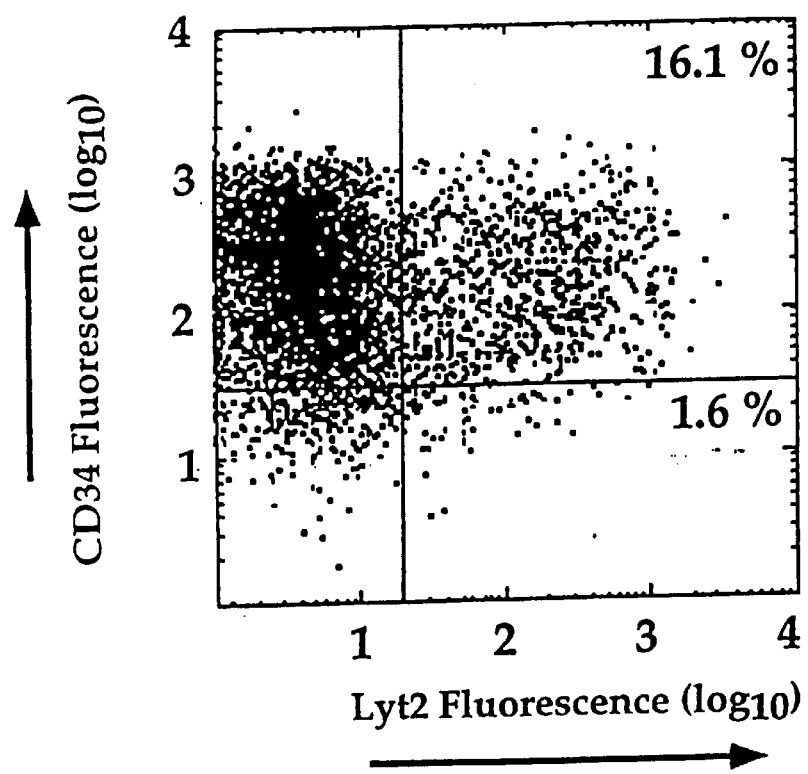
Figure 20C:
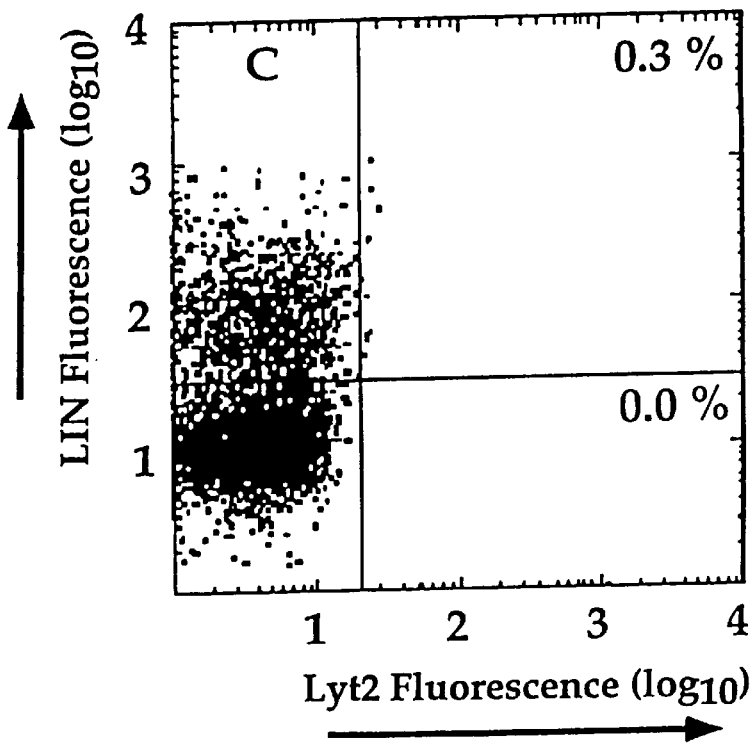
Figure 20D:
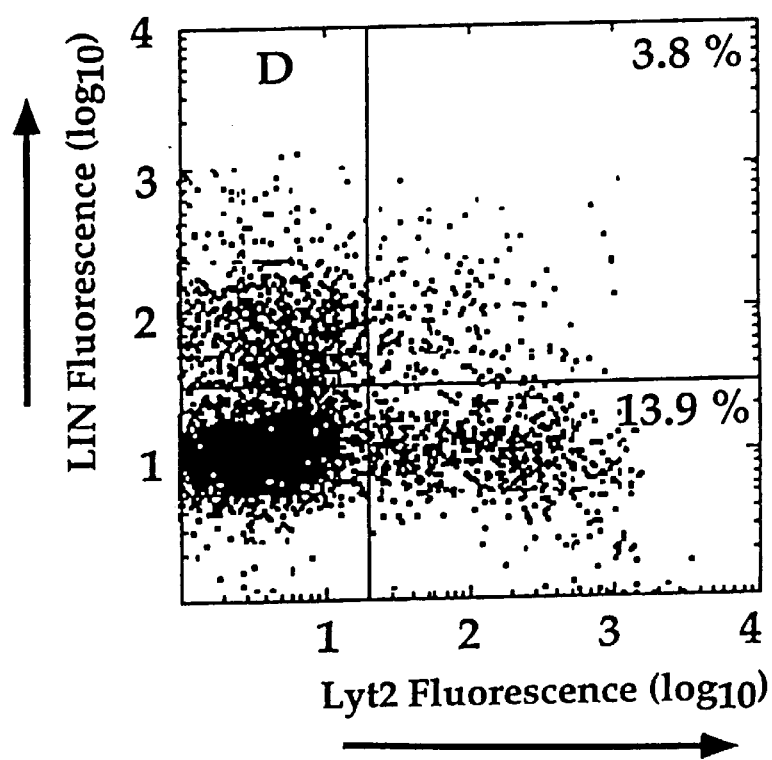

To confirm the phenotype of vector particles bearing the amphotropic, xenotropic or chimeric ampho/xeno envelope, supernatants were inoculated onto cell lines from different species chosen to distinguish between the various envelope tropisms. Cells were inoculated with vector particles packaged in the new ProPak-X (xenotropic) or ProPak-A.52 (amphotropic) cell lines, or with vector supernatants from cotransfection of vector and the expression plasmid encoding the Eax envelope. For comparison, MLV particles pseudotyped with the GaLV (from PG13 cells) glycoprotein or the G protein of vesicular stomatitis virus (VSV-G, Yee et al., (1994) Proc. Natl. Acad Sci. USA 91: 9564–9568) were also included. The tropism observed for the xenotropic, amphotropic and GaLV envelopes (FIG. 20A) corresponded with those established for retroviruses (Teich, (1984) Cold Spring Harbor Laboratory).

Figure 17A:
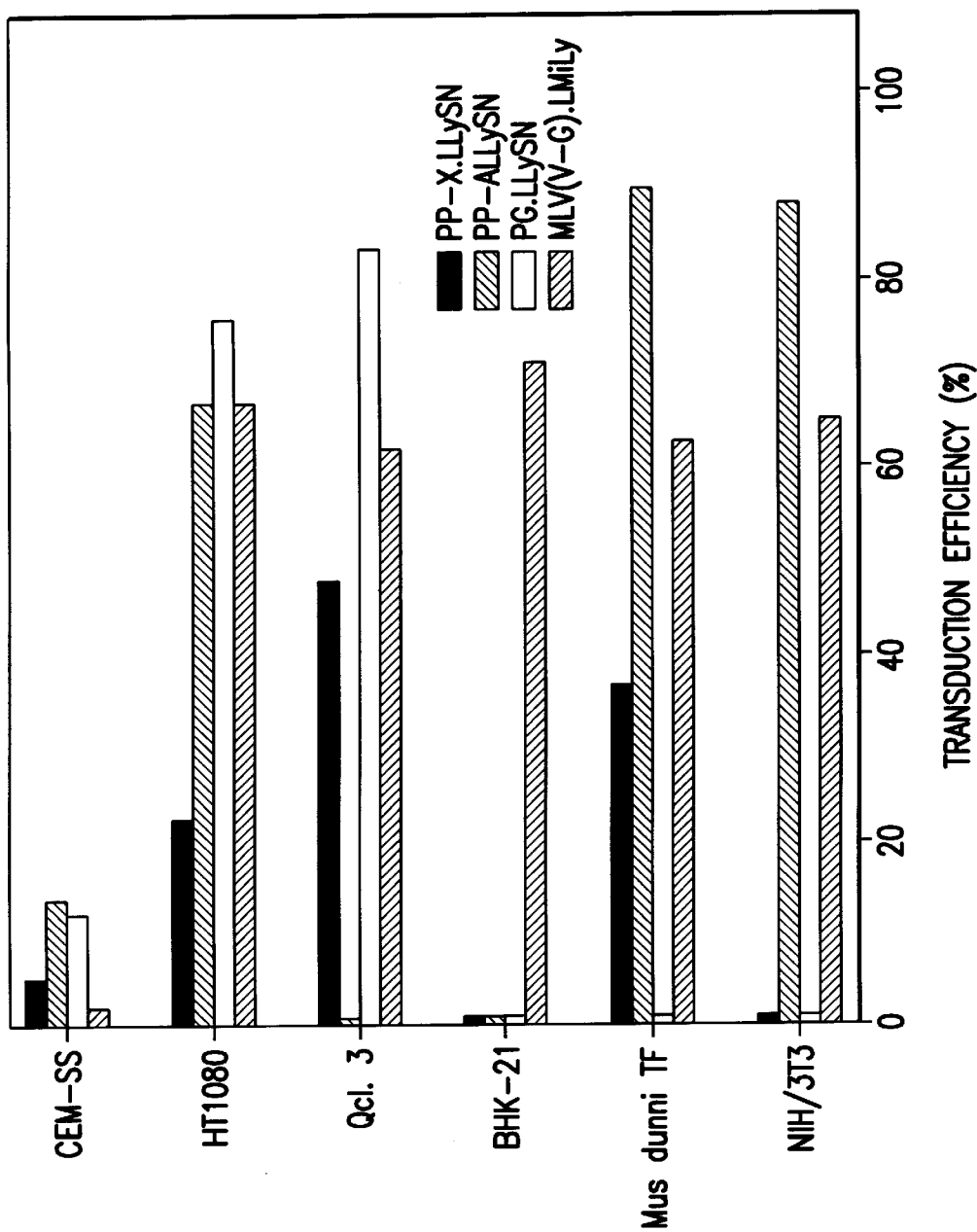
FIGS. 17A and 17B show transduction of cell lines with Lyt2-encoding vector preparations with various tropisms. Average values for duplicate samples are plotted.
Figure 17B:
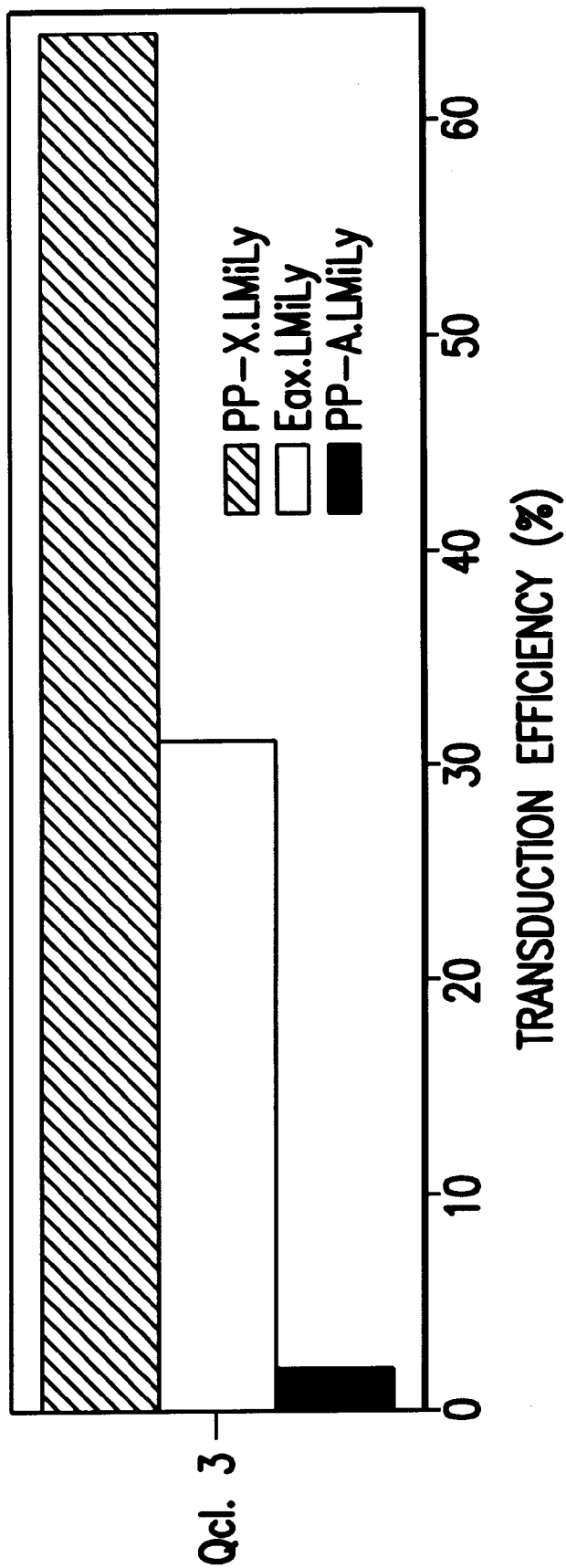

By analogy to the genotype and receptor tropism of MLV-10A1 (Ott et al., (1990) supra; Wilson et al., (1994) J. Virol. 68: 7697–7703; and Wilson et al. (1995) J. Virol. 69: 534–537), the Eax envelope should mediate retroviral vector binding to both the amphotropic and xenotropic receptors. Vector particles bearing the Eax envelope transduced quail cells, which are resistant to amphotropic particles but susceptible to xenotropic vector (FIG. 17B), and also transduced murine NIH/3T3 cells which are resistant to xenotropic vector (FIG. 17A). Therefore, this modification of the amphotropic envelope protein conferred specificity for a cell line that cannot be transduced with amphotropic vector, establishing the extended tropism. As expected, all cell types were transduced with the pantropic MLV(VSV-G) vector particles. Lower transduction efficiencies were achieved with this pseudotype, possibly a result of having to prepare supernatants by transient cotransfection because of the toxicity of the VSV-G protein.

EXAMPLE 8

Resistance to Human Serum

Figure 18:
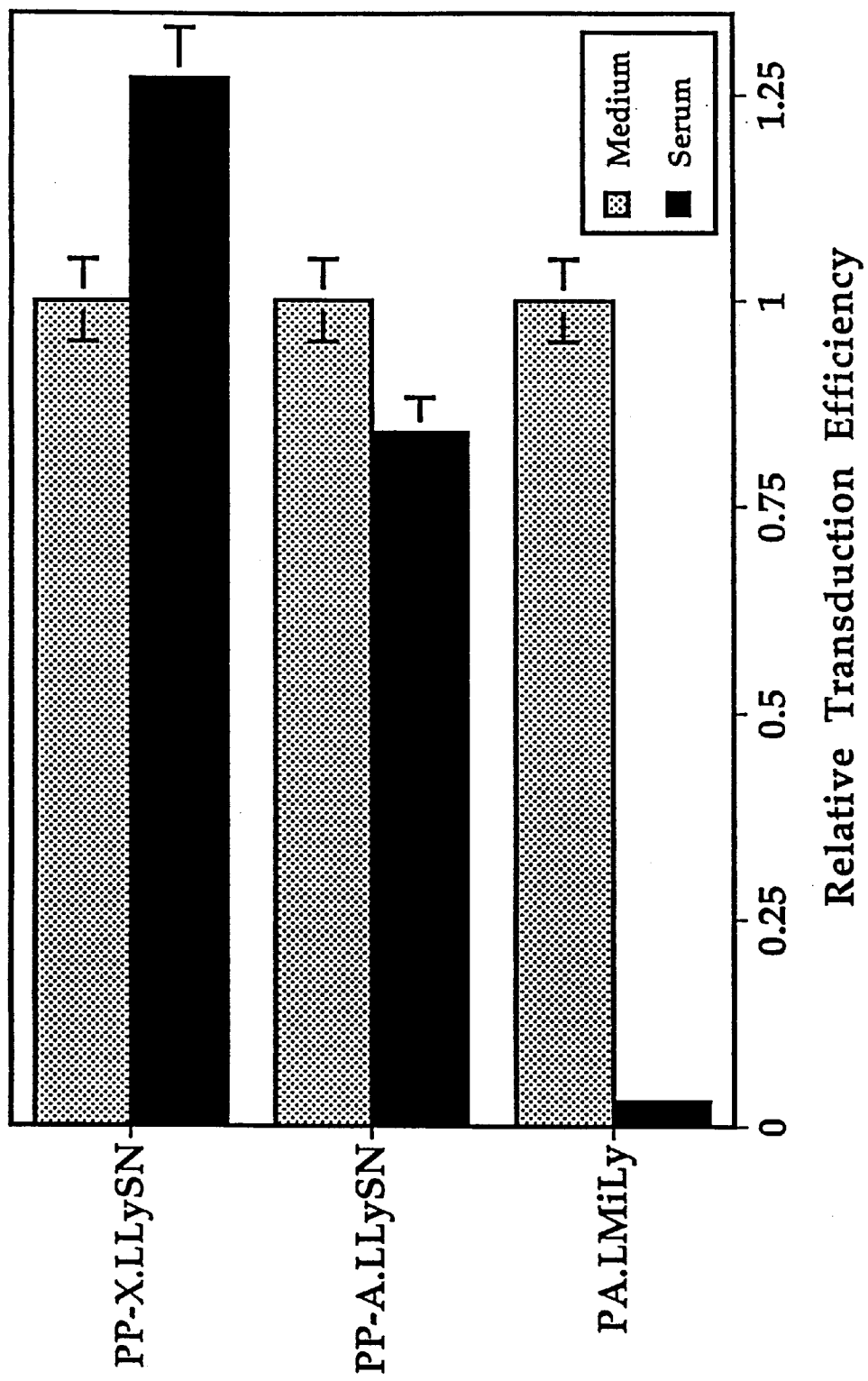
FIG. 18. Complement resistance of vector packaged in ProPak-X, ProPak-A, or PA317 packaging cell lines. Supernatants were incubated for 30 min at 37° C. with an equal volume of human serum. The residual transducing activity relative to samples incubated in medium was determined on 293 (ProPak-X) or NIH/3T3 cells (ProPak-A, PA317). The human serum, a pool from 4 healthy donors, had a hemolytic titer ($CH_{50}$) of 150 to 313 (EZ Complement Assay, Diamedix, Miami, Fla.). Bars represent the range for duplicate samples.
Figure 19A:
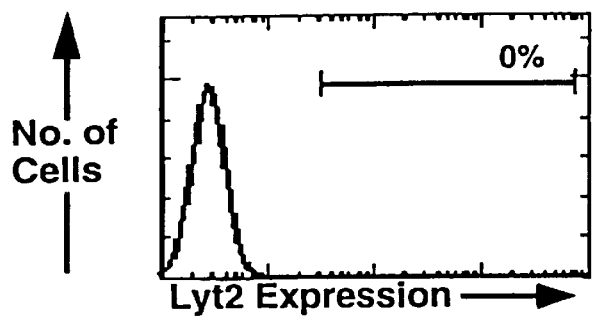
FIG. 19 shows a comparison of vector production methods. ProPak-A.52.LMiLy supernatants were harvested one day after confluence (visual monolayer in T-flask and roller bottle cultures), diluted 1 in 8 and inoculated onto NIH/3T3 cells. Lyt2 expression was analyzed 3 days later by FACS.
Figure 19B:
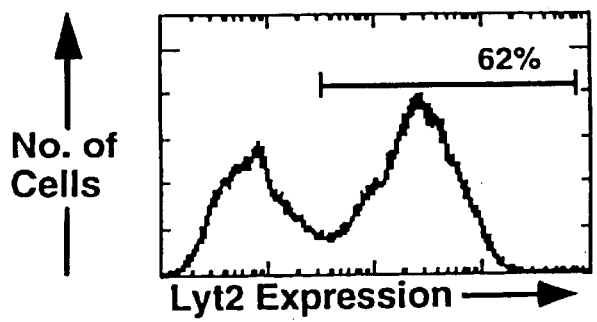
Figure 19C:
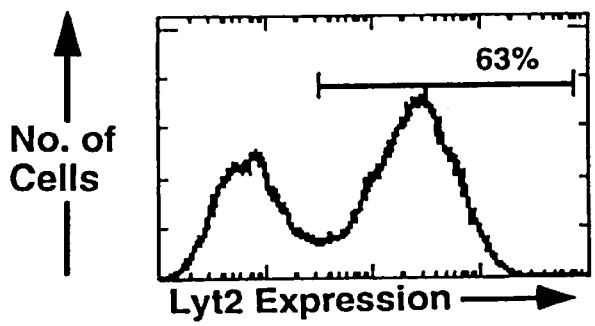
Figure 19D:
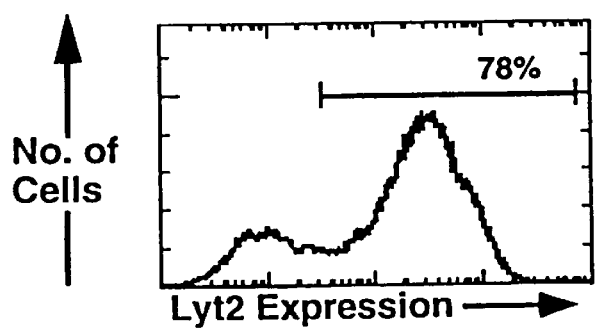
Figure 19E:
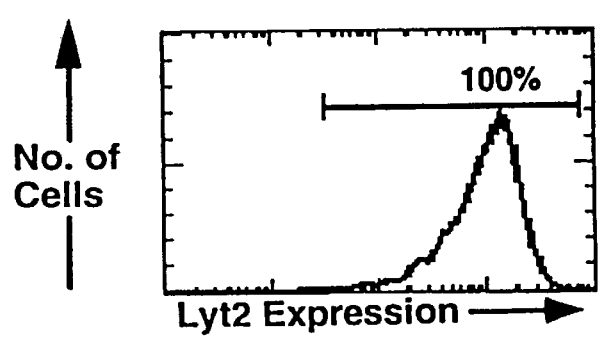

It was shown above that amphotropic and ecotropic particles generated from 293 cells were not inactivated by treatment with human serum under conditions which inactivate amphotropic vector packaged in murine PA317 cells. The xenotropic vector was similarly tested for resistance and the xenotropic particles were found to not be inactivated by treatment with human serum (FIG. 18). Vector particles from the ProPak-A.52 packaging clone were also resistant, while the PA317-packaged vector was almost completely inactivated (FIG. 18), as has been previously demonstrated (Takeuchi et al., (1994) *J. Virol.* 68: 8001–8007; Rigg et al., (1996) supra).

EXAMPLE 9

RCR Generation Test

The Gag-Pol packaging functions in ProPak-X and ProPak-A.52 cell lines are expressed from the MLV-LTR promoter and these cells therefore carry more MLV-derived sequences than the ProPak-A.6 cells. However, generation of RCR due to recombination of MLV-derived sequences is unlikely since a minimum of three recombination events would still be required. Only 32 nucleotides of the R sequence are retained in the LTR promoter used, a relatively short sequence homology with vectors. Nevertheless, cultures and supernatants were stringently tested for RCR. Co-cultures of ProPak-A and ProPak-X cells carrying the vector BC140revM10 were maintained. This vector, as before (Rigg et al., (1996) supra), rapidly generated RCR in PA317 cells (Table 8). Although cultures were maintained for up to 3 months, in no case was RCR detectable either in supernatants or cells from cultures containing ProPak cells (Table 8).

TABLE 8

Tests for RCR in producer cell cultures or co-cultures

| Expt. | Packaging Cell Line(s) | Vector Carried | Supernatant RCR (wk) | Co-culture RCR (wk 12) |
|---|---|---|---|---|
| 1 | PA317 | LMTNL | (>12) | ND |
|  | PA317 | BC140revM10 | 6 | ND |
|  | Pro-Pak-A.52 | LMTNL | (>12) | ND |
|  | ProPak-A.52 | BC140revM10 | (>12) | ND |
|  | ProPak-X | LMTNL | (>12) | ND |
|  | ProPak-X | BC140revM10 | (>12) | ND |
|  | PP-A.52/PP-X* | LMTNL | (>12) | negative |
|  | PP-A.52/PP-X* | BC140revM10 | (>12) | negative |
| 2 | PA317 | BC140revM10 | 6 | ND |
|  | ProPak-A.52 | BC140revM10 | (>12) | negative |
|  | ProPak-X | BC140revM10 | (>12) | ND |
|  | ProPak-A.6 | BC140revM10 | (>12) | negative |
|  | PP-A.52/PP-X* | BC140revM10 | (>12) | negative |

ND: not determined
(>12): no RCR detected 12 weeks after G418-resistant pools established.
*Co-culture of PP-X and PP-A producer cell populations.

Vectors were introduced into the packaging cells by spinoculation at 1400 g with MLV(VSV-G) pseudotype supernatants produced by transient transfection of ProGag cells with vector and VSV-G expression plasmids (Yee et al., (1994) supra). Populations of producer cells were selected for G418 resistance and passaged every 3 or 4 days. RCR was detected by S+L− assay on PG4 cells (ATCC CRL 2032) by inoculation with supernatant from producer cell cultures, or after 3 passages of co-culture with Mus dunni cells (Forestell et al., (1995) supra; Printz et al., (1995) *Gene Ther.* 2: 143–150) in the presence of 2 μg/ml polybrene.

The packaging cell line ProPak-A.52 was deposited with the American Type Culture Collection (ATCC) at 10801 University Blvd., Manassas, Va. 20110-2209, U.S.A. on Feb. 26, 1998, under the provisions for the Budapest treaty for the deposit of Microorganisms for the Purposes of Patent Procedure; the deposit was accorded ATCC Accession No. CRL-12479.

EXAMPLE 10

Improved Retroviral Vector Supernatant Production in a Bioreactor

Applying principles of retroviral vector production defined with PA317-based producer cell lines (Forestell et al., (1995) supra), vector production from ProPak cell lines in a packed-bed bioreactor was investigated. Using the PP-A.52.LMiLy producer cell line, the packed-bed bioreactor operated in fed-batch mode was compared with a roller bottle and T-flask for production of vector supernatant. The effect of supplemental sparging of an air/$CO_2$ mix into the bioreactor was also examined to determine if oxygen transfer from the bioreactor head-space was limiting cell growth and vector production. Supplemental aeration was achieved by direct micro-sparging of a medical grade mix of air with 5% $CO_2$, and 0.01% Pluronic F-68 (Sigma, St. Louis, Mo.) was added to prevent cell damage from shear. Vector supernatants harvested from the different production vessels were compared for their ability to transduce NIH/3T3 cells (FIG. 19). Supernatants harvested from the T-flask and roller bottle cultures yielded transduction efficiencies of 62% and 63% respectively, while supernatant from the non-sparged packed-bed bioreactor yielded a transduction efficiency of 78%. Gene transfer was greatest (100%) with vector produced in the sparged packed-bed bioreactor indicating that head-space oxygen transfer alone was limiting vector production and cell growth in the non-sparged bioreactor. Measurements of the glucose and glutamine concentrations indicated that these key nutrients were not limiting in any of the cultures. In this particular experiment, vector production was also analyzed by measurement of the viral envelope and Gag proteins by ELISA to determine if the improved transduction efficiency was due to increased vector production. Although the final volumetric cell density in the sparged packed-bed bioreactor was slightly lower than in the T-flask ($4.0 \times 10^6$ and $4.7 \times 10^6$ cells/ml respectively), the vector supernatants from the sparged packed-bed bioreactor yielded higher levels of viral protein as well as higher transduction than T-flask supernatants. These results indicated that the improved production in the sparged packed-bed bioreactor was due to increased cell-specific vector productivity.

PA317, PG13, ProPak-A.6, ProPak-A.52, and ProPak-X based producer cell lines were cultured in the packed-bed bioreactor under sparged conditions. In every case, a 2- to 20-fold improvement in vector production was achieved in comparison to T-flask cultures.

In particular, it was determined if the increased gene transfer into cell lines could also be achieved within primary cells. In addition to the higher transduction of NIH/3T3 cells (FIG. 19), ProPak supernatants produced in the sparged packed-bed bioreactor yielded approximately 3-fold higher transduction efficiencies with CD34-positive cells than vector preparations from T-flask cultures (Table 9). Using two different assays (Lyt2 expression in bulk cultures or PCR analysis of CFU-C), different estimates for gene transfer efficiency were obtained; however, the relative numbers were consistent.

TABLE 9

Transduction of CD34-positive cells from MPB (normal donor): comparison of T-flask and packed-bed bioreactor supernatants

| | Transduction Efficiency (%) | | | |
|---|---|---|---|---|
| | T-Flask | | Packed-Bed | |
| Producer Cell Line | Lyt2 Expression | CFU-C Marking | Lyt2 Expression | CFU-C Marking |
| ProPak-A.LMiLy | 1.3 | 5.3 (7/132) | 3.9 | 15.0 (22/147) |
| ProPak-X.LMiLy | 3.8 | 18.1 (27/149) | 9.9 | 43.3 (49/113) |

Cells were inoculated once, and Lyt2 expression was measured 3 days later. Gene marking of CFU-C, determined by PCR, is expressed as a percentage and values in brackets are the number of RevM10-positive colonies divided by the total number that yielded β-globin signals, as described above.

EXAMPLE 11

Primary Cell Transduction with Different Vector Tropisms

This Example compared transduction of CD34-positive hematopoietic progenitor cells or CD4-positive PBL with vectors of different tropisms (amphotropic, xenotropic, GaLV) prepared from stable producer cell lines. Cells were exposed to vector once to directly compare transduction efficiencies which are presented as Lyt2 surface marker expression relative to the expression achieved with PA317-packaged vector preparations (Table 10). Regardless of tropism, all vector types successfully transduced CD34-positive cells isolated from MPB or ABM, or CD4-positive PBL (Table 10). This implies that the receptors for all three vector types are expressed on these cells. While no single vector tropism appeared to mediate significantly higher levels of transduction than any other, the highest transduction efficiencies were achieved with ProPak-A or ProPak-X supernatants (Table 10). Although derived by different means, comparable transduction was achieved with vector from either ProPak-A.6 or ProPak-A.52 clones (Table 10). Also in these comparisons, amphotropic vector supernatants from the human ProPak-A cell lines consistently transduced a higher proportion of target cells than amphotropic vector prepared from PA317-based producer cells (Table 10).

The phenotype of the transduced progenitor cells was determined by flow cytometry. The majority of cells expressing the Lyt 2 gene exhibited a phenotype characteristic of early hematopoietic progenitor cells, that is, CD34 antigen was expressed (FIG. 20, panel B) in the absence of antigens specific for differentiated hematopoietic cell lineages (FIG. 20, panel D).

Since no single tropism appeared to preferentially transduce primary cells, cells were also inoculated with a mixture of vector packaged separately in ProPak-A or ProPak-X cells, to test whether higher transduction could be achieved by simultaneous inoculation with vectors targeting distinct receptors. In all but one of five cases (PP-A & PP-X mix; Table 3) slightly higher transduction was achieved with the mixture (Table 10). It is possible that in these experiments the concentration of vector in the supernatants may be limiting, since individual supernatants were diluted 4-fold in the mixture, compared with 2-fold dilutions where single inocula were used.

TABLE 10

Transduction of primary human hematopoietic cells with vector supernatants of different tropisms from T-flasks (A, LLySN vector) or the sparged packed-bed bioreactor (B, LMiLy vector)

| | Relative Lyt2 Expression | | | |
|---|---|---|---|---|
| Producer Cell Line Base | CD4+ PBL | CD34+ MPB (a) | CD34+ MPB (b) | CD34+ MPB (c) |
| A. T-Flask/LLySN | | | | |
| PA317 | 1.0 | 1.0 | 1.0 | 1.0 |
| ProPak-A.52 | 2.4 | 1.6 | 1.8 | 1.6 |
| ProPak-A.6 | 2.7 | 2.0 | 2.4 | 1.7 |
| ProPak-X | 2.7 | 1.5 | 1.9 | 1.2 |
| PG13 | 2.6 | 1.1 | 1.3 | ND |
| ProPak-A.52 & X mix | ND | 2.0 | ND | ND |

| | Relative Lyt2 Expression | | | |
|---|---|---|---|---|
| Producer Cell Line Base | CD4+ PBL | CD34+ ABM | CD34+ MPB (b) | 34+/Thy-1+ MPB (d) |
| B. Bioreactor/LMiLy | | | | |
| PA317 | 1.0 | 1.0 | 1.0 | 1.0 |
| ProPak-A.5.2 | 3.9 | ND | 2.5 | ND |
| ProPak-A.6 | 3.0 | 2.5 | 3.2 | 1.5 |
| ProPak-X | 5.8 | 2.1 | 2.0 | 1.9 |
| PG13 | 1.2 | 0.7 | 0.9 | ND |
| ProPak-A.52 & X mix | 8.1 | 2.8 | 3.7 | 2.8 |

Transduction of different primary cell types achieved after a single inoculation with supernatants containing the LLySN vector (A), or the LMiLy vector (B). Transduction efficiencies were measured as the proportion of Lyt2-expressing cells, and values have been normalized to that achieved using PA317-based supernatants. Hematopoietic cell populations isolated from six different tissues were inoculated, specifically, CD4+ PBL, or CD34+ cells selected from: ABM or MPB from 2 breast cancer patients (a and c), a multiple myeloma patient (b), or a normal donor (d). ND=not determined.

EXAMPLE 12

Vector Production in Producer Cell Co-Cultures

In attempts to increase the transduction efficiency, vector supernatants were produced from a co-culture of the complementary ProPak-X.LMiLy and ProPak-A.52.LMiLy producer cells in the packed-bed bioreactor. This technique, known as ping-pong amplification, results in higher titers with murine and avian producer cell lines, probably as a result of increased vector copy number (Bodine et al., (1990) Proc. Natl. Acad. Sci. USA 87: 3738–3742; Cosset et al., (1993) Virol. 193: 385–395; Hoatlin et al., (1995) J. Mol. Med 73: 113–120). The problem that has arisen in the past with co-culture production is the generation of RCR (Bodine et al., (1990) supra; Cosset et al., (1993) supra; Muenchau et al., (1990) Virol. 176: 262–265). However, it was already shown herein that no RCR arises during extended co-culture of ProPak-A and ProPak-X cells carrying the BC 140revM10 vector (Table 8), an event that is even less likely with the LMiLy vector which lacks sequences that overlap with the ProPak packaging constructs. Nevertheless, supernatants and end-of-production cells were exhaustively tested and found to be free of RCR by stringent assays (incubation or co-culture with Mus dunni and S+L– assay on PG-4 cells). In addition, the presence of both amphotropic and xenotropic vector particles was confirmed by transduction of permissive and restrictive cell lines.

The ability of PA317, ProPak-A, ProPak-X or ProPak-A/X.LMiLy vector supernatants to transduce CD34-positive cells upon a single spinoculation was first compared. Cell samples were analyzed for Lyt2 expression, and the presence of the revM10 transgene in committed progenitor cells was determined by PCR. Consistent with Lyt2 expression assays (Table 10), supernatants from the human-based ProPak-A or -X producers transduced cells more efficiently than PA317-packaged vector, and the highest level of transduction was achieved with the ProPak-A/X supernatant (Table 11).

Using the ProPak-A/X.LMiLy supernatant, different cytokine combinations and multiple rounds of inoculation were investigated in an effort to maximize gene transfer efficiency. CD34-positive cells were spinoculated with PP-A/X.LMiLy vector once, twice on the same day, or once a day on two consecutive days in the presence of IL-3, IL-6, and either LIF or SCF. Prior to the first spinoculation, cells were incubated for 1 day in 20 ng/ml each of IL-3 and IL-6, and 50 ng/ml SCF or LIF as described above. The results in Table 12 show that while gene transfer was higher in cultures treated with SCF after a single inoculation, gene transfer into CFU-C was 100% for cultures inoculated twice on consecutive days in either LIF or SCF. Furthermore, in both cytokine cocktails the Lyt2 transgene was expressed in up to 40% of the total cell population, and in 35% of the cells which were also CD34-positive.

TABLE 12

Transduction of CD34+ cells from MPB: comparison of inoculation protocol and cytokine cocktail

| | Transduction Efficiency (%) | | | |
|---|---|---|---|---|
| | IL-3, IL-6, LIF | | IL-3, IL-6, SCF | |
| Inoculation Protocol | Lyt2 Expression | CFU-C PCR | Lyt2 Expression | CFU-C PCR |
| once | 13.3 | 51 (47/92) | 14.5 | 74 (68/92) |
| twice, same day | 22.7 | 86 (79/92) | 22.3 | 100 (92/92) |
| twice, consecutive days | 40.4 | 100 (92/92) | 40.4 | 100 (92/92) |

Transduction of CD34+ cells (MPB) with packed-bed bioreactor supernatant from a co-culture of ProPak amphotropic and xenotropic LMiLy producer cells. Cells were spinoculated and incubated as shown in the presence of IL-3, IL-6, and LIF or SCF. Expression of Lyt2 was determined 2 days after the last inoculation, and the marking frequency of individual methyl cellulose colonies (CFU-C) was determined (Table 9).

TABLE 13

Characteristics of the ProPak Cell Lines

| Packaging Cell Line | Tropism | Transduction Efficiency | Human Serum | RCR | Expression Gag-Pol | Plasmids Env |
|---|---|---|---|---|---|---|
| ProPak-X | xenotropic | ≧PG13; PA317 | Resistant | Negative | pMLV*gp | pCl-Ex |
| ProPak-A.52 | amphotropic | ≧PA317 | Resistant | Negative | pMLV*gp | pCMV*Ea |
| ProPak-A.6[1] | amphotropic | ≧PA317 | Resistant | Negative | pCMV-gp | pCMV*Ea |

[1]Rigg et al., (1996) supra.

TABLE 11

Transduction of CD34+/Thy+ cells from MPB: comparison of vector supernatants from different producer cell lines

| | Transduction Efficiency (%) | |
|---|---|---|
| Producer Cell Line | Lyt2 Expression | CFU-C |
| PA317.LMiLy | 2.8 | 12 (27/219) |
| ProPak-A.6.LMiLy | 4.1 | 24 (49/206) |
| ProPak-X.LMiLy | 5.2 | 25 (35/141) |
| ProPak-A.52/X.LMiLy | 7.9 | 36 (65/182) |

Transduction efficiencies achieved with vector supernatants prepared in the sparged packed-bed bioreactor from the producer cell lines shown. CD34+/Thy+ cells from normal MPB were inoculated at unit gravity for 1 hour followed by a 3 hour spinoculation. Transduction efficiency is given as the expression of the Lyt2 surface antigen or the marking frequency of individual methyl cellulose colonies (CFU-C; Table 9).

Described above are safe, new retroviral vector packaging cell lines which can target distinct receptors on human cells and provide efficient gene transfer to human cells for gene therapy applications. The new lines described in Example 6 differ from the ProPak-A clone 6 of Example 1 since the Gag-Pol ORFs were expressed from the MLV-LTR promoter (Table 13) instead of the CMV promoter in ProPak-A.6. Despite carrying additional MLV-specific sequences, no RCR was detectable in supernatants or cells using a stringent test, namely extended co-culture of ProPak-X and ProPak-A.52 cells carrying the BC140revM10 vector. These ProPak vector particles are resistant to human serum, and should therefore remain functional if administered in vivo to humans.

The ProPak-X and ProPak-A cell lines produce particles which utilize distinct receptors on human cells, and the tropisms were confirmed by determining the ability to transduce cell lines from various species. Both receptors can be targeted by producing supernatants from a co-culture of ProPak-A and ProPak-X producer cell lines. The safety of the ProPak cell lines allows for efficient ping-pong amplification of the vector without the danger of RCR formation.

Using ProPak-A/X vector, 100% marking of CFU-C derived from CD34-positive cells purified from MPB was achieved. Significantly, the present experiments demonstrated expression of the Lyt2 transgene in 40% of the inoculated CD34-positive cells derived from MPB, 2 days post-inoculation.

The present experiments also indicated that high-efficiency gene transfer is best achieved with supernatants prepared from stable producer cell cultures. The approach described above is applicable to production from stable cells, existing and future vector systems.

As is apparent to those of skill in the art, various modifications and alterations to the above can be made without departing from the spirit and scope of the invention disclosed herein. Accordingly, the invention is limited only by the following claims.

What is claimed is:

1. A method for obtaining a recombinant retroviral packaging cell comprising:
   a. isolating a retroviral nucleic acid sequence encoding a minimal gag-pol open reading frame (ORF), said nucleic acid sequence having no flanking sequences of the gag-pol ORF, and inserting said nucleic acid sequence into a first expression plasmid;
   b. isolating a retroviral nucleic acid sequence encoding a minimal env ORF, said nucleic acid sequence having no flanking sequences of the env ORF, and inserting said nucleic acid sequence into a second expression plasmid,
   c. obtaining a eukaryotic cell free of an endogenous nucleic acid sequence which encodes the gag-pol ORF or the env ORF and which is derived from the retrovirus from which the minimal gag-pol ORF or env ORF is isolated; and
   d. introducing the first and second expression plasmids into the eukaryotic cell and expressing the nucleic acids encoding the minimal gag-pol ORF and env ORF to produce Gag, Pol and Env proteins, thereby producing the recombinant retroviral packaging cell.

2. The method of claim 1, wherein the retrovirus is a murine leukemia virus.

3. The method of claim 1, wherein the cell is a non-murine cell.

4. The method of claim 3, wherein the non-murine cell is a primate cell.

5. The method of claim 4, wherein the primate cell is a human cell.

6. The method of claim 3, wherein the non-murine cell is selected from the group consisting of Vero, HT-1080, D17 MRC-5, TE671, human embryonic kidney, and HeLa cells.

7. The method of claim 6, wherein the human embryonic kidney cells are human 293 cells (ATCC CRL 1573).

8. The method of claim 1, wherein the gag-pol ORF is a *Moloney murine* leukemia virus gag-pol gene.

9. The method of claim 1, wherein the env ORF is a murine leukemia virus env gene.

10. The method of claim 1, wherein at least one of the expression plasmids further comprises a selectable or detectable marker gene.

11. The method of claim 1, wherein the screening is done by ELISA.

12. The method of claim 11, wherein in the ELISA,

Env is detected using a primary antibody from hybridoma 83A25 followed by antiserum 79S-834, enzyme-conjugated antispecies antibody and enzyme substrate; and Gag is detected separately using a primary antibody from hybridoma R187 followed by antiserum 77S-227, enzyme-conjugated antispecies antibody and enzyme substrate.

13. The method of claim 8 wherein the gag-pol gene is expressed from the MMLV-LTR promoter.

14. The method of claim 8, wherein the gag-pol gene is expressed from the CMV-IE promoter or the RSV-LTR promoter.

15. The method of claim 1 wherein the gag-pol ORF and env ORF are isolated from the same retrovirus.

16. The method of claim 1, wherein the gag-pol ORF and env ORF are isolated from different retroviruses.

17. The method of claim 1, wherein the first and second expression plasmids are introduced into the eukaryotic cell in separate and sequential steps.

18. The method of claim 1, further comprising screening the cell of step (d) for retroviral Gag, Pol and Env production.

19. The recombinant retroviral packaging cell obtained by the method of claim 1.

20. The retroviral packaging cell of claim 19, wherein the cell produces an amphotropic Env.

21. The retroviral packaging cell of claim 19, wherein the cell produces a xenotropic Env.

22. The retroviral packaging cell of claim 19, wherein the cell produces a chimeric amphotropic/xenotropic Env.

23. The recombinant retroviral packaging cell of claim 19 wherein the packaging cell is a non-murine cell.

24. The recombinant retroviral packaging cell of claim 19 wherein the packaging cell is derived from human 293 having ATCC Accession No. CRL 1573.

25. The recombinant retroviral packaging cell of claim 19 wherein the packaging cell is a primate cell.

26. A method of producing a retroviral vector producer cell which comprises transducing the cells of claim 19 or 23 with a retroviral-based vector and subsequently propagating the cell under conditions favorable for the production and secretion of retroviral vector supernatant.

27. The method of claim 26, further comprising screening the producer cell for the ability to produce a vector supernatant having high transduction efficiency, comprising measuring the ability of the vector supernatant to transduce a target cell population with a transduction efficiency greater than that achieved with a vector supernatant produced from murine PA317-based cells.

28. The method of claim 27, wherein the target cell population is human 293 cells (ATCC CRL 1573).

29. The method of claim 26, wherein the retroviral-based vector used to transduce the cells was produced in human cells.

30. The retroviral vector producer cell produced by the method of claim 26.

31. A method of increasing the gene transduction efficiency of a cell, comprising transducing the cell with a retroviral vector supernatant produced from the culture of at least one retroviral vector producer cell of claim 30, wherein the transduction efficiency is increased over that achieved with a vector supernatant produced from murine PA317-based cells.

32. The method of claim 31, wherein the retroviral vector producer cell is derived from a packaging cell selected from group consisting of ProPak-A.6 (ATCC Accession No. CRL 12006), ProPak-A.52 (ATCC Accession No. CRL-12479) or ProPak-X.36 (ATCC Accession No. CRL 12007).

33. The method of claim 31 wherein the retroviral vector supernatant is produced from the co-culture of a first and a second complementary retroviral vector producer cell without replication competent retrovirus generation.

34. The method of claim 30 wherein the first retroviral vector producer cell is derived from an amphotropic packaging cell and the second vector producer cell is derived from a xenotropic packaging cell.

35. The method of claim 34 wherein the amphotropic packaging cell is ProPak-A.6 (ATCC Accesssion No. CRL 12006) or ProPak-A.52 (ATCC Accession No. CRL-12479), and the xenotropic packaging cell is ProPak-X.36 (ATCC Accesssion No. CRL 12007).

36. The method of claim 34 wherein both the amphotropic and xenotropic packaging cells are produced from human 293 cells (ATCC CRL 1573).

37. The method of claim 31 wherein the retroviral vector supernatant is produced from a stable retroviral vector producer cell culture.

38. The method of claim 31 wherein the transduced cell is a primary human hematopoietic cell.

39. The method of claim 31 wherein the transduced cell is a human hematopoietic stem cell.

40. The method of claim 38 wherein the hematopoietic cell is a CD34+ Thy1+ cell from mobilized peripheral blood or a CD4+ PBL.

41. The retroviral packaging cell of claim 19, capable of packaging retroviral vector sequences to form a retroviral vector producer cell that does not generate RCR after continuous culture for up to at least 12 weeks and that produces a recombinant, transducing retroviral vector particle, the retroviral vector particle characterized by:

a. being resistant to human complement; and b. having a high transduction efficiency.

42. The retroviral packaging cell line of claim 41 wherein the cell line is designated ProPak-A.6 and has ATCC Accession No. CRL 12006.

43. The retroviral packaging cell line of claim 41 wherein the cell line is designated ProPak A.52 having ATCC Accession No. CRL-12479.

44. The retroviral packaging cell line of claim 41 wherein the cell line is designated ProPak-X.36 and has ATCC Accession No.CRL 12007.

45. An expression plasmid for expressing gag-pol, comprising a gag-pol open reading frame from the start codon to the stop codon with no flanking sequences of the open reading frame.

46. An expression plasmid for expressing env, comprising an env open reading frame from the start codon to the stop codon with no flanking sequences of the open reading frame.

* * * * *

```
                        SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
         (A) LENGTH: 45 base pairs
         (B) TYPE: nucleic acid
         (C) STRANDEDNESS: single
         (D) TOPOLOGY: linear (xi) SEQUENCE DESCRIPTION: SEQ ID NO:1:

AAAAAAAAGC GGCCGCGCCG CCACCATGGG CCAGACTGTT ACCAC                        45

(2) INFORMATION FOR SEQ ID NO:2:

(i) SEQUENCE CHARACTERISTICS:
         (A) LENGTH: 36 base pairs
         (B) TYPE: nucleic acid
         (C) STRANDEDNESS: single
         (D) TOPOLOGY: linear (xi) SEQUENCE DESCRIPTION: SEQ ID NO:2:

AAAAAAAAGC GGCCGCTCAT TAGGGGGCCT CGCGGG                                  36

(2) INFORMATION FOR SEQ ID NO:3:

(i) SEQUENCE CHARACTERISTICS:
         (A) LENGTH: 38 base pairs
         (B) TYPE: nucleic acid
         (C) STRANDEDNESS: single
         (D) TOPOLOGY: linear (xi) SEQUENCE DESCRIPTION: SEQ ID NO:3:

TAATCTACGC GGCCGCCACC ATGGCGCGTT CAACGCTC                                38

(2) INFORMATION FOR SEQ ID NO:4:

(i) SEQUENCE CHARACTERISTICS:
         (A) LENGTH: 36 base pairs
         (B) TYPE: nucleic acid
         (C) STRANDEDNESS: single
         (D) TOPOLOGY: linear (xi) SEQUENCE DESCRIPTION: SEQ ID NO:4:

AATGTGATGC GGCCGCTCAT GGCTCGTACT CTATGG                                  36

(2) INFORMATION FOR SEQ ID NO:5:

(i) SEQUENCE CHARACTERISTICS:
         (A) LENGTH: 21 base pairs
         (B) TYPE: nucleic acid
         (C) STRANDEDNESS: single
         (D) TOPOLOGY: linear
```

-continued (xi) SEQUENCE DESCRIPTION: SEQ ID NO:5:

TCGATTAGTG AACGGATCCT T                                                    21

(2) INFORMATION FOR SEQ ID NO:6:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:6:

CTCCTGACTC CAATATTGCA G                                                    21

(2) INFORMATION FOR SEQ ID NO:7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:7:

TCGACGTTGT CACTGAAGCG                                                      20

(2) INFORMATION FOR SEQ ID NO:8:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:8:

GCTCTTCGTC CAGATCATCC                                                      20